United States Patent
Spiegel et al.

(10) Patent No.: US 10,188,727 B2
(45) Date of Patent: Jan. 29, 2019

(54) BIFUNCTIONAL MOLECULES WITH ANTIBODY-RECRUITING AND ENTRY INHIBITORY ACTIVITY AGAINST THE HUMAN IMMUNODEFICIENCY VIRUS

(71) Applicant: YALE UNIVERSITY, New Haven, CT (US)

(72) Inventors: David Spiegel, New Haven, CT (US); Christopher Parker, Medina, OH (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/883,959

(22) Filed: Oct. 15, 2015

(65) Prior Publication Data

US 2016/0082102 A1 Mar. 24, 2016

Related U.S. Application Data

(62) Division of application No. 13/501,592, filed as application No. PCT/US2010/052344 on Oct. 12, 2010, now Pat. No. 9,181,224.

(Continued)

(51) Int. Cl.
*C07D 405/14* (2006.01)
*C07D 403/12* (2006.01)
(Continued)

(52) U.S. Cl.
CPC .......... *A61K 39/385* (2013.01); *A61K 9/0019* (2013.01); *A61K 9/0053* (2013.01);
(Continued)

(58) Field of Classification Search
CPC ............ A61K 31/4745; A61K 2300/00; A61K 2039/54; A61K 2039/57; A61K 2039/58;
(Continued)

(56) References Cited

U.S. PATENT DOCUMENTS 7,115,262 B1 10/2006 Berger et al.
9,181,224 B2 * 11/2015 Spiegel .............. A61K 31/4745
(Continued)

FOREIGN PATENT DOCUMENTS

WO WO9215326 A2 * 9/1992
WO 2011046946 4/2011

OTHER PUBLICATIONS

Wang et al., Modification and Structure-activity relationship of a small molecule HIV-1 inhibitor targeting the viral envelope glycoprotein gp120, Org. Biomol. Chem., vol. 3:1781-1786 (Apr. 12, 2005).*

(Continued)

*Primary Examiner* — Randall L Beane
(74) *Attorney, Agent, or Firm* — Henry D. Coleman; R. Neil Sudol

(57) ABSTRACT

The present invention is directed to new bifunctional compounds and methods for treating HIV infections. The bifunctional small molecules, generally referred to as ARM-H's, function through orthogonal pathways, by inhibiting the gp120-CD4 interaction, and by recruiting anti-DNP antibodies to gp120-expressing cells, thereby preventing cell infection and spread of HIV. It has been shown that ARM-H's bind to gp120 and gp-120 expressing cells competitively with CD4, thereby decreasing viral infectivity as shown by an MT-2 cell assay, the binding leading to formation of a ternary complex by recruiting anti-DNP antibodies to bind thereto, the antibodies present in the ternary complex promoting the complement-dependent destruction of the gp120-expressing cells. Compounds and methods are described herein.

6 Claims, 11 Drawing Sheets

Related U.S. Application Data

(60) Provisional application No. 61/278,913, filed on Oct. 13, 2009.

(51) Int. Cl.
| | |
|---|---|
| *A61K 39/385* | (2006.01) |
| *A61K 31/4745* | (2006.01) |
| *A61K 45/06* | (2006.01) |
| *B82Y 5/00* | (2011.01) |
| *C07D 405/04* | (2006.01) |
| *C07D 471/04* | (2006.01) |
| *A61K 9/00* | (2006.01) |
| *A61K 47/54* | (2017.01) |
| *A61K 47/68* | (2017.01) |
| *A61K 39/00* | (2006.01) |

(52) U.S. Cl.
CPC .......... *A61K 31/4745* (2013.01); *A61K 45/06* (2013.01); *A61K 47/545* (2017.08); *A61K 47/6897* (2017.08); *B82Y 5/00* (2013.01); *C07D 403/12* (2013.01); *C07D 405/04* (2013.01); *C07D 405/14* (2013.01); *C07D 471/04* (2013.01); *A61K 2039/54* (2013.01); *A61K 2039/57* (2013.01); *A61K 2039/58* (2013.01); *A61K 2039/6012* (2013.01); *A61K 2039/627* (2013.01)

(58) Field of Classification Search
CPC ...... A61K 2039/6012; A61K 2039/627; A61K 39/385; A61K 45/06; A61K 47/48061; A61K 47/48746; A61K 9/0019; A61K 9/0053; B82Y 5/00; C07D 403/12; C07D 405/00
See application file for complete search history.

(56) References Cited

U.S. PATENT DOCUMENTS

| | | | |
|---|---|---|---|
| 9,562,038 B2 * | 2/2017 | Spiegel | ................ C07D 405/14 |
| 2003/0069245 A1 | 4/2003 | Wallace et al. | |
| 2007/0173636 A1 | 7/2007 | Danishefsky et al. | |
| 2009/0087428 A1 | 4/2009 | Chan et al. | |

OTHER PUBLICATIONS

Shokat et al., Redirecting the Immune Response: Ligand-Mediated Immunogenicity, J. Am. Chem. Soc., vol. 113:1861-1862 (1991).*
Parker et al., An Antibody-recruiting Small Molecule That Targets HIV gp120, J. Am. Chem. Soc., vol. 131:16392-16394 (Oct. 19, 2009) and 21 pages of Supp., 24 total pages.*
Medicine at Yale, "New NIH program funds scientific 'innovators' at Yale", Medicine@Yale, vol. 3(6):1-8 (Nov./Dec. 2007).*
Rostovtsev et al, A stepwise Huisgen Cycloaddition Process: Copper(I)-Catalyzed Regioselective "Ligation" of Azide and Terminal Alkynes, Anqew. Chem. Int. Ed. vol. 41(14):2596-2599 (2002).*
AASA-Chapman MMI, et al. Detection of Antibody-Dependent Complement-Mediated Inactivation of both Autologous and Heterologous Virus in Primary Human Immunodeficiency Virus Type 1 Infection. J Virol, 2005;79:2823-2830.
Allen TM. Ligand-Targeted Therapeutics in Anticancer Therapy. Cancer, 2002;2:750-763.
Bertozzi CR, Bednarski MD. Antibody Targeting to Bacterial Cells Using Receptor-Specific Ligands. J Am Chem Soc, 1992;114:2242-2245.
Bertozzi CR, Bednarski MD. A Receptor-Mediated Immune Response Using Synthetic Glycoconjugates. J Am Chem Soc, 1992;114:5543-5546.
Brekke OH, Sandlie I. Therapeutic Antibodies for Human Diseases at the Dawn of the Twenty-First Century. Nat Rev Drug Discovery, 2003;2:52-62.
Carlson C, et al. Selective Tumor Cell Targeting Using Low-Affinity, Multivalent Interactions. ACS Chem Biol, 2007;2:119-127.
Dean RB, Dixon WJ. Simplified Statistics for Small Numbers of Observations. Anal Chem, 1951;23:636-638.
Efstathiou CE. Estimation of type I error probability from experimental Dixon's "Q" parameter on testing for outliers withing small size data sets. Talanta, 2006;69:1068-1071.
Farah FS. Natural Antibodies Specific to the 2,4-Dinitrophenyl Group. Immunology, 1973;25:217-226.
Geczy AF, Baumgarten A. Lymphocyte Transformation in Contact Sensitivity. Immunology, 1970;19:189-203.
Gerencer M, et al. The role of complement and gp120-specific antibodies in virus lysis and CD4+ T cell depletion in HIV-1-infected patients. Microb Pathog, 1998;25:253-266.
Gong Y, et al. Membrane Activation: Selective Vesicle Fusion via Small Molecule Recognition. JACS, 2006;128:14430-14431.
Haertle T, et al. Metabolism and Anti-human Immunodeficiency Virus-1 Activity of 2-Halo-2',3'-dideoxyadenosine Derivatives. J Biol Chem, 1988;263:5870-5875.
Harada S, et al. Infection of HTLV-III/LAV in HTLV-1-Carrying Cells MT-2 and MT-4 and Application in a Plaque Assay. Science, 1985;229;563-566.
Ho H, et al. Envelope Conformational Changes Induced by Human Immunodeficiency Virus Type 1 Attachment Inhibitors Prevent CD4 Binding and Downstream Entry Events. J Vir, 2006;80:4017-4025.
Jormalainen S, Maleka O. Anti-hapten antibodies in normal sera. Eur J Immunol, 1971;1:471-478.
Karjalainen K, Makela O. Concentrations of three hapten-binding immunoglobulins in pooled normal human serum. Eur J Immunol, 1976;6:88-93.
Kong R, et al. Prediction of the binding mode between BMS-378806 and HIV-1 gp120 by docking and molecular dynamics simulation. Biochim Biophys Acta, 2006;1764:766-7728.
Krishnamurthy VM, et al. Promotion of opsonization by antibodies and phagocytosis of Gram-positive bacteria by a bifunctional polyacrylamide. Biomaterials, 2006;27:3663-3674.
Li J, et al. Bacteria Targeted by Human Natural Antibodies Using alpha-Gal Conjugated Receptor-specific Glycopolymers. Bioorg Med Chem, 1999;7:1549-1558.
Lu Y, et al. Folate-Targeted Dinitrophenyl Hapten Immunotherapy: Effect of Linker Chemistry on Antitumor Activity and Allergic Potential. Mol Pharm, 2007;4:695-706.
Miranda LR, et al. Cell surface expression of the HIV-1 envelope glycoproteins is directed from intracellular CTLA-4-containing regulated secretory granules. Proc Natl Acad Sci USA, 2002;99:8031-8036.
Mosmann TJ. Rapid Colorimetric Assay for Cellular Growth and Survival: Application to Proliferation and Cytotoxicity Assays. Immunol Methods, 1983;65:55-63.
Naicker KP, et al. Design and synthesis of alphaGal-conjugated peptide T20 as novel antiviral agent for HIV-immunotargeting. Biomol Chem, 2004;2:660-664.
Ortega E, et al. Natural DNP-Binding Immunoglobulins and Antibody Multispecificity. Mol Immunol, 1984;21:883-888.
Owen R, et al. Bifunctional Ligands that Target Cells Displaying the alpha(v)Beta(3) Integrin. ChemBioChem, 2007;8:68-82.
Popkov M, et al. Small molecule drug activity in melanoma models may be dramatically enhanced with an antibody effector. Intl J Cancer, 2006;119:1194-1207.
Popovic M, et al. T4 Positive Human Neoplastic Cell Lines Susceptible to and Permissive for HTLV-III. Lancet, 1984;2:1472-1473.
Popovic M, et al. Detection, Isolation, and Continuous Production of Cytopathic Retroviruses (HTLV-III) from Patients with AIDS and Pre-AIDS. Science, 1984;224:497-500.
Rader C, et al. Chemically programmed monoclonal antibodies for cancer therapy: Adaptor immunotherapy based on a covalent antibody catalyst. Proc Natl Acad Sci USA, 2003;100:5396-5400.
Ratner L, et al. Complete nucleotide sequence of the AIDS virus, HTLV-III. Nature, 1985;313:277-284.
Rostovtsev VV, et al. A Stepwise Huisgen Cycloaddition Process: Copper(I)-Catalyzed Regioselective "Ligation" of Azides and Terminal Alkynes. Angew Chem, 1nt, Ed. 2002;41:2596-2599.

(56) References Cited

OTHER PUBLICATIONS

Shokat KM, Schultz PG. J Am Chem Soc, 1991;113:1861-1862.

Spear GT, et al. Complement activation by human monoclonal antibodies to human immunodeficiency virus. J Virol, 1993;67:53-59.

Takefman DM, et al. Mechanisms of Resistance of HIV-1 Primary Isolates to Complement-Mediated Lysis. Virology, 1998;246:370-378.

Tornoe C, et al. Peptidotriazoles on Solid Phase: [1,2,3]-Triazoles by Regiospecific Copper(I)-Catalyzed 1,3-Dipolar Cycloadditions of Terminal Alkynes to Azides. J Org Chem, 2002;67:3057-3064.

Trujillo JR, et al. Shared Antigenic Epitopes on the V3 Loop of HIV-1 gp120 and Proteins on Activated Human T Cells. Virology, 1998;246:53-62.

Wang JF, et al. Modification and structure-activity relationship of a small molecule HIV-1 inhibitor targeting the viral envelope glycoprotein gp120. Org Biomol Chem, 2005;3:1781-1786.

Wang T, et al. Discovery of 4-Benzoyl-1[(4-methoxy-1H-pyrrolo[2,3-b]pyridin-3-yl)oxoacetyl]-2-(R)-methylpiperazine (BMS-378806): A Novel HIV-1 Attachment Inhibitor That Interferes with CD4-gp120 Interactions. J Med Chem, 2003;46:4236-4239.

Weiss CD, White JM. Characterization of stable Chinese hamster ovary cells expressing wild-type, secreted, and glycosylphosphatidylinositol-anchored human immunodeficiency virus type 1 envelope glycoprotein. J Vir, 1993;67:7060-7066.

Zych A, Iverson B. Synthesis and Conformational Characterization of Tethered, Self-Complexing 1,5-Dialkoxynaphthalene/1,4,5,8-Naphthalenetetracarboxylic Diimide Systems. JACS 2000;122:8898-8909.

NIH.gov, Project Information: 1DP20D002913-01, projectreporter.nih.gov/, (Project start date: Sep. 30, 2007), available at http://projectreporter.nih.gov/project_info_description.cfm?aid=7431968&icde=0 (last visited May 9, 2013).

Corson TW, et al. Design and application of bifunctional small molecules: why two heads are better than one. ACS Chem Biol, Oct. 2008;3(11):677-692.

Faust A, et al. Synthesis and evaluation of a novel fluorescent photoprobe for imaging matrix metalloproteinases. Bioconjug Chem, Apr. 2008;19(5):1001-1008.

Klein JS, et al. Examination of the contributions of size and avidity to the neutralization mechanisms of the anti-HIV antibodies b12 and 4E10. PNAS, Apr. 2009;106(18):7385-7390.

Low PS, et al. Discovery and development of folic-acid-based receptor targeting for imaging and therapy of cancer and inflammatory diseases. Acc Chem Res, Jul. 2007;41(1):120-129.

Mack ET, et al. Exact analysis of ligand-induced dimerization of monomeric receptors. Anal Chem, Jun. 2008;80(14):5550-5555.

Pannecouque C, et al. Tetrazolium-based colorimetric assay for the detection of HIV replication inhibitors: revisited 20 years later. Nat Protoc, Feb. 2008;3(3):427-434.

Perdomo MF, et al. Neutralization of HIV-1 by redirection of natural antibodies. PNAS, Aug. 2008;105(34):12515-12520.

Popkov M, et al. Instant immunity through chemically programmable vaccination and covalent self-assembly. PNAS, Mar. 2009;106(11):4378-4383.

Rawool DB, et al. Utilization of Fc Receptors as a Mucosal Vaccine Strategy against an Intracellular Bacterium, *Francisella tularensis*. J Immunol, Apr. 2008;180(8):5548-5557.

Bojesen SE, et al. Plasma YKL-40 levels in healthy subjects from the general population. Clin Chim Acta, Apr. 2011;412(9-10):709-712.

Hall IE, et al. A comparison of alternative serum biomarkers with creatinine for prediction allograft function after kidney transplantation. Transplantation, Jan. 2011;91(1):48-56.

Jang HR, et al. The interaction between ischemia-reperfusion and immune responses in the kidney. J Mol Med, Jun. 2009;87(9):859-864.

Lee CG, et al. Role of chitin and chitinase/chitinase-like proteins in inflammation, tissue remodeling, and injury. Annu Rev Physiol, Nov. 2010;73:479-501.

Yi YS, et al. Folate-targeted hapten immunotherapy of adjuvant-induced arthritis: comparison of hapten potencies. Mol Pharm, Apr. 2009;6(4):1228-1236.

\* cited by examiner

FIG. 15

| Molécule | EC$_{50}$ (Ab-recruiting) | IC$_{50}$ (CD4 inhib.) | MT-2 IC$_{50}$ |
|---|---|---|---|
| 4 | 37.9 | 19.9 | 6.4 |
| 29 | 42.5 | 59.5 | 7.1 |
| 30 | 45.8 | 45.2 | 46.0 |
| 31 | 19.8 | 47.9 | toxic |
| 32 | 10.4 | 49.0 | 9.1 |
| 33 | No Activity | No Activity | toxic |
| 28 | 49.3 | 46.2 | toxic |
| 34 | 90.0 | 65.9 | >100 |
| 35 | 0.952 | No Activity | 7.1 |
| 22 | 0.973 | 0.330 | 0.460 |
| 36 | 0.892 | No Activity | 100 |
| 37 | 2.90 | No Activity | No Activity |
| 26 | 0.893 | No Activity | No Activity |
| 38 | 13.9 | 0.220 | - |
| 1 | - | 8.70 | 0.032 |
| 27 | - | 0.130 | 0.00064 |

BIFUNCTIONAL MOLECULES WITH ANTIBODY-RECRUITING AND ENTRY INHIBITORY ACTIVITY AGAINST THE HUMAN IMMUNODEFICIENCY VIRUS

PRIORITY CLAIM

This application claims priority from and is a continuation application of U.S. National Phase patent application Ser. No. 13/501,592 filed Jun. 28, 2012, now U.S. Pat. No. 9,181,224, issued Nov. 10, 2015, which is based upon International Patent Application No. PCT/US2010/052344 of International Filing Date 12 Oct. 2010 entitled "BIFUNCTIONAL MOLECULES WITH ANTIBODY-RECRUITING AND ENTRY INHIBITORY ACTIVITY AGAINST THE HUMAN IMMUNODEFICIENCY VIRUS", said international patent application claiming priority from U.S. provisional application Ser. No. 61/278,913 entitled "Development of Small Molecule Antibody Recruiting Therapeutics for the Treatment of HIV", filed Oct. 13, 2009, the entire contents of said three priority applications being incorporated by reference herein.

GRANT SUPPORT

This invention was made with support from the National Institutes of Health grant no. 1DP2OD002913. Consequently, the government retains rights in the invention.

FIELD OF THE INVENTION

The present invention relates to bifunctional molecules for inhibiting Human Immunodeficiency Virus (HIV) infection through binding to the HIV glycoprotein gp 120, while also engaging in antibody-recruiting for attracting and binding antibodies which combat the bound HIV.

BACKGROUND AND DISCUSSION OF THE INVENTION

In recent years, antibody based therapeutics have become important instruments in treating human disease. (Brekke, O. H.; Sandlie. I. Nat. Rev. Drug Discovery 2003, 2, 52-62.) Current antibody-based therapeutics function either by blocking the effector actions of pathological molecules, or by targeting specific epitopes on cell surfaces for immune-mediated destruction. However, these approaches suffer from certain limitations, including severe side effects, lack of oral bioavailability, and high cost. (Allen. T. M. Nat. Rev. Cancer 2002, 2, 750-763.) Thus, alternative methods are being sought that would still exploit the powerful cytolytic potential of antibodies already present in the human blood stream yet avoid many of these disadvantages.

Acquired Immune Deficiency Syndrome (AIDS) is a world-wide epidemic that has claimed many lives and severely debilitated many more through immune suppression. A great deal of effort has been directed toward the development of a vaccine for this disease, without success. The failure to develop an effective vaccine underscores the need for new prevention and treatment strategies toward this disease.

The human immune system is highly versatile in its ability to target and destroy foreign pathogens. HIV, however, is an elusive virus to the body's immune system which has evolved mechanisms both to evade and to destroy the immune response of human hosts in the process of causing AIDS. Researchers recently found that one of the shortfalls of the human immune system in combating HIV is also one the antibody's stronger point against other viruses; its structure.

An antibody is a Y-shaped molecule with two epitopes comprising antigen recognizing proteins on the two Y tips. These two epitopes allow the antibody to bind to two proteins on the antigen's surface, creating a stronger bond when compared to a one-epitope protein bond. Viruses have proteins extending from their viral coat, which are the proteins the antibodies bind to.

HIV has fewer proteins than normal viruses. The proteins are placed farther apart and this structural difference is believed responsible for the antibody's epitopes being unable to bind to two different HIV surface proteins (See Klein et al. "Examination of the contributions of size and avidity to the neutralization mechanisms of the anti-HIV antibodies b12 and 4E10" Proceedings of the National Academy of Sciences, 2009 Abstract).

HIV has also been shown to bind to a surface molecule known as the CD4 or T4 receptor, which is present on various cells susceptible to HIV infection, including T lymphocytes and macrophages. (See Shaw et al., Science 226, pp. 1165-1171 for a discussion of tropism of HTLV-III.)

A few methods for recruiting naturally occurring antibodies to cancer cells have appeared in the literature, but none are believed to have been explored directed to HIV (See Carlson, C.; Mowery, P.; Owen, R.; Dykhuizen, E. C.: Kiessling, L. ACS Chem. Biol. 2007, 2, 119-127; Owen. R.; Carlson, C; Xu, J.; Mowery, P.; Fasella, E.; Kiessling, L. ChemBioChem 2007, 8, 68-82; Popkov. M.: Gonzalez, E.; Sinha, S.; Barbas, C. Proc. Natl. Acad. Sci. U.S.A. 2009, 106, 4378-4383; Popkov, M.; Rader. C; Gonzalez, B.; Sinha. S.; Barbas, C. Intl. J. Cancer 2006, 119, 1194-1207; (25) Low, P.; Henne, W.; Doorneweerd, D. Acc. Chem. Res. 2008, 41, 120-129; Lu, Y.: You, F.; Vlahov, I.; Westrick. E.; Fan, M.; Low, P. S.; Leamon, C. P. Mol. Pharm. 2007, 4, 695-706. (27) Rader. C.; Sinha, S. C.; Popkov, M.; Lerner, R. A.; Barbas, C. F. Proc. Natl. Acad. Sci. U.S.A. 2003, 100, 5396-5400), bacteria (Bertozzi, C. R.; Bednarski, M. D. J. Am. Chem. Soc. 1992, 114, 5543-5546; Bertozzi, C. R.; Bednarski. M. D. J. Am. Chem. Soc. 1992. 114, 2242-2245; Li, J.: Zacharek, S.; Chen, X.; Wang, J. Q.: Zhang, W.; Janczuk, A.; Wang, P. G. Bioorg. Med. Chem. 1999, 7, 1549-1558; Krishnamurthy, V. M.; Quinton, L. J.; Estroff. L. A.; Metallo, S. J.; Isaacs, J. M.; Mizgerd, J. P; Whitesides, G. M. Biomaterials 2006, 27, 3663-3674), and viruses ((32) Shokat, K. M.; Schultz, P. G. J. Am. Chem. Soc. 1991, 113, 1861-1862; Naicker, K. P.: Li, H.; Heredia, A.; Song, H.; Wang, L. Org. Biomol. Chem. 2004, 2, 660-664; Perdomo, M. F.: Levi. M.; Ilberg, M. S.; Vahlne, A. Proc. Natl. Acad. Sci. U.S.A. 2008, 105, 6).

In the HIV realm, most approaches have relied upon protein- or peptide-based antibody targeting constructs. For example, Shokat and Schultz (Shokat, K. M.; Schultz, P. G. J. Am. Chem. Soc. 1991, 113, 1861-1862) first demonstrated that anti-DNP antibodies could be redirected to immobilized protein targets (gp120 and streptavidin) as a therapeutic strategy toward HIV. More recent work in this vein has employed peptide-R-Gal conjugates to target human anti-Gal antibodies to HIV-infected cells. (Naicker, K. P.: Li, H.; Heredia, A.; Song, H.; Wang, L. Org. Biomol. Chem. 2004, 2, 660-664; Perdomo, M. F.: Levi. M.; Ilberg, M. S.; Vahlne, A. Proc. Natl. Acad. Sci. U.S.A. 2008, 105, 6)

While these peptide conjugates were shown to be effective in killing Env-expressing cells, they were also found to exhibit some non specific cytotoxicity. Bertozzi, C. R.; Bednarski, M. D. J. Am. Chem. Soc. 1992, 114, 5543-5546.

The present work sought to address these deficiencies, by providing compositions for treating HIV infection which can improve the immune system's ability to respond to HIV infection. We have discovered one way to assist the body is to recruit existing antibodies to attack HIV. Specifically, we have developed bifunctional molecules (Corson. T. W.; Aberle, N.; Crews, C. M. ACS Chem. Biol. 2008, 3, 677-692) capable of which inhibit the pathogenic behavior of HIV through two distinct mechanisms: (1) by interfering with viral entry via antagonism of the interaction between the viral envelope protein gp120 and the human protein CD4, and (2) by recruiting anti-dinitrophenyl ("anti-DNP") antibodies, a population of antibodies present in high concentrations in the human bloodstream, to the surface of the HIV virus and/or HIV-infected cells.

Antibodies recognizing the DNP epitope have been estimated to constitute 1% of circulating IgM and 0.8% of circulating IgG. See: (a) Karjalainen, K., Makela. O. Eur. J. Immunol. 1976, 6, 88-93. (b) Farah, F. S. Immunology 1973, 25, 217-226. The prevalence of anti-DNP antibodies has been estimated at between 18 and 90% of humans. See: (c) Ortega, E.; Kostovetzky. M.; Larralde, C. Mol. Immunol. 1984, 21, 883-888. (d) Jormalainen, S.; Makela. O. Eur. J. Immunol. 1971, 1, 471-478. Consequently, administration of a bifunctional molecule which can recruit these existing antibodies to attack HIV in a patient suffering from HIV infection may provide a basis for an effective treatment for the symptoms associated with HIV infection.

SUMMARY OF THE INVENTION

The present invention relates to ARM-H ("Antibody-Recruiting Molecules targeting HIV") compounds according to the general formula:

Where ABT is an antibody binding terminus (moiety) comprising a hapten which is capable of binding to an antibody present in a patient;

PBT is a pathogen binding terminus (moiety) which is capable of binding to gp120 envelope protein on HIV virus or a cell surface of CD4 cells which are infected with HIV (HIV+) in said patient;

L1 is a linker molecule which chemically links PBT to CT in a molecule;

L2 is a linker molecule which chemically links ABT to CT in a molecule;

CT is a bond or a connector molecule which links L1 and/or L2 to ABT and/or PBT;

Each n and m in a molecule is independently an integer from 1 to 15, 1 to 10, 1 to 5, 1 to 3, 2 to 3, 2 to 5, 1 to 2 or 1 (preferably m and n are each 1);

Each j is independently 0, 1, 2, 3, 4 or 5 (preferably 0 or 1, more preferably 1); and Each k is independently 0, 1, 2, 3, 4 or 5 (preferably 0 or 1, more preferably 1), with the proviso that k and j are other than 0 when CT is a bond.

or a pharmaceutically acceptable salt, solvate or polymorph thereof.

In an additional aspect of the invention, a pharmaceutical composition comprises an effective amount of a ARM-H compound as described above, optionally and preferably in combination with a pharmaceutically acceptable carrier, additive or excipient. In alternative aspects, pharmaceutical combination compositions comprise an effective amount of a ARM-H compound as described herein, in combination with at least one additional agent which is used to treat HIV.

Certain preferred bifunctional compounds according to the present invention have the following chemical structure:

Where $X_2$ and $X_3$ are each independently a bond, H, $C_1$-$C_6$ alkyl, O—($C_1$-$C_6$ alkyl), (such that the linker and ABT are absent from the molecule at that position), O, $CH_2$, $NR^1$, S(O), $S(O)_2$, —$S(O)_2O$, —$OS(O)_2$, or $OS(O)_2O$;

$R^1$ is H or a $C_1$-$C_3$ alkyl group;

i is 0 or 1, preferably 1;

$Y_2$ is N or a C—$R^Y$ group;

$R^Y$ is H, $C_1$-$C_6$ alkyl, O—($C_1$-$C_6$ alkyl), an aryl or heteroaryl group;

$Y_3$ is H or a $C_1$-$C_3$ alkyl group (disposed out of or into the plane, preferably out of the plane on the chiral carbon;

Linker is a linker as otherwise disclosed herein and includes a connector (CT) which may be a bond or a chemical connector; and ABT is an antibody binding terminus as otherwise described herein (preferably a DNP group) with the proviso that at least one of $X_2$ and $X_3$ is other than H, $C_1$-$C_6$ alkyl, O—($C_1$-$C_6$ alkyl) such that the molecule contains at least one ABT moiety, or a pharmaceutically acceptable salt, solvate or polymorph thereof.

Preferred bifunctional compounds for use in the present invention include those which are derived from BMS-378806 according to the chemical formula:

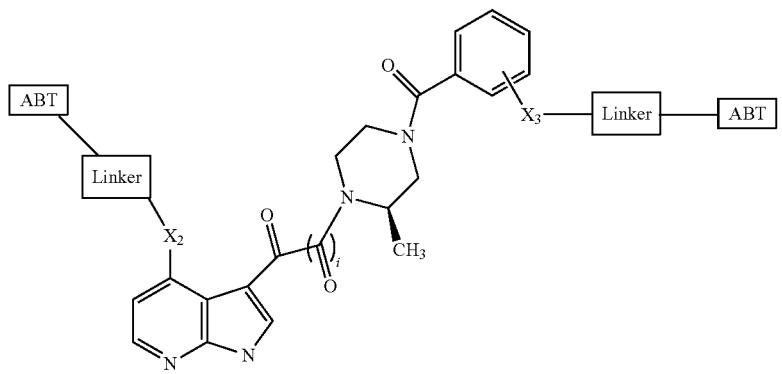

Where $X_2$ and $X_3$ are each independently a bond, H, $C_1$-$C_6$ alkyl, O—($C_1$-$C_6$ alkyl) (such that the linker and ABT are absent from the molecule at that position), O, $CH_2$, $NR^1$, S(O), $S(O)_2$, —$S(O)_2$O, —$OS(O)_2$, or $OS(O)_2$O;
$R^1$ is H or a $C_1$-$C_3$ alkyl group;
i is 0 or 1, preferably 1;
[Linker] is a linker as otherwise disclosed herein and includes a connector (CT) which may be a bond or a chemical connector; and
[ABT] is an antibody binding terminus as otherwise described here (preferably a DNP group) with the proviso that at least one of $X_2$ and $X_3$ is other than H, $C_1$-$C_6$ alkyl or O—($C_1$-$C_6$ alkyl) (such that the molecule contains at least one ABT moiety),
or a pharmaceutically acceptable salt, solvate or polymorph thereof.

Alternative bifunctional compounds for use in the present invention include those which are included in compounds according to the chemical formula:

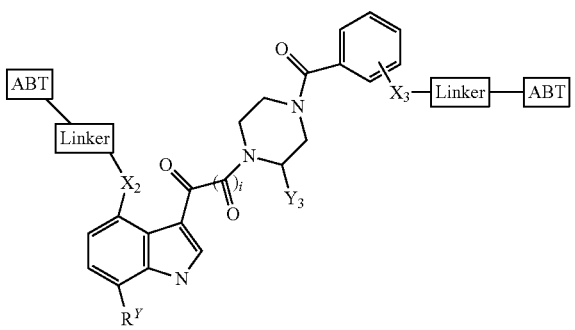

Where $X_2$ and $X_3$ are each independently a bond, H, $C_1$-$C_6$ alkyl, O—($C_1$-$C_6$ alkyl) (such that the linker and ABT are absent from the molecule at that position), O, $CH_2$, $NR^1$, S(O), $S(O)_2$, —$S(O)_2$O, —$OS(O)_2$, or $OS(O)_2$O;
$R^1$ is H or a $C_1$-$C_3$ alkyl group, preferably H;
i is 0 or 1, preferably 1;
$R^Y$ is H, $C_1$-$C_6$ alkyl, O—($C_1$-$C_6$ alkyl), an aryl or heteroaryl group as otherwise described herein, preferably a phenyl, naphthyl, pyridyl (2-, 3- or 4-pyridyl group), thiazolyl (2-, 4- or 5-thiazole), isothiazolyl, oxazolyl (2-, 4- or 5-oxazole), isoxazolyl, furanyl (2- or 3-furan) or thiophenyl (2- or 3-thiophene);
$Y_3$ is H or a $C_1$-$C_3$ alkyl group (disposed out of or into the plane, preferably out of the plane on the chiral carbon to which it is attached;
[Linker] is a linker as otherwise disclosed herein and includes a connector (CT) which may be a bond or a chemical connector; and
[ABT] is an antibody binding terminus as otherwise described herein (preferably a DNP group) with the proviso that at least one of $X_2$ and $X_3$ is other than H, $C_1$-$C_6$ alkyl or O—($C_1$-$C_6$ alkyl) (such that the molecule contains at least one ABT moiety),
or a pharmaceutically acceptable salt, solvate or polymorph thereof.

In certain preferred multifunctional compounds, the connector is a multifunctional compound which is chemically bonded to three or more linkers to which are bonded two or more PBT groups and/or ABT groups. In addition, each PBT group and/or ABT group can itself be bonded to more than one linker molecule, resulting in complex compounds containing more than two PBT groups and/or ABT groups.

In a further aspect of the invention, compounds according to the present invention are used to treat and/or reduce the likelihood of an HIV infection or a secondary effect of HIV (such as AIDS, ARC and related disease states or conditions which occur secondary to an HIV infection) in a patient. The method of treating and/or reducing the likelihood of an HIV infection or secondary effect of an HIV cancer comprises administering to a patient in need an effective amount of a ARM-H compound as otherwise described herein in combination with a pharmaceutically acceptable carrier, additive or excipient, optionally in further combination with at least one additional agent which is effective in treating and/or reducing the likelihood of an HIV infection, or one or more of its secondary conditions or effects.

The present invention also relates to instances in which destruction of CD4 cells which are infected with HIV (HIV+ CD4 cells) may be useful to inhibit latent HIV infections from becoming active. In this aspect of the invention, destruction of HIV+ CD4 cells in an HIV positive patient may be used to inhibit or more completely eradicate an HIV infection and/or reduce the likelihood of an occurrence or recurrence of HIV in a patient who is HIV positive.

The present invention also relates to a method for binding and eliminating HIV in a patient comprising administering to a patient infected with HIV, an effective amount of a ARM-H compound as otherwise described herein.

Thus, the present invention presents unique, non-peptidic, bifunctional molecules which can operate through the bifunctional mechanisms specified above in treating HIV.

The realization that viruses may exert cell and tissue tropism by attachment at highly specific sites on cell membrane receptors has encouraged investigators in the past to seek agents which would bind at the viral receptor sites of cell membranes and thus prevent binding of a specific virus to these cells.

Specifically, HIV has been shown to bind to a surface molecule known as the CD4 or T4 receptor which is present on various cells susceptible to HIV infection, including T lymphocytes and macrophages. The binding occurs via the HIV envelope protein, gp120.

It is an object of the present invention to provide bifunctional compounds that would act to alleviate the symptoms of AIDS by binding a bifunctional molecule which has a first terminus for binding to the gp120 envelope protein, the bifunctional molecule having a second antibody recruiting terminus which attracts antibodies already circulating throughout the body, to form a ternary complex between anti-DNP antibodies and gp120 and/or gp120-expressing cells, the antibodies attacking the HIV engaged by the bifunctional molecule. These bifunctional (which term also includes multifunctional) molecules are thus generically referred to herein as "Antibody-Recruiting Molecules targeting HIV" or "ARM-H".

The inventive ARM-H molecules are "bifunctional" in that they possess a at least one pathogen binding terminus (PBT) and at least one antibody recruiting terminus (ABT) connected by at least one linker and a connector molecule. The PBT is designed to bind to the HIV glycoprotein gp120 (gp120 on the viral membrane as well as gp120 displayed on infected cells). The ABT is designed to bind and/or recruit antibodies to the site of the binding of the ARM-H compound.

In one embodiment of the invention, a bifunctional ARM-H molecule is described which is capable of redirecting a population of anti-hapten (e.g. anti-dinitrophenyl or anti-DNP) antibodies, which represent a population of antibodies present in high concentrations in the human blood stream ("endogenous antibodies"), to the HIV gp120 Env gene product. The Env glycoprotein, a complex between gp120 and membrane-bound gp 41, is expressed on both the surface of the HIV virus and on virus-infected cells, especially CD4 cells. (Miranda. L. R.; Schaefer, B. C.; Kupfer. A.; Hu, Z. X.; Franzusoff, A. Proc. Natl. Acad. Sci. U.S.A, 2002, 99, 8031-8036). The gp120 component of Env mediates the first step in viral entry into human cells by binding the protein CD4.

According to the present invention, a ternary complex is formed between anti-hapten (e.g. DNP or other hapten) antibodies, ARM-H, and Env-expressing cells which mediates the complement-dependent destruction of these cells. Further, since ARM-H binds gp120 competitively with CD4, it also inhibits the entry of live HIV into human T-cells. Thus, ARM-H has the potential to interfere with the survival of HIV through multiple complementary mechanisms, and may also function as a prophylactic.

The ARM-H compounds of the invention are unique in that they represent a molecule-based, not a peptide and/or protein based, anti-HIV strategy for targeting the virus life cycle through mutually reinforcing molecular mechanisms, inhibiting virus entry while targeting Env-expressing cells for immune recognition and clearance. In general, the ARM-H molecules have certain advantages over proteins from a therapeutic standpoint because of their low propensity for immunogenicity, high metabolic stability, ready large-scale production, and relatively low cost. Molecule based antibody-recruiting therapeutics such as ARM-H have additional benefits over available treatment approaches to HIV. For example, directing HIV-infected cells and virus particles to Fcγ receptors on antigen-presenting cells enhances the presentation of viral antigens on MI-IC proteins and contributes to long-lasting anti-HIV immunity. (See Lu, Y.: You, F.; Vlahov, I.; Westrick. E.; Fan, M.; Low, P. S.; Leamon, C. P. Mol. Pharm. 2007, 4, 695-706, Rawool, D. B.; Bitsaktsis, C.; Li, Y.; Gosselin, D. R., Lin, Y.; Kurkure, N. Y.; Metzger, D. W.; Gosselin, E. J. J. Immunol, 2008, 180, 5548-5557) Critically, no non specific cytotoxicity was observed in either MT-2 or CHO cell lines in response to the inventive ARM-H molecules, limiting the possibility of encountering serious side effects from treatment therewith.

Furthermore, because anti-hapten (anti-DNP) antibodies are already present in the human blood stream, no prevaccination is necessary for ARM-H activity. Also, the binding of bifunctional molecule targeting agents to antibodies should prolong their plasma half-life, thus increasing their effectiveness. (See Rader. C.; Sinha, S. C.; Popkov, M.; Lerner, R. A.; Barbas, C. F. Proc. Natl. Acad. Sci. U.S.A. 2003, 100, 5396-5400)

Elucidation of the molecular details governing the interactions among ARM-H, gp120, and anti-DNP antibodies assists in optimization efforts as well as in the evaluation of this strategy in more complex biological models of HIV infection.

As stated above, the invention is directed to "bifunctional" molecules, the inventive molecules being "bifunctional" in that they possess a pathogen binding terminus (PBT) and an antibody recruiting terminus (ABT) connected by a linker. The PBT is designed to bind to the HIV glycoprotein gp120 (gp120 on the viral membrane as well as gp120 displayed on infected cells). The ABT is designed to bind antibodies and therefore redirect endogenous antibodies and hence the immune response to the pathogen. Formation of a ternary complex between these molecules, the antibodies, and the target pathogen, leads to targeted cytotoxicity through various mechanisms including antibody dependent cellular cytotoxicity (ADCC), or complement-dependent cytotoxicity (CDC).

The present invention is directed to pharmaceutical compositions comprising the above-described bifunctional molecules that can inhibit HIV entry into a target cell, while also recruiting antibodies to attack the HIV or an HIV infected cell, in a pharmaceutically acceptable carrier. As an aspect of the invention, therefore, we provide a pharmaceutical composition comprising a bifunctional molecule compound of the invention in association with a pharmaceutically acceptable carrier or excipient, adapted for use in human or veterinary medicine. Such compositions may be presented for use in conventional manner in admixture with one or more physiologically acceptable carriers or excipients. The compositions may optionally further contain one or more other therapeutic agents which may, if desired, be a different antiviral agent.

The bifunctional molecule compounds according to the invention may be formulated for oral, buccal, nasal, parenteral, topical or rectal administration.

In particular, the bifunctional molecule compounds according to the invention may be formulated for injection or for infusion and may be presented in unit dose form in ampoules or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients such as antimicrobial agents, or preservatives.

The compositions may contain from 0.001-99% of the active material.

The invention further provides a process for preparing a pharmaceutical composition which comprises bringing a bifunctional molecule compound of the invention into association with a pharmaceutically acceptable excipient or carrier.

For administration by injection or infusion, dosages and desired drug concentrations of the disclosed pharmaceutical compositions may vary depending on the particular use, patient condition, age, drug tolerance, etc., as would be understood by one skilled in the field. Consequently, the determination of an appropriate dosage and/or route of administration is well within the skill of an ordinary practitioner, and the compounds can certainly be formulated without undue experimentation for administration in the treatment of humans, for example, using standard and well known dose-response protocols.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other ARM-H compound which may be used to treat HIV infection or a secondary effect or condition thereof.

BRIEF DESCRIPTION OF THE DRAWINGS

FIG. 5A-1 are the results of immunoflourescent microscopy.

FIG. 15 shows the results of testing of the various compounds from FIG. 14 in antibody recruiting, CD4 cell inhibition and MT2 antiviral activity and cellular cytotoxicity testing as otherwise described herein.

DETAILED DESCRIPTION OF THE INVENTION

Figure 1:
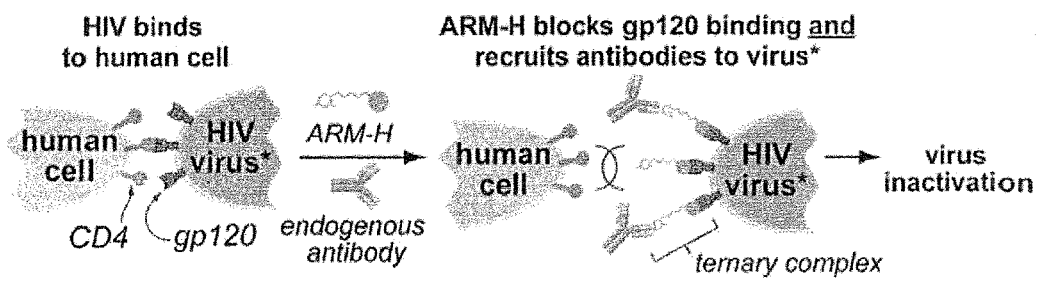
FIG. 1 illustrates the effects of ARM-H in forming a ternary complex between gp120 and an antibody.

The following terms are used to describe the present invention. In instances where a term is not specifically defined herein, that term is given an art-recognized meaning by those of ordinary skill applying that term in context to its use in describing the present invention.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methyl-propyl, cyclopropyl, cyclopropylmethyl, cyclobutyl, cyclopentyl, cyclopentylethyl, cyclohexylethyl and cyclohexyl. Preferred alkyl groups are $C_1$-$C_3$ alkyl groups.

"Aryl" or "aromatic", in context, refers to a substituted (with 1, 2 or 3, hydroxyl and/or halo groups (F, Cl, Br or I) and/or with 1, 2 or 3 $C_1$-$C_3$ alkyl groups) or unsubstituted monovalent aromatic radical having a single ring (e.g., benzene or phenyl) or multiple condensed rings (e.g., naphthyl, anthracenyl, phenanthryl) and can be bound to the compound according to the present invention at any position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, among others, which may be optionally substituted as described above.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for treating and/or reducing the likelihood of HIV infections or the secondary effects of HIV infections, especially including AIDS and/or ARC.

The term "effective" is used herein, unless otherwise indicated, to describe an amount of a compound or composition which, in context, is used to produce or effect an intended result, whether that result relates to the inhibition of the effects of a toxicant on a subject or the treatment of a subject for secondary conditions, disease states or manifestations of exposure to toxicants as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for HIV infection or having an HIV infection, including improvement in the condition through lessening or suppression of titers of HIV or at least one symptom of HIV, prevention or delay in progression of the disease, prevention or delay in the onset of disease states or conditions which occur secondary to HIV, including AIDS or ARC, among others. Treatment, as used herein, encompasses both prophylactic and therapeutic treatment. The term "prophylactic" when used, means to reduce the likelihood of an occurrence or the severity of an occurrence within the context of the treatment of HIV, as otherwise described hereinabove.

The term "human immunodeficiency virus" or "HIV" shall be used to describe human immunodeficiency viruses 1 and 2 (HIV-1 and HIV-2).

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria: T-cells have dropped below 200 or the patient has had at least one of the following defining illnesses—

Brain Toxoplasmosis
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)

Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent
Progressive multifocal leukoencephalopathy
*Salmonella* septicemia, recurrent
Wasting syndrome due to HIV The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the bifunction ARM-H compounds described above, are coadministered in combination with at least one additional anti-HIV agent as otherwise described herein in a cocktail for the treatment of HIV infections. In particularly preferred aspects of the invention, the co-administration of compounds results in synergistic anti-HIV activity of the therapy.

The term "additional anti-HIV agent" shall mean a traditional anti-HIV agent (ie., a non-bifunctional ARM-H compound as otherwise described herein) which may be co-administered to a patient along with ARM-H compounds according to the present invention in treating a patient for HIV. Such compounds include, for example, agents such as nucleoside reverse transcriptase inhibitors (NRTI), non-nucloeoside reverse transcriptase inhibitors, protease inhibitors and fusion inhibitors. Exemplary compounds include, for example, Amprenivir, Abacavir, Acemannan, Acyclovir, AD-439, AD-519, Adefovir dipivoxil, Alpha Interferon, Ansamycin, 097, AR 177, Beta-fluoro-ddA, BMS-232623 (CGP-73547), BMS-234475 (CGP-61755), CI-1012, Cidofovir, Curdlan sulfate, Cytomegalovirus Immune globin, Ganciclovir, Dideoxyinosine, DMP-450, Efavirenz (DMP-266), EL10, Famciclovir, FTC, GS 840, HBY097, Hypericin, Recombinant Human Interferon Beta, Interferon alfa-n3, Indinavir, ISIS-2922, KNI-272, Lamivudine (3TC), Lobucavir, Nelfinavir, Nevirapine, Novapren, Peptide T Octapeptide Sequence, Trisodium Phosphonoformate, PNU-140690, Probucol, RBC-CD4, Ritonavir, Saquinavir, Valaciclovir, Virazole Ribavirin, VX-478, Zalcitabine, Zidovudine (AZT), Tenofovir diisoproxil fumarate salt, Combivir, Abacavir succinate, T-20), AS-101, Bropirimine, CL246, EL10, FP-21399, Gamma Interferon, Granulocyte Macrophage Colony Stimulating Factor (GM-CSF), HIV Core Particle Immunostimulant, Interleukin-2 (IL-2), Immune Globulin Intravenous, IMREG-1, IMREG-2, Imuthiol Diethyl Dithio Carbamate, Alpha-2 Interferon, Methionine-Enkephalin, MTP-PE (Muramyl-Tripeptide), Granulocyte Colony Stimulating Factor (GCSF), Remune, rCD4 (Recombinant Soluble Human CD4-IgG), rCD4-IgG Hybrids, Recombinant Soluble Human CD4, Interferon Alfa 2a, SK&F1-6528, Soluble T4, Thymopentin, Tumor Necrosis Factor (TNF), AK602, Alovudine, Amdoxovir, AMD070, Atazanavir (Reyataz), AVX754 (apricitabine), Bevirimat, BI-201, BMS-378806, BMS-488043, BMS-707035, C31G, Carbopol 974P, Calanolide A, Carrageenan, Cellulose sulfate, Cyanovirin-N, Darunavir, Delavirdine, Didanosine (Videx), Efavirenz, Elvucitabine, Emtricitabine, Fosamprenavir (Lexiva), Fozivudine tidoxil, GS 9137, GSK-873,140 (aplaviroc), GSK-364735, GW640385 (brecanavir), HG0004, HGTV43, INCB9471, KP-1461, Lopinavir, Mifepristone (VGX410), MK-0518, PPL-100, PRO 140, PRO 542, PRO 2000, Racivir, SCH-D (vicriviroc), SP01A, SPL7013, TAK-652, Tipranavir (Aptivus), TNX-355, TMC125 (etravirine), UC-781, UK-427,857 (Maraviroc), Valproic acid, VRX496, Zalcitabine, Valganciclovir, Clindamycin with Primaquine, Fluconazole Pastille, Nystatin Pastille, Eflornithine, Pentamidine, Isethionate, Trimethoprim, Trimethoprim/sulfa, Piritrexim, Pentamidine isethionate, Spiramycin, Intraconazole-R51211, Trimetrexate, Daunorubicin, Recombinant Human Erythropoietin, Recombinant Human Growth Hormone, Megestrol Acetate, Testosterone, Aldesleukin (Proleukin), Amphotericin B, Azithromycin (Zithromax), Calcium hydroxyapatite, Doxorubicin, Dronabinol, Entecavir, Epoetin alfa, Etoposide, Fluconazole, Isoniazid, Itraconazole (Sporanox), Megestrol, Paclitaxel (Taxol), Peginterferon alfa-2, Poly-L-lactic acid (Sculptra), Rifabutin (Mycobutin), Rifampin, Somatropin and Sulfamethoxazole/Trimethoprim. Preferred anti-HIV compounds for use in the present invention include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The term "antibody binding terminal moiety", "antibody binding terminus" or "antibody binding moiety" (ABT within the general formula of compounds according to the present invention) is used to described that portion of a bifunctional ARM-H compound according to the present invention which comprises at least one small molecule or hapten which can bind to antibodies within the patient. The term "hapten" is used to describe a small-molecular-weight inorganic or organic molecule that alone is not antigenic but which when linked to another molecule, such as a carrier protein (albumin, etc.) or in the case of the present invention, as an antibody terminus in the present compounds, is antigenic; and an antibody raised against the hapten (generally, the hapten bonded or complexed to the carrier) will react with the hapten alone. Because, in many instances, antihapten (anti-DNP) antibodies are already present in the human blood stream as endogenous antibodies because they naturally become raised to endogenous haptens (already present in patients), no pre-vaccination is necessary for ARM-H activity.

It is preferred that the antibody binding terminal comprise a hapten which is reactive with (binds to) an endogenous antibody that pre-exists in the patient prior to initiate therapy with the compounds of the present invention and does not have to be separately raised as part of a treatment regimen (for example, by vaccination or other approach for enhancing immunogenicity). Thus, haptens which comprise a di- or trinitro phenyl group as depicted below, or a digalactose hapten (Gal-Gal-Z, preferably Gal-Gal-sugar, preferably Gal-Gal-Glu), are preferred. Additionally, a compound according to the general structure:

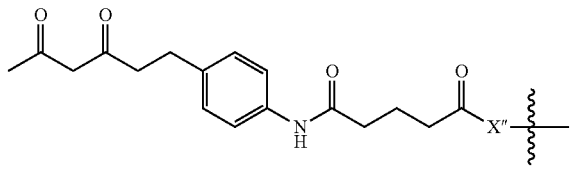

Where X" is O, $CH_2$, $NR^1$, S; and
$R^1$ is H, a $C_1$-$C_3$ alkyl group or a —$C(O)(C_1$-$C_3)$ group;
May be used as haptens in the present invention.

Further, a moiety according to the chemical structure:

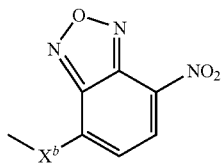

Where $X^b$ is a bond, O, $CH_2$, $NR^1$ or S may also be used as a hapten (ABT) in the present invention.

The di- or trinitro phenyl hapten (ABT) moiety for use in the present invention may be represented by the following formula:

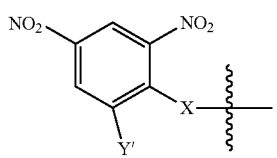

Where Y' is H or $NO_2$;
X is O, $CH_2$, $NR^1$, S(O), $S(O)_2$, —$S(O)_2O$, —$OS(O)_2$, or $OS(O)_2O$;
$R^1$ is H, a $C_1$-$C_3$ alkyl group, or a —$C(O)(C_1$-$C_3)$ group;

The (Gal-Gal-Z) hapten is represented by the chemical formula:

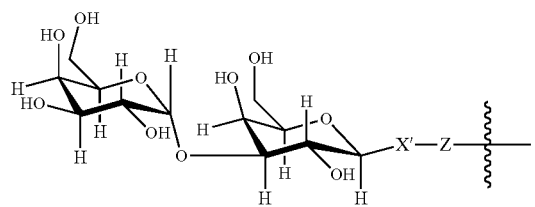

Where X' is $CH_2$, O, N—R", or S, preferably O;
$R^{1'}$ is H or $C_1$-$C_3$ alkyl; and
Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiuose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferring, ceruloplasmin, major histocompatability complex proteins (MHC), enzymes, lectins and selectins, calnexin, calreticulin, and integrin glycoprotein among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or connector molecule) or a glucose or glucosamine (especially N-acetylglucosamine).

It is noted that Z is linked to a galactose residue through a hydroxyl group or an amine group on the galactose of Gal-Gal, preferably a hydroxyl group. A preferred hapten is Gal-Gal-Glu which is represented by the structure:

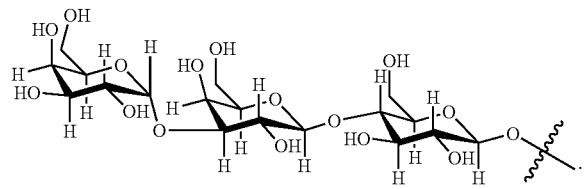

The term "pathogen binding terminus" or "pathogen binding terminal moiety" ("PBT") is use to described that portion of a difunctional ARM-H compound according to the present invention which comprises at least one small molecule or moiety which can bind specifically to is capable of binding to gp120 envelope protein on HIV virus or a cell surface of CD4 cells which are infected with HIV (HIV+) in said patient.

PBT groups (i.e., the chemical moiety connected to linkers and AB

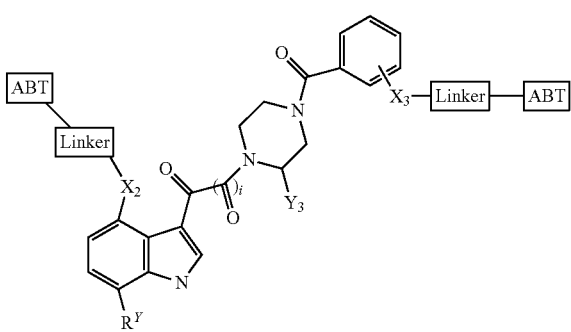

Where $X_2$ and $X_3$ are each independently a bond, H, $C_1$-$C_6$ alkyl, O—($C_1$-$C_6$ alkyl) (such that the linker and ABT are absent from the molecule at that position), O, $CH_2$, $NR^1$, S(O), $S(O)_2$, —$S(O)_2O$, —$OS(O)_2$, or $OS(O)_2O$;
$R^1$ is H or a $C_1$-$C_3$ alkyl group, preferably H;
i is 0 or 1;
$R^y$ is an aryl or heteroaryl group, preferably a phenyl, naphthyl, pyridyl (2-, 3- or 4-pyridyl group), thiazolyl (2-, 4- or 5-thiazole), isothiazolyl, oxazolyl (2-, 4- or 5-oxazole), isoxazolyl, furanyl (2- or 3-furan) or thiophenyl (2- or 3-thiophene);
$Y_3$ is H or a $C_1$-$C_3$ alkyl group (disposed out of or into the plane, preferably out of the plane on the chiral carbon to which it is attached;

Linker is a linker as otherwise disclosed herein and includes a connector (CT) which may be a bond or a chemical connector; and ABT is an antibody binding terminus as otherwise described herein (preferably a DNP group) with the proviso that at least one of $X_2$ and $X_3$ is other than H (such that the molecule contains a linker and ABT moiety), or a pharmaceutically acceptable salt, solvate or polymorph thereof.

The term "linker" refers to a chemical entity connecting an antibody binding terminus (ABT) moiety to a pathogen binding terminus (CBT) moiety, optionally through a connector moiety (CT) through covalent bonds. The linker between the two active portions of the molecule, that is the antibody binding terminus (ABT) and the pathogen binding terminus (PBT) ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5A to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 4 and 14 glycol units in length may be preferred. By having a linker with a length as otherwise disclosed herein, the ABT moiety and the PBT moiety may be situated to advantageously take advantage of the biological activity of compounds according to the present invention which bind to HIV envelope protein gp120 (gp120) and attract endogenous antibodies to the virus and/or infected cells (e.g. HIV infected CD4 cels) to which the compounds are bound, resulting in the selective and targeted death of those viruses and/or cells. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, etc.) may be favored as a linker because of the chemical and biological characteristics of these molecules. The use of polyethylene (PEG) linkages is preferred. Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, etc.).

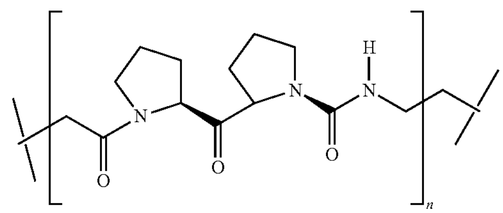

or polyproline linker 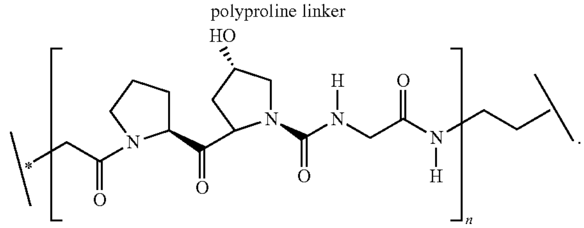 collagen linker

Preferred linkers include those according to the chemical structures:

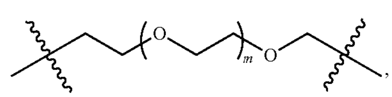

, 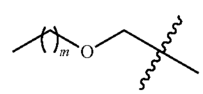 or

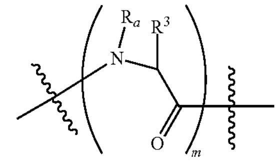

Or a polypropylene glycol or polypropylene-co-polyethylene glycol linker having between 1 and 100 glycol units;

Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units, to which is bonded a lysine group (preferably at its carboxylic acid moiety) which binds one or two DNP groups to the lysine at the amino group(s) of lysine. Still other linkers comprise amino acid residues (D or L) to which are bonded to ABT moieties, in particular, DNP, among others at various places on amino acid residue as otherwise described herein. In another embodiment, as otherwise described herein, the amino acid has anywhere from 1-15 methylene groups separating the amino group from the acid group in providing a linker to the ABT moiety.

Or another linker according to the chemical formula:

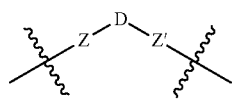

Where Z and Z' are each independently a bond, —(CH$_2$)$_i$—O, —(CH$_2$)$_i$—S, —(CH$_2$)$_i$—N—R,

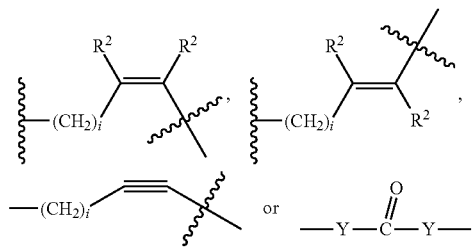

wherein said —(CH$_2$)$_i$ group, if present in Z or Z', is bonded to a connector, ABT or CBT;
Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
D is

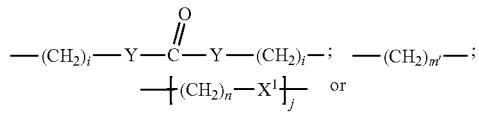

a bond, with the proviso that Z, Z' and D are not each simultaneously bonds;
j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

X$^1$ is O, S or N—R; and
R is as described above, or a pharmaceutical salt thereof.

The term "connector", symbolized in the generic formulas by [CT], is used to describe a chemical moiety which is optionally included in bifunctional compounds according to the present invention which forms from the reaction product of an activated ABT-linker with a PTB moiety (which also is preferably activated) or an ABT moiety with an activated linker-PTB as otherwise described herein. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group as otherwise described herein. It is noted also that a connector group may be linked to a number of linkers to provide multifunctionality (i.e., more than one PBT moiety and/or more than one ABT moiety within the same molecule. It is noted that there may be some overlap between the description of the connector group and the linker group, especially with respect to more common connector groups such as amide groups, oxygen (ether), sulfur (thioether) or amine linkages, urea or carbonate —OC(O)O— groups as otherwise described herein. It is further noted that a connector (or linker) may be connected to ABT, a linker or CBT at positions which are represented as being linked to another group using the using the symbol

Where two or more such groups are present in a linker or connector, any of an ABT, a linker or a PBT may be bonded to such a group.

Common connector groups which are used in the present invention include the following chemical groups:

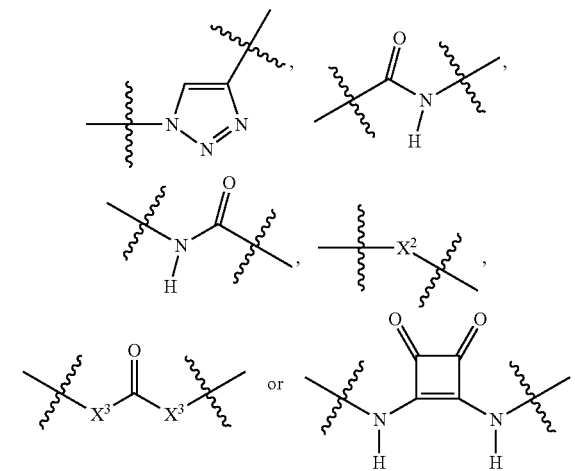

Where $X^2$ is O, S, $NR^4$, S(O), $S(O)_2$, $—S(O)_2O$, $—OS(O)_2$, or $OS(O)_2O$;
$X^3$ is O, S, $NR^4$; and
$R^4$ is H, a $C_1$-$C_3$ alkyl or alkanol group, or a $—C(O)(C_1$-$C_3)$ group.

As discussed hereinabove, it is noted that each of the above groups may be further linked to a chemical moiety which bonds two or more of the above connector groups into a multifunctional connector, thus providing complex multifunctional compounds comprising more than one ABT and/ or PBT group within the multifunctional compound. An example of such compound is the compound B-ARM-1, described herein.

Initial work by the inventors involved in identifying compound ARM-H began with the small molecule BMS-378806, (4-benzoyl-1-(2-(4-methoxy-1H-pyrrolo(2,3-b) pyridin-3-yl)-1,2-dioxoethyl)-2-methyl-, (2R)-Piperazine, CAS Number 357263-13-9, MW 406) shown here as Formula 1, a known inhibitor of the CD4-gp120 interaction. (Wang, et al. J. Med. Chem. 2003, 46, 4236-42396)

Formula 1 points toward the solvent in the complex. See Kong. R.; Tan, J.; Ma, X.; Chen, W.; Wang. C.; Biochim. Biophys. Acta 2006, 1764. 766-7728.

Thus, in accordance with the invention, Formula 1 was re-engineered to include the capability to recruit anti-DNP antibodies to gp120-expressing particles (infected cells or viruses), increasing the "visibility" of the combination to the human immune system. Consequently, an ARM-H of Formula 4 was prepared in high yield (38% overall) via azide-alkyne cycloaddition (Rostovtsev, V. V.; Green, L. G.; Fokin, V. V.; Sharpless, K. B. Angew. Chem., Int, Ed. 2002, 41, 2596-2599. Tornne, C.; Christensen, C.; Meldal, M. J. Org. Chem. 2002, 67, 3057-3064) of the compounds of Formula 2 and Formula 3, which were derived in turn from known intermediates, as will be discussed further below. Wang, T.; et al. J. Med. Chem. 2003, 46, 4236-4239.

Figures 2A, 2B:
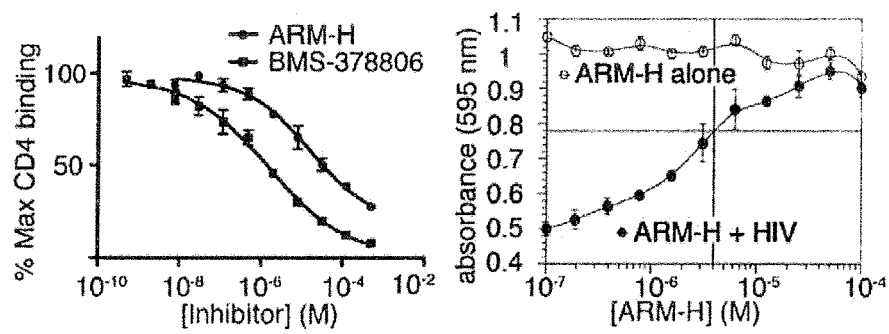
FIG. 2A shows the results of a composition ELISA monitoring binding of sCD4 to immobilized gp120.
FIG. 2B shows the results of a HIV-1 viral replication assay.

As discussed above, ARM-H compounds target HIV by inhibiting virus entry while targeting Env-expressing cells for immune recognition and clearance. (See FIG. 1) The ability of ARM-H to inhibit CD4 binding to HIV-1 gp120 was assessed first in an enzyme-linked immunosorbent assay (ELISA) (FIG. 2a). (See Ho, H.; et al. J. Virol. 2006, 80, 4017-4025). As shown in FIG. 2a, ARM-H was able to out-compete the CD4-gp120 interaction with a mean inhibitory concentration ($IC_{50}$) of about 8.7 μM, and it was only slightly less potent than the parent compound Formula 1 ($IC_{50}$=1.3 μM). Next we investigated ARM-H's ability to inhibit the entry of live HIV-1 virus into the human MT-2T-cell line (FIG. 2b, $IC_{50}$=6.4 μM). Although in this assay ARM-H once again proved to be less potent than Formula 1

Figures 3A, 3B:
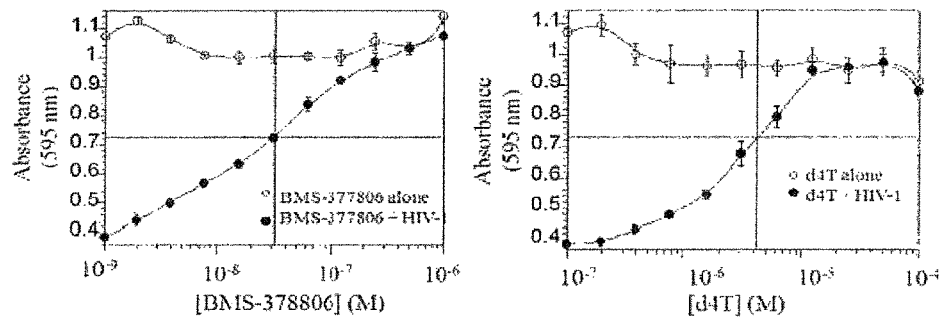
FIG. 3A shows the results of an MT-2 cell assay for HIV-1 inhibition for BMS-377806.
FIG. 3B shows the results for d4t. BMS-377806 (FIG. A) ($IC_{50}$=320 nM) and d4T (FIG. B) ($IC_{50}$=4.2 μM) HIV-1 inhibition in MT-2 cell assay. Raw absorbance data reported ±SD.

It was hypothesized that it might be possible to derivatize Formula 1, at the carbon atom of the C4 methoxy group, in which the carbon atom of the C4 methoxy group could be replaced with various bulky substituents, (Wang, J, S.; Le, N.; Heredia, A.: Song, H. J.: Redfield, R.: Wang, L. X. Org. Biomol. Chem. 2005, 3, 1781-1786) so as to provide a linker which would attract DNP without sacrificing the compound's ability to inhibit viral entry. This hypothesis was supported by an analysis of a published computational docking model suggesting that the C4 methoxy group in ($IC_{50}$=0.32 µM; FIG. 3a), it demonstrated potency equivalent to that of d4T, which is currently a mainstay in HIV pharmacotherapy ($IC_{50}$=4.2 µM; FIG. 3b).

It should be noted that the increase in potency of Formula 1 in MT-2 cells versus ELISAs may be the result of a cooperative enhancement in binding to viral envelope gp120, which exists as a trimer, noting that the ELISA studies were performed using monomeric gp120. The steric bulk of ARM-H due to the C4 tether may impede binding of more than one ARM-H molecule per gp120 trimer. Notably, however, ARM-H demonstrated no observable cytotoxicity in control MT-2 cultures lacking HIV virus (FIG. 2b, white circles).

It was confirmed that ARM-H has the ability to recruit antibodies to gp120 both in vitro and in tissue culture. Initial ELISA experiments (FIGS. 4a, 4b) demonstrated a concentration-dependent increase in anti-DNP antibody binding to the ARM-H-gp120 complex but not to gp120 alone. Thus, ARM-H is capable of templating a ternary complex that also includes gp120 and anti-DNP antibody.

It was also confirmed that this ternary association could form in a complex cellular milieu, and that ARM-H has the ability to recruit AlexaFluor 488-labeled anti-DNP antibodies to HIV-Env-expressing Chinese hamster ovary cells (CHO-gp120 cells) by immunofluorescence microscopy (See Weiss. C.; White, J. J Viral. 1993, 67, 7060-7066).

Figures 1, 5A:
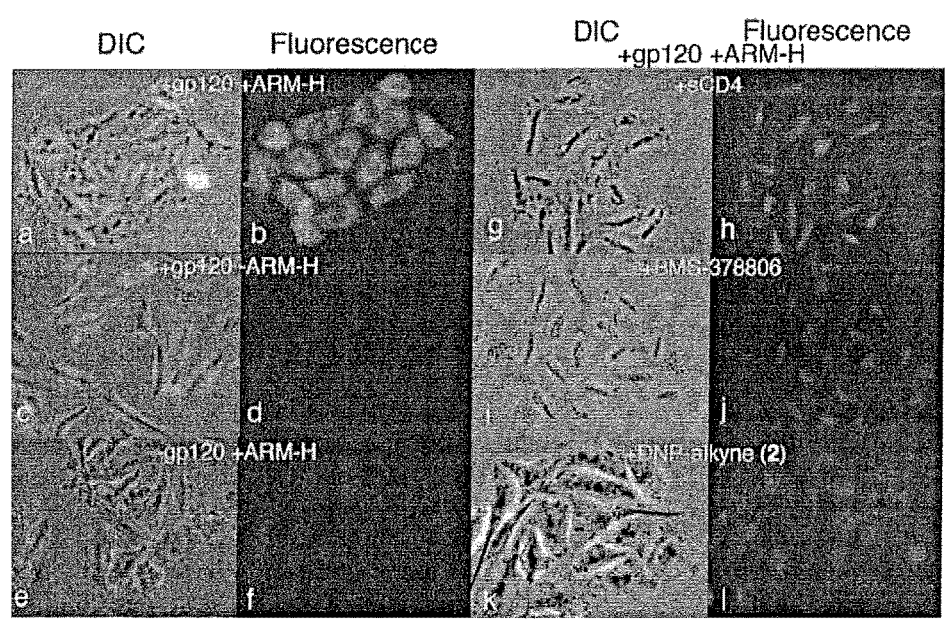

A strong fluorescence signal was observed when CHO-gp120 cells were incubated with ARM-H and labeled anti-DNP antibodies (FIG. 5a, 5b). Because it was necessary to permeabilize the cells prior to labeling, intracellular gp120 can also be observed in these micrographs. This fluorescence was absent from both CHO-gp120 cells not treated with ARM-H (FIG. 5c, 5d) and CHO cells not coding for HIV-env gene expression (CHO-WT cells, FIG. 5e, 5f). Furthermore, the intense fluorescence observed in FIG. 5b was considerably diminished in the presence of the competing ligands soluble CD4 (sCD4, FIG. 6g, 6h), Formula 1 (FIG. 5i, 5j), and a DNP-containing alkyne that lacks the gp120-binding motif (Formula 2, FIG. 5k, 5l).

Figure 6:
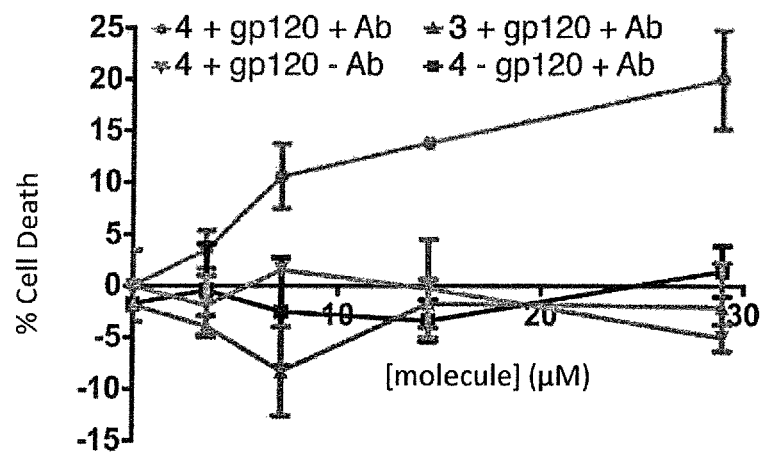
FIG. 6 shows the ARM-H mediated killing of live HIV-Env expressing CHO cells.

Taken together, these results provide strong evidence that ARM-H is capable of recruiting anti-hapten (e.g. anti-DNP) antibodies to cells expressing the Env glycoprotein in a fashion that depends upon its simultaneous binding to both gp120 and anti-DNP antibodies. Finally, the present inventors confirmed that the ternary complex formed from anti-DNP antibody, ARM-H, and alive Env-expressing cell activates complement proteins and mediates cellular death. Complement proteins are known to lyse cells by forming pores in lipid membranes and have been shown to play a critical role in inactivating HIV in humans. (See Aasa-Chapman. M. M. I.; Holuigue, S.; Aubin, K.; Wong, M.; Jones, N. A.; Cornforth. D.; Pellegrino, P.; Newton. P.; Williams. 1.: Borrow, P.; Mcknight, A. J. Virol. 2005, 79, 2823-2830; Gerencer. M.; Burek, V.; Crowe, B. A.; Barrett, N. P.; Dorner, F. Microb. Pathog. 1998, 25, 253-266. Thus, rabbit complement proteins were added to CHO-gp120 cells in the presence of ARM-H and a fixed concentration anti-DNP antibodies (FIG. 6). Substantial cell killing that exhibited a significant dependence on the ARM-H concentration (data in red) was observed.

The modest levels of complement-dependent cytotoxicity observed for ARM-H in FIG. 6 are similar to values reported in other systems (see Perdomo, M. F.: Levi. M.; Ilberg, M. S.; Vahlne, A. Proc. Natl. Acad. Sci. U.S.A. 2008, 105, 6) and may result from the low levels of Env expression on the CHO-gp120 cells (see Weiss. C.; White, J. J Viral. 1993, 67, 7060-7066). Also, because of assay incompatibilities, CDC data corresponding to ARM-H concentrations greater than 30 µM could not be obtained.

Characteristic autoinhibition of ternary complex formation at high levels of bifunctional molecule, arising from excess free bifunctional material that drives the equilibria toward formation of binary complexes, was not reliably observed in these assays. For more information on autoinhibitory behavior in ternary complexes, see: Mack, E. T.; Perez-Castillejos, R.; Suo, Z.; Whitesides, G. M. Anal. Chem. 2008, 80, 5550-5555. and references contained therein.

Notably, in the absence of anti-DNP antibody and complement-preserved serum (data in green), in cells lacking the Env glycoprotein (CHO-WT, data in black), or in the presence of the compound of Formula 3, which lacks the DNP group (data in blue), no cell death was observed, suggesting that termolecular complex formation is necessary for complement-dependent cytotoxicity (CDC) and that ARM-H itself is not toxic to cells.

Positive control experiments in which cells were directly labeled with 2, 4-dinitrobenzene-sulfonic acid (FIG. 7) were found to yield levels of CDC comparable to those observed for ARM-H, providing a bench-mark for the assay results depicted in FIG. 6. Thus, ARM-H is capable of recruiting a functional complement-dependent cytotoxic response against Env-expressing cells. Thus, it was confirmed that the inventive bifunctional molecule ARM-H can both recruit anti-DNP antibodies to gp120-expressing cells and inhibit the gp120-CD4 interaction.

Data supporting these conclusions include the following: (1) ARM-H binds to gp120 competitively with CD4 and decreases viral infectivity in an MT-2 cell assay. (2) The ARM-H molecule can guide the formation of a ternary complex that includes anti-DNP antibodies and Env-expressing cells. (3) Antibodies present in this ternary complex can promote the complement-mediated killing of Env-expressing cells.

Critically, no non specific cytotoxicity was observed in either MT-2 or CHO cell lines in response to ARM-H. Also, ARM-H-mediated inhibition of HIV entry and CDC activity were both operative at concentrations ranging from 6 to 30 µM, confirming that ARM-H could function simultaneously through dual mechanisms under therapeutic conditions.

The present invention takes a novel approach and is directed to the development of compositions which recruit anti-DNP antibodies and other anti-hapten antibodies, endogenous in most patients, to HIV via binding to the gp120 envelope protein, which additionally prevents HIV from binding to CD4 and T4 cells, providing a new therapy for treating HIV infection and the symptoms associated therewith.

The following detailed description outlines the design and synthesis of a new class of small-molecules capable of redirecting endogenous anti-hapten antibodies, especially including anti-dinitrophenyl (DNP) antibodies selectively to HIV, and inducing antibody-directed, cell-mediated cytotoxicity.

Treatment of Formula 1 with azido alcohol (2) gave rise to an intermediate azide (3) following N-oxide reduction. This compound was then conjugated to known DNP-PEG conjugate (4) to provide ARM-H-1 (6).

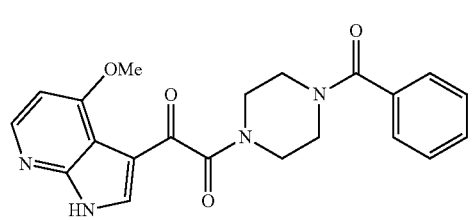
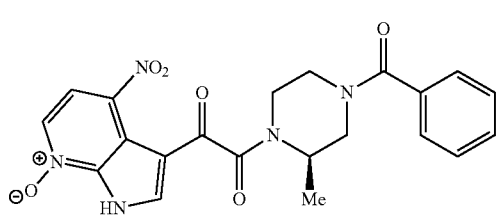
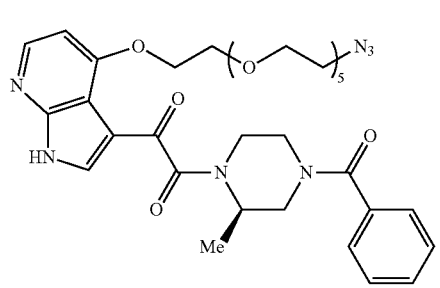
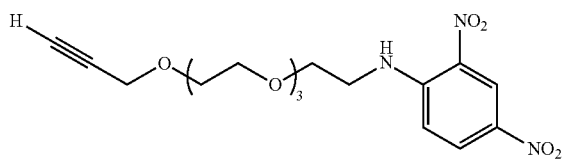
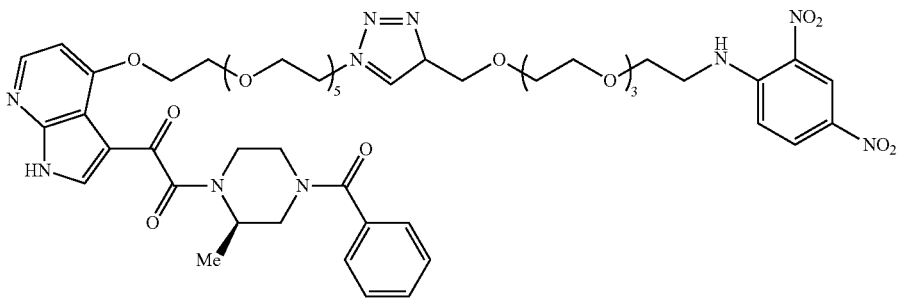
BMS-378806 (1) is prepared according to the scheme which is presented hereinbelow. It is used to prepare a number of bifunctional compounds according to the present invention.
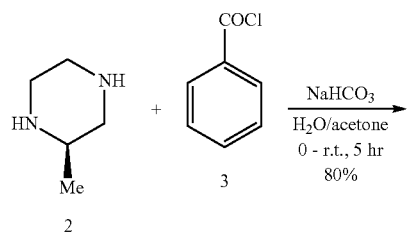
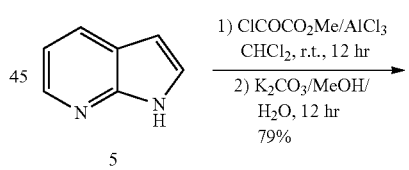
-continued
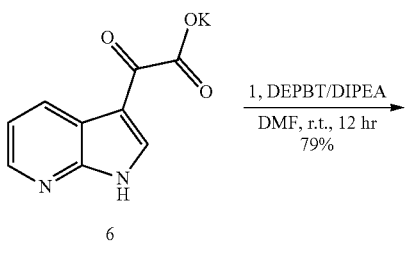
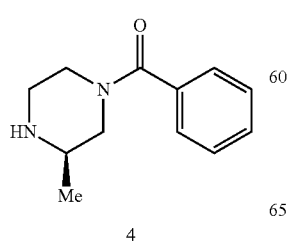

29
-continued

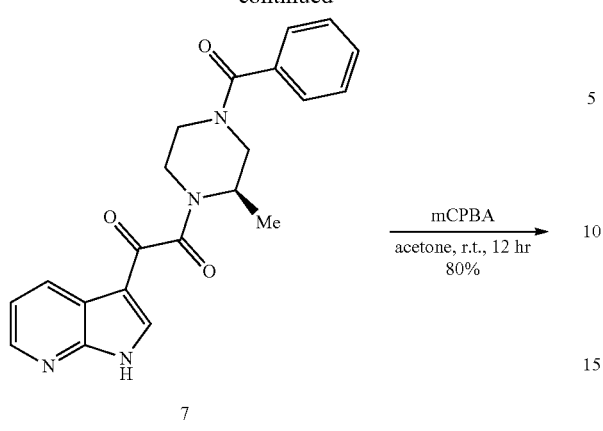

7

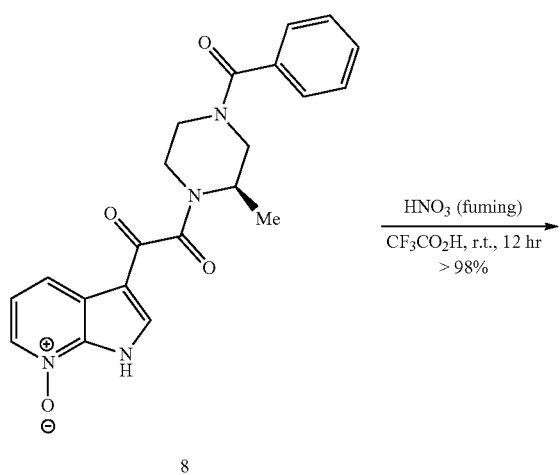

8

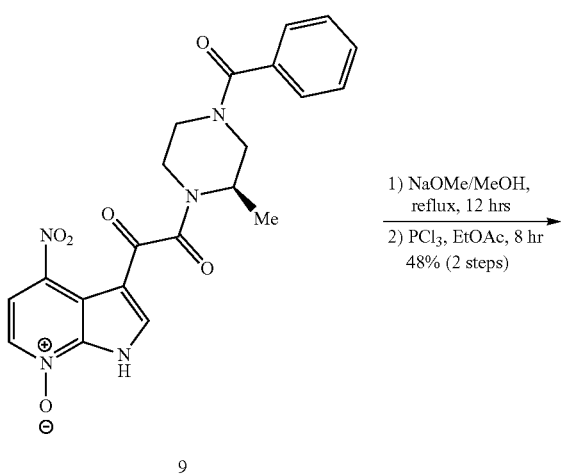

9

30
-continued

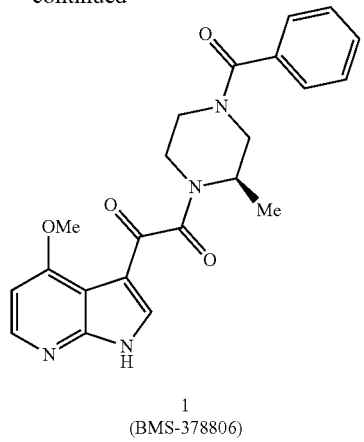

1
(BMS-378806)

Various analogs were also synthesized, specifically exemplary compounds of the invention which include alternative ABT substituents include but are not limited to ARM-H-1, ARM-H-2 and ARM-H-3, and B ARM-1, illustrated in the following syntheses. In the following synthetic scheme, PBT (in this case BMS-378806) is derivatized with a linker containing an azide group which can form a connector molecule in subsequent reactions. Once the derivatives PBT molecule is formed, bifunctional compounds according to the present invention may be condensed with appropriate ABT-containing molecules to produce the final bifunctional compounds according to the present invention.

Compound 14, a PBT containing molecule, contains a linker molecule to which is attached an azide which, when condensed with an acetylenic group as is presented in the synthetic scheme below can form a 1,2,3-triazole connector molecule to which is linked an ABT group.

In the next scheme, the introduction of a ABT moiety onto the PBT containing molecule to form a bifunctional molecule is exemplified. In this synthesis, the ABT moiety contains a linker which also contains an acetylenic moiety at its distil end, which is capable of reacting with the azido group on the PBT containing molecule to form a trialzole connector molecule in forming the bifunctional compounds according to the present invention.

In the following schemes, alternative bifunctional compounds according to the present invention are provided. These compounds containing a single PBT moiety to which is linked a compound which comprises two ABT groups, using lysine as a means to link more than one ABT group to the PBT moiety.

Derivativization: ABT Construction and Final Assembly

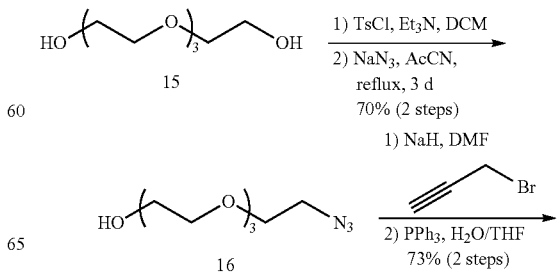

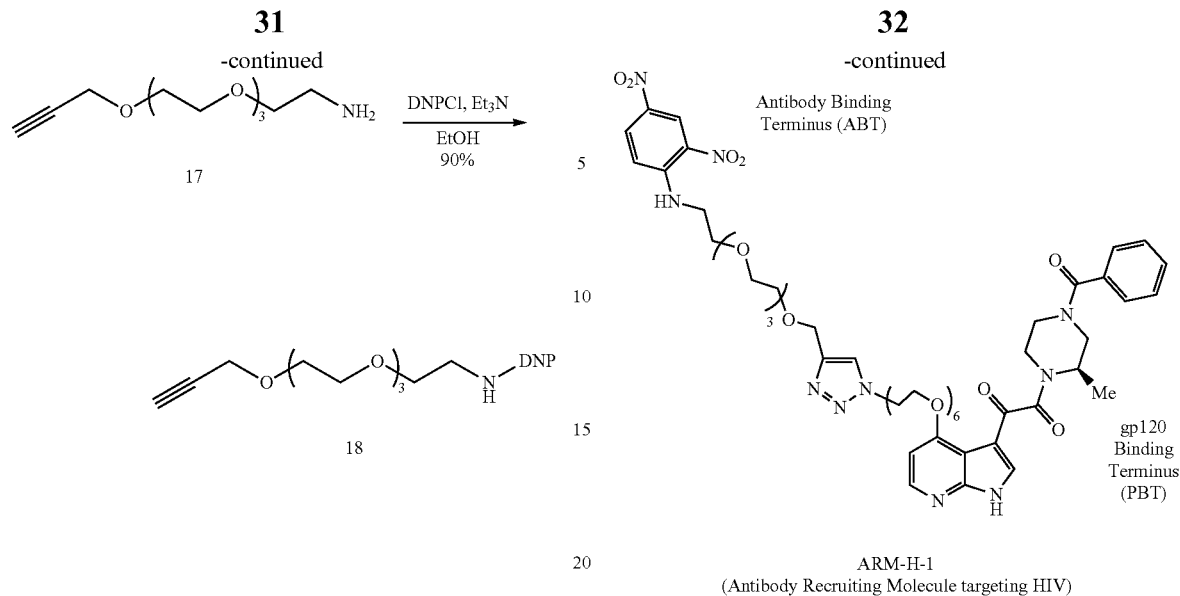

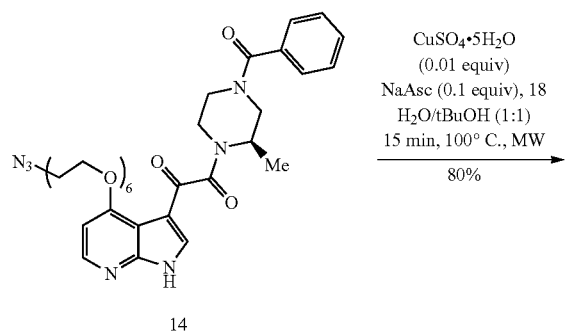

-continued

17

18

14

-continued

ARM-H-1
(Antibody Recruiting Molecule targeting HIV)

In addition to the bifunctional compounds B-ARM-1, ARM-H-1 and ARM-H-2 presented in the above schemes, more complex versions of the bifunctional compound according to the present invention such as B-ARM-1 below, which contains two pathogen binding termini (PTB) molecules and one antibody binding terminus (ABT) are presented herein. In this aspect of the invention, the connector molecular (CT) is a multifunctional compound to which more than two linker molecules and correspondingly, more than two PTB and/or ABT molecules may be bound. Note that the multifunctional connector molecule contains several triazolyl moieties through which a number of linker molecules are attached thus, providing two PBT moieties and an ABT moiety in a single molecule.

Bi-functional Molecule Synthesis: ARM Analogs

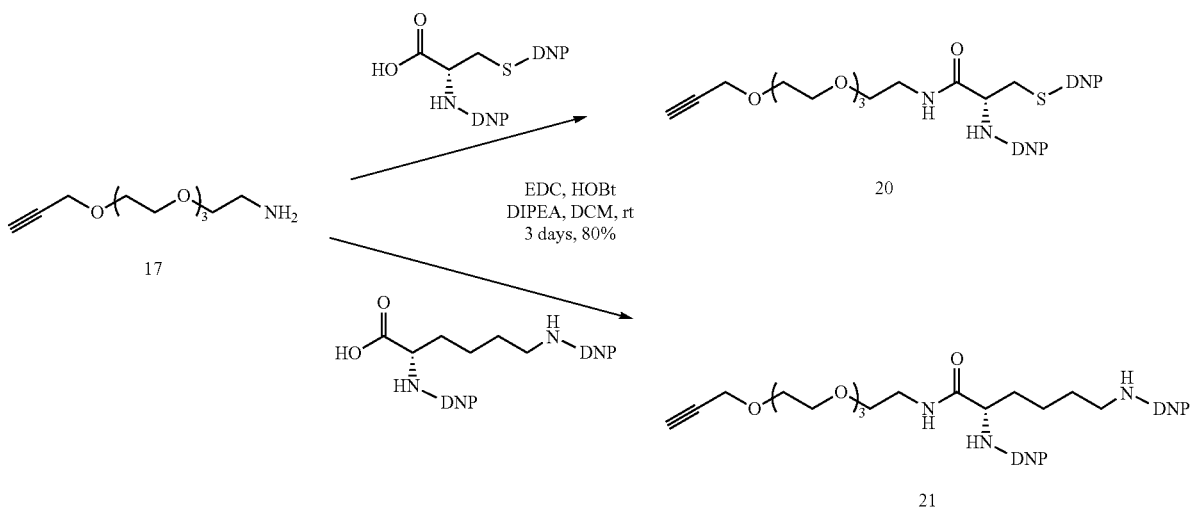

17

20

21

In collaboration with Cailtin Sengelaub

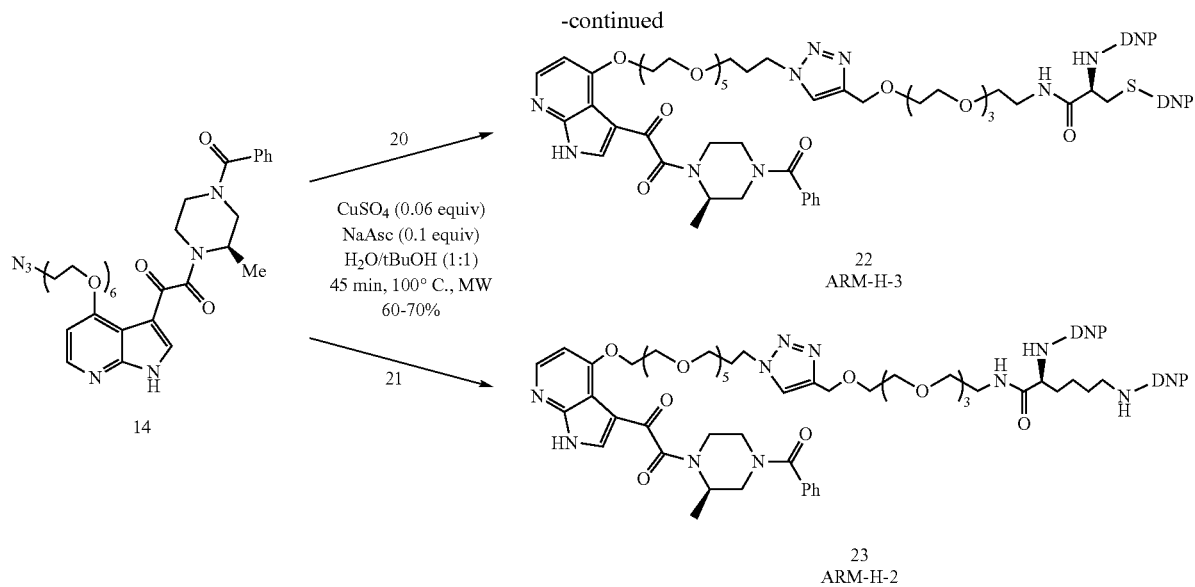

With reference to the use of alternative PBT moieties the following chemical synthetic schemes are provided. In this first scheme, the ABT (DNP) containing compound is derivatived to produce a tosyl group at the distil end of the (poly)ethylene glycol linker and an azido group at the other end of the linker to provide compound 9. Compound 28 is provided containing the ABT group (DNP). Compound 9 is condensed onto the PBT moiety compound 10 to provide compound 12 which is reacted with compound 12 to produce compound 13 which can be reacted with furan to produce compound 14. In an alternative scheme, compound 11 is reacted with compound 30 to produce ABT (DNP) containing compound 40, which can be reacted with furan or another aryl moiety (furan, pyridine, thiophene, oxazole, thiazole, benzene, naphthylene, etc.) to produce compound 28.

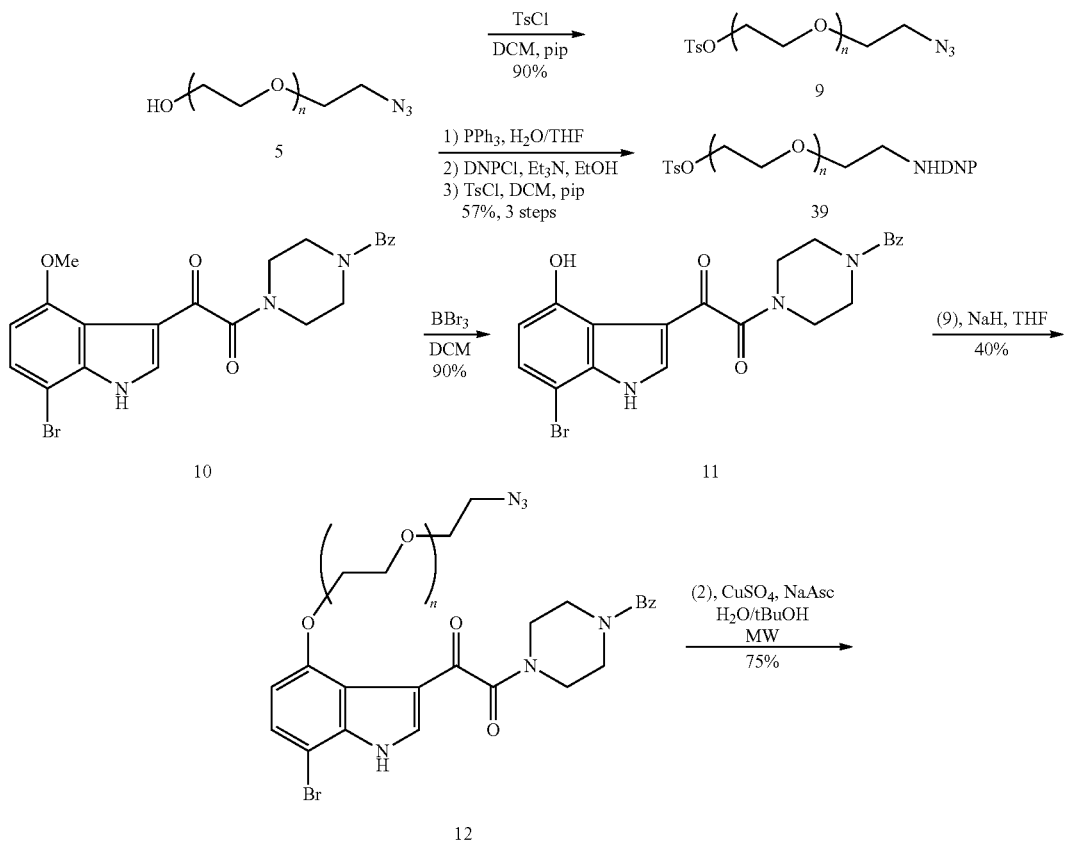

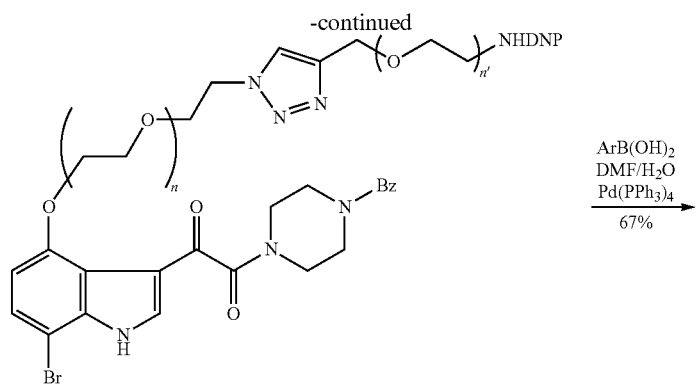
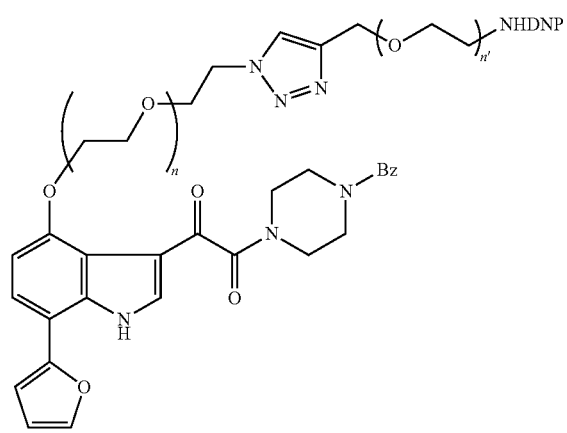
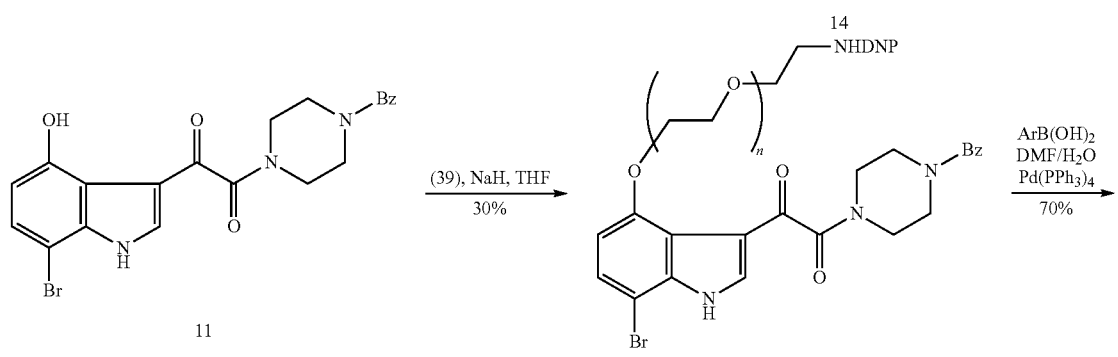
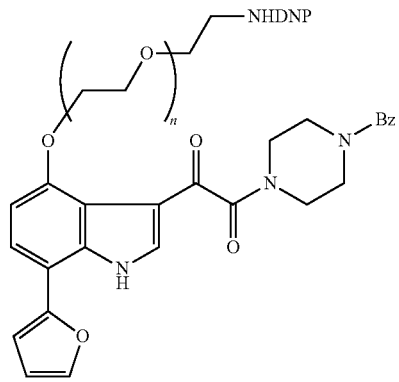

In the reaction scheme below, an alternative bifunctional compound is provided wherein the ABT moiety is introduced on the benzoyl portion of the molecule, rather than on the indole moiety, in order to provide biofunctionality and is further derivatived to introduce an aryl or heteroaryl group in place of the bromine in the indole portion of the molecule as presented hereinbelow.

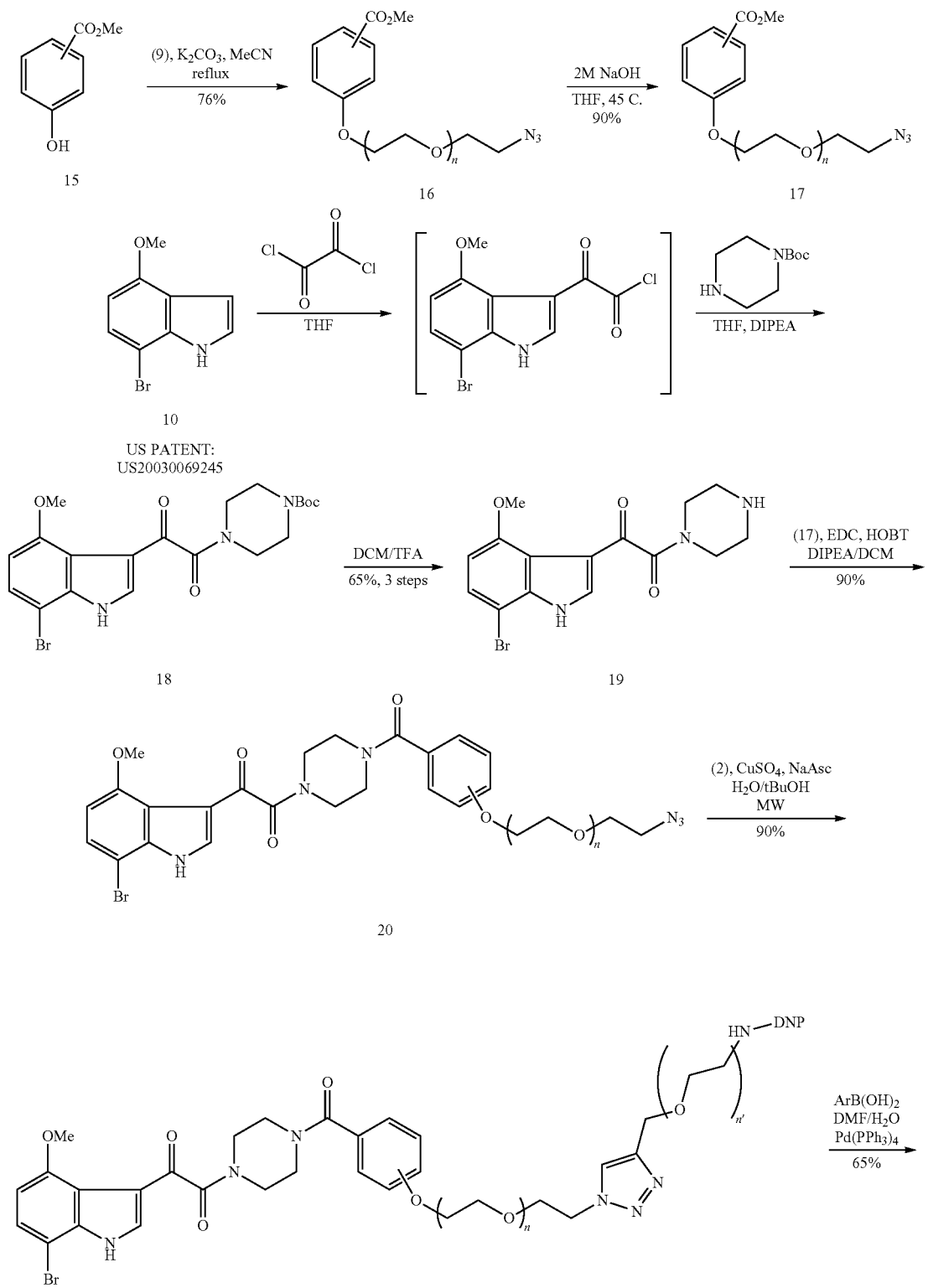

-continued
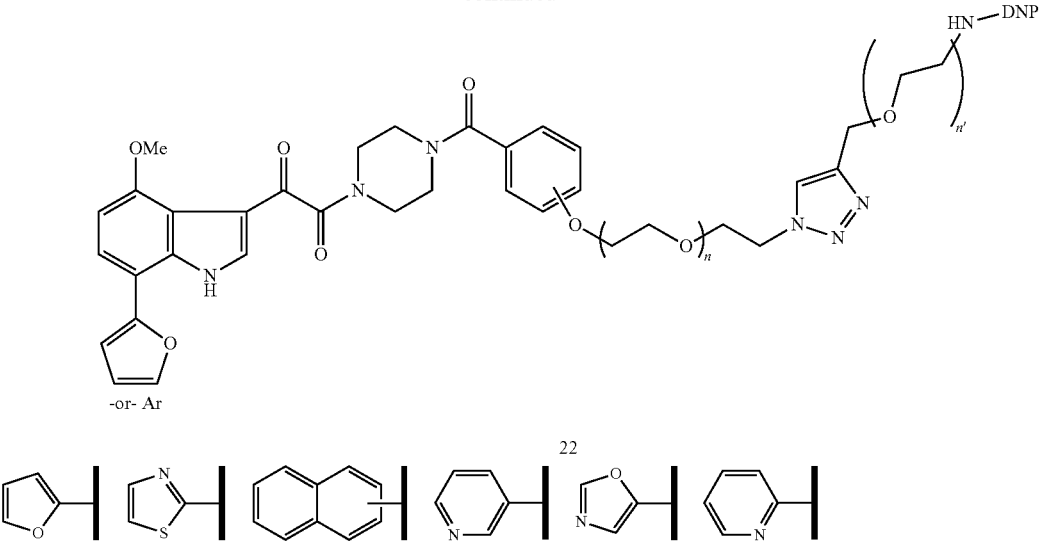
In a modification of the above synthesis, the ABT moiety may be introduced onto the PBT moiety directly through a linker without reliance on a connector to link two separate linkers as described above.
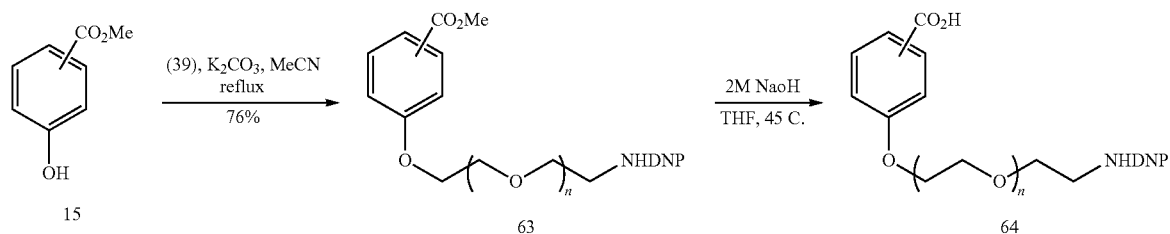
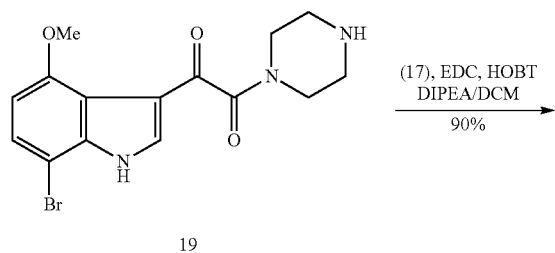
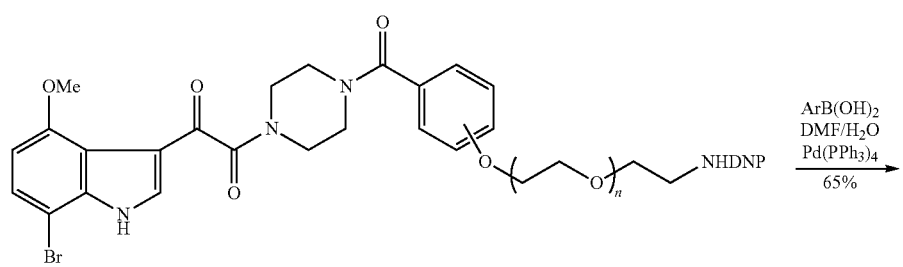

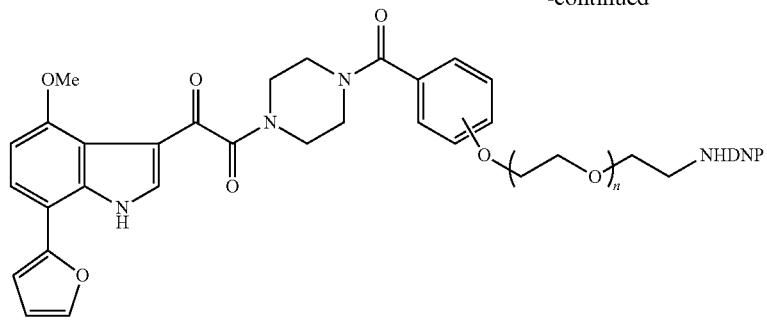
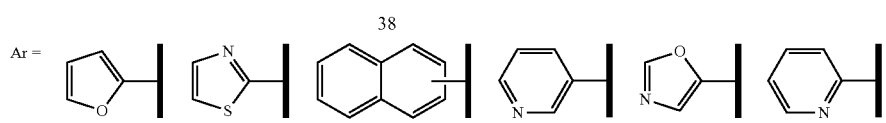
In yet another synthesis according to the present invention, the alternative PBT moiety may contain a single carbonyl, rather than the dicarbonyl moiety typically found attached to the indole, linking the piperazine group to the indole. The resulting compound 26 links the ABT moiety through the benzoyl portion of the molecule.
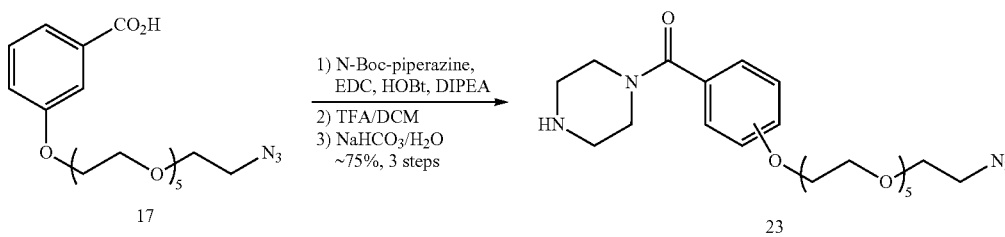
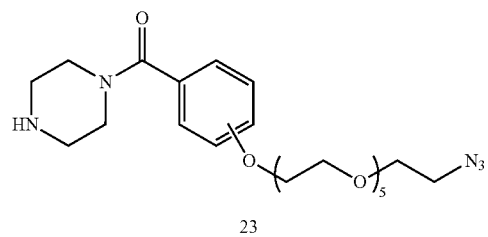
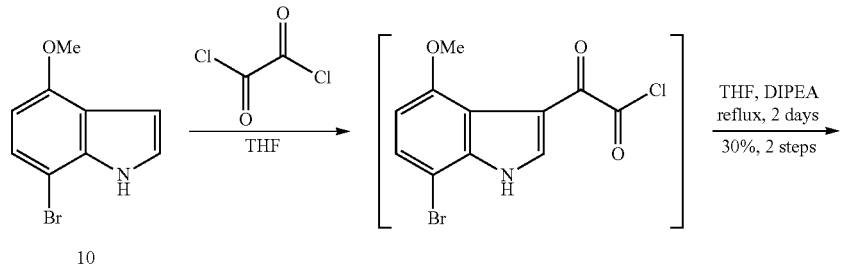
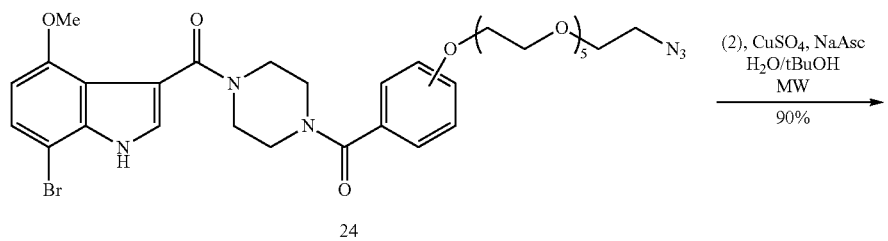
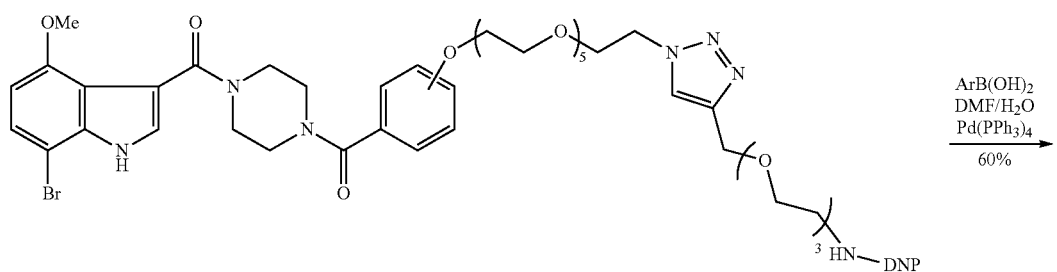

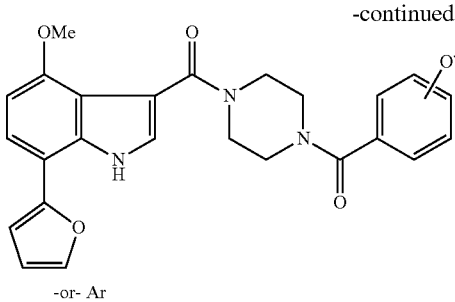
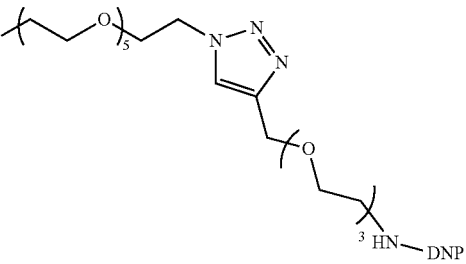

-or- Ar

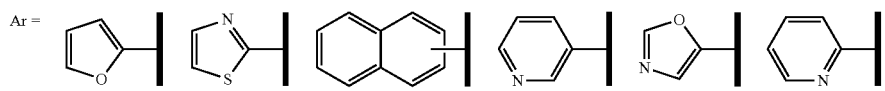

In another general synthetic route to ARM-H analogs of the type (38), which do not contain a connecting functionality (CT) attached to the linker (i.e., CT is a bond), introduction of the linker-ABT moiety as in compounds 63 and 64 is provided and the carboxylic acid compound 64, which contains the linker-ABT without a connector moiety, is then condensed onto the secondary amine (piperidine moiety) of compound 19 to produce compound 65. An aryl group as indicated is introduced onto the carbon atom containing the bromine of compound 65 to provide compound 38 and related compounds as indicated in the scheme.

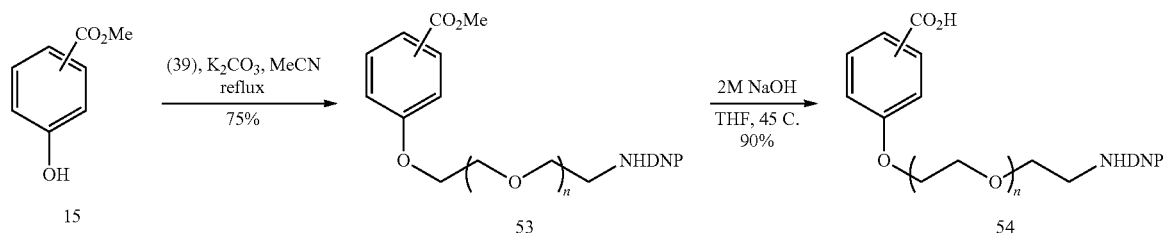

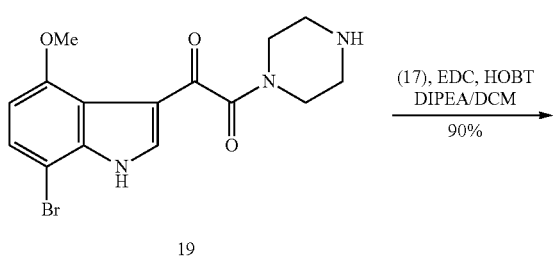

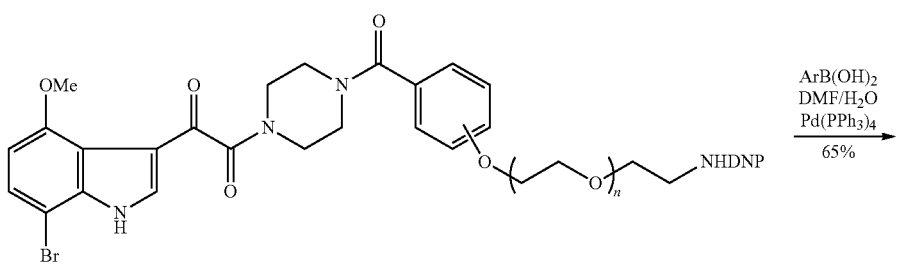

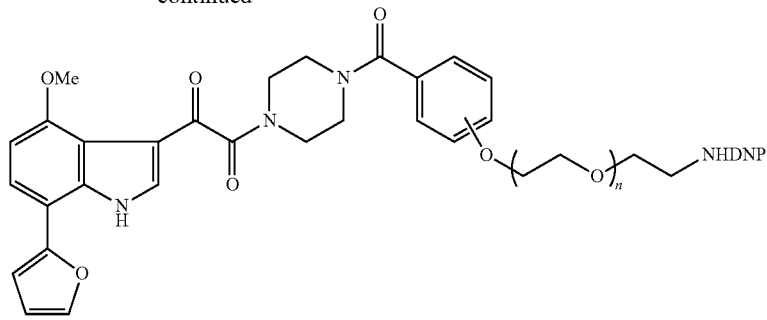
20
In the following exemplary schemes, an ABT moiety comprising DNP is linked to a PBT moiety using an amino acid DNP (dinitrophenyl) moieties. The first scheme relates to the introduction of DNP amino acids into ARM-H difunctional compounds through the indole moiety of the PBT portion of the molecule using a connector moiety as indicated.
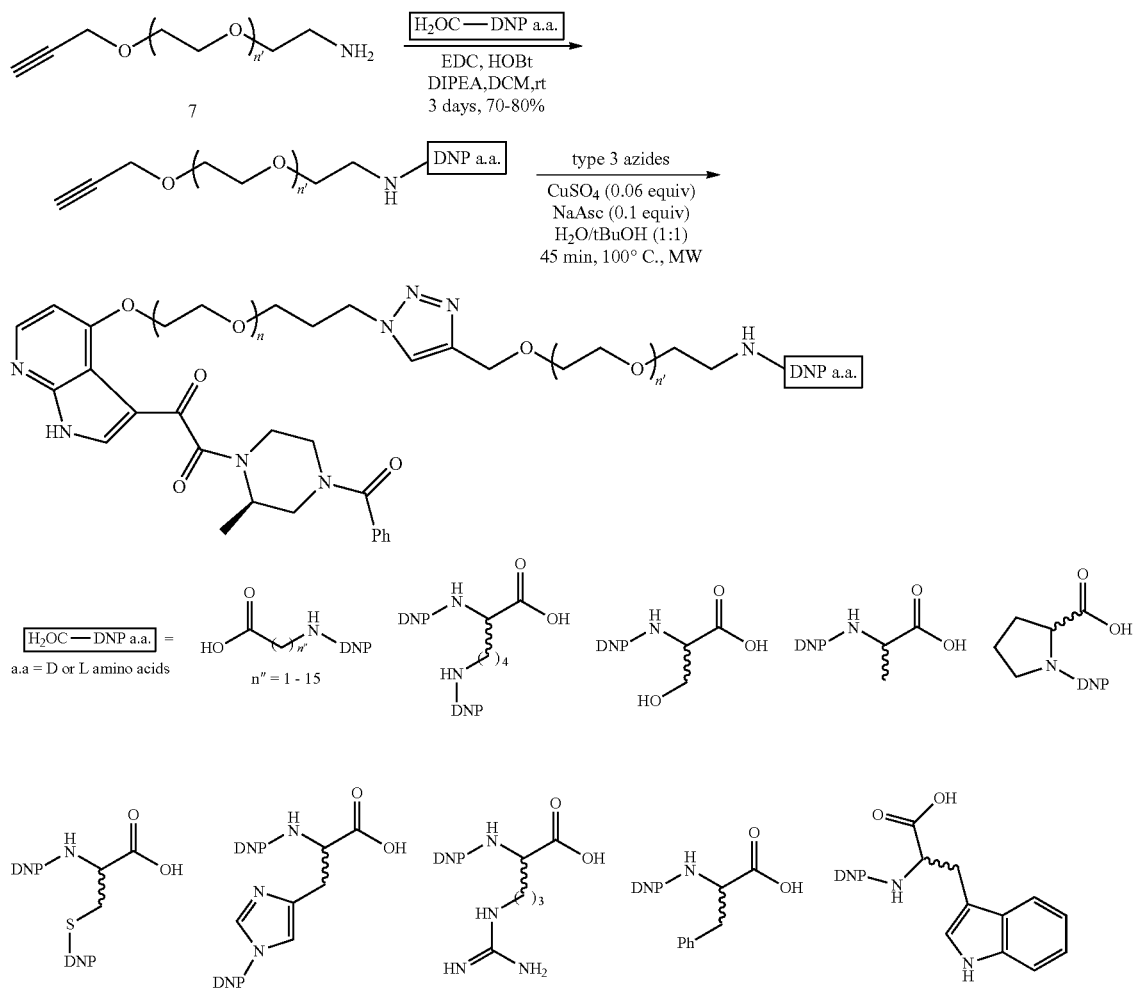

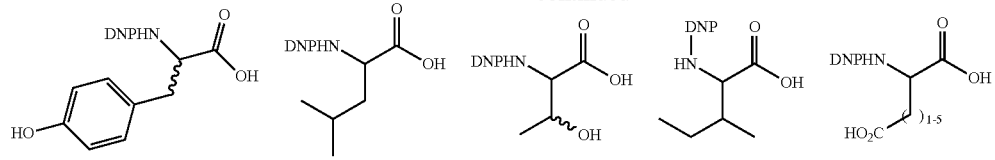
In the following alternative synthetic approach, a general synthetic route is described to provide DNP amino acid containing ARM-H molecules functionalized at the phenyl position of the molecule.
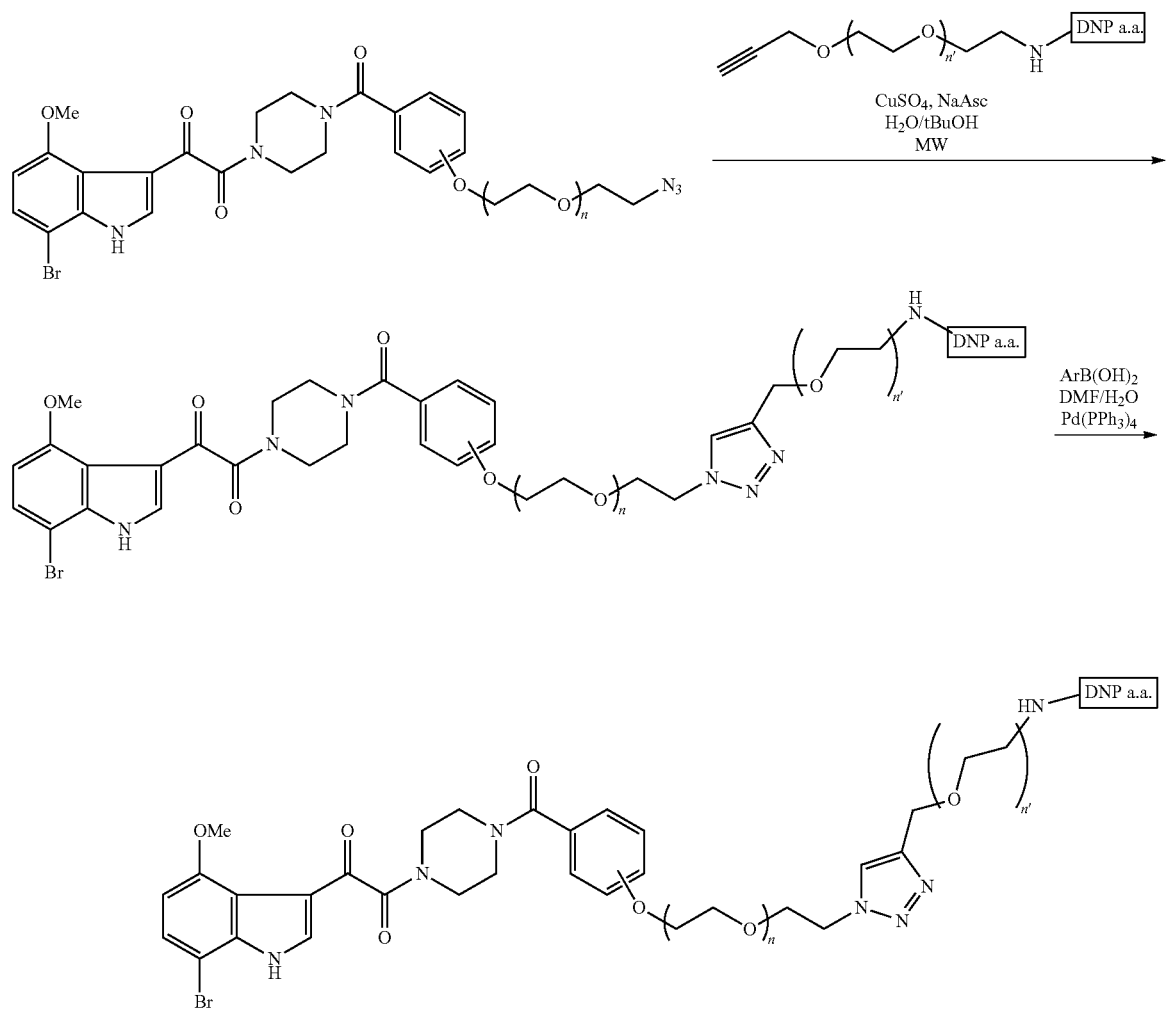
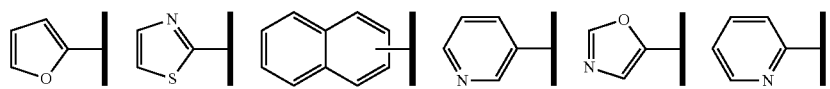
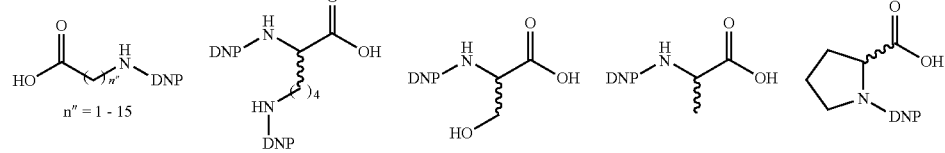

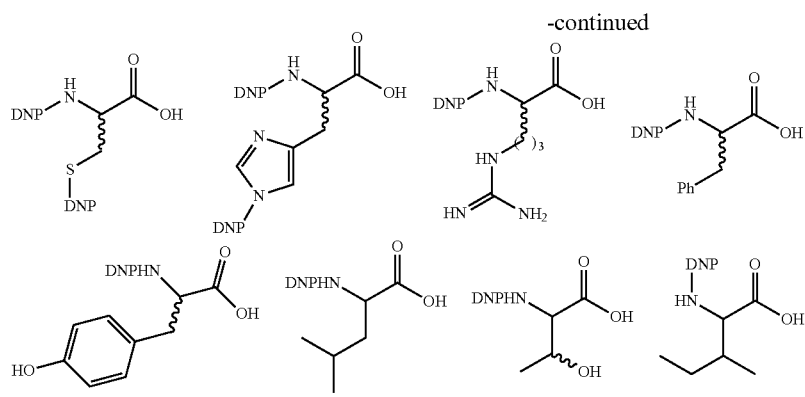
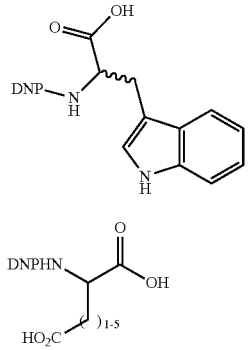

Still other difunctional compounds introduce the DNP amino acids into the phenyl (benzoyl) portion of the molecule without using a connector molecule using analogous methods described herein, in contrast to the method described above.

limitating in setting forth teachings which provide compounds according to the present invention.

Figure 10:
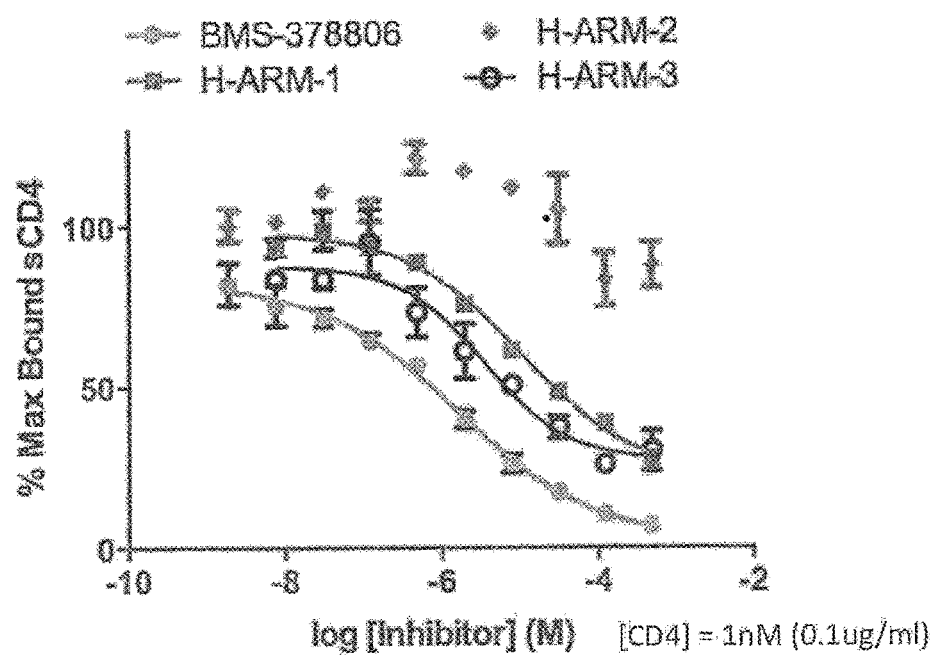
FIG. 10 shows the results of an ELISA for the various ARM-H analog compounds discussed herein.

Turning to biological data of ARM-H compounds according to the present invention, with reference to FIG. 10, this shows the results of an ELISA confirming that the various

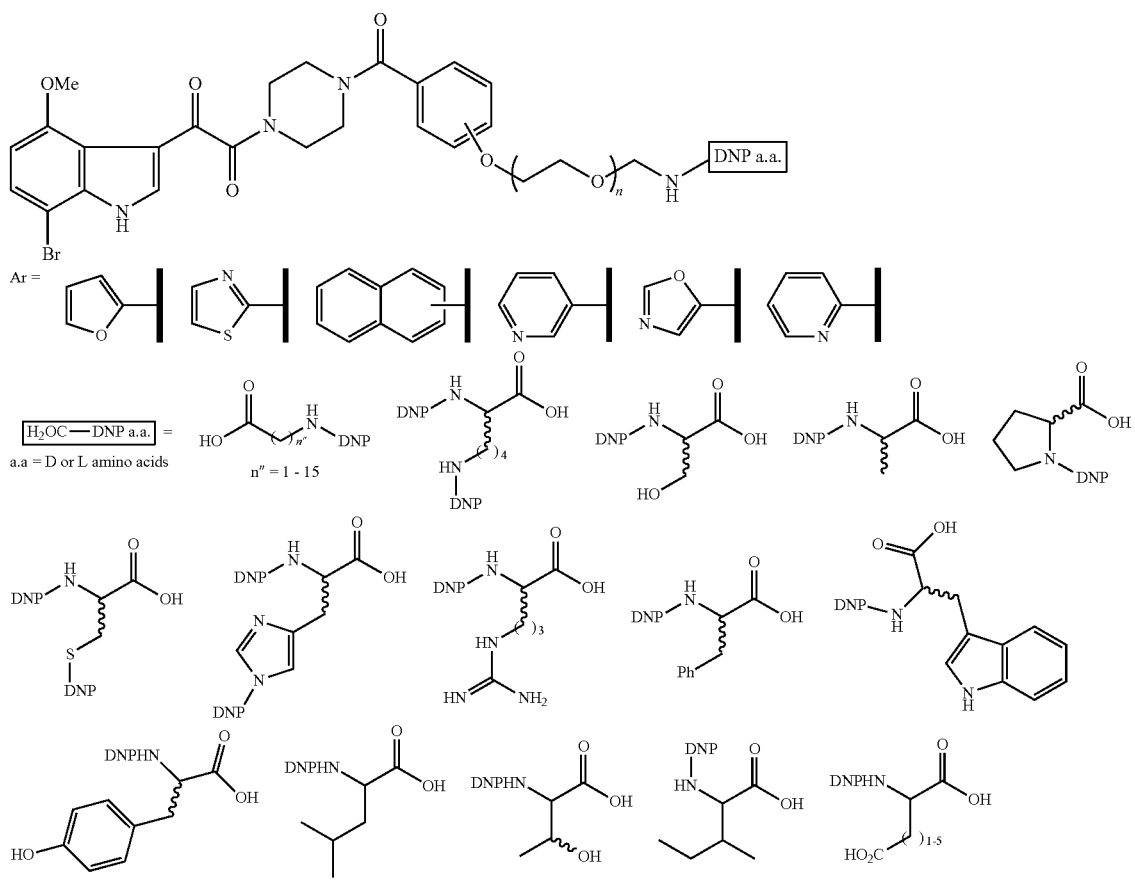

The above schemes provide exemplary synthesis of compounds according to the present invention with various iterations of same provided by analogy using well known methods as described herein and as understood by those of ordinary skill in the art. It is noted that the experimental section provides significant detail to allow the facile synthesis of a variety of ARM-H molecules as otherwise described herein. The schemes are not to be considered ARM analog compounds illustrated above inhibit the gp120-CD4 interaction. Subsequent experiments using BMS-378806 instead of sCD4 have confirmed that ARM-H-2 and ARM-H-3 cannot be out competed at BMS concentrations up to 1 mM, though ARM-H-1 can be.

Figure 11:
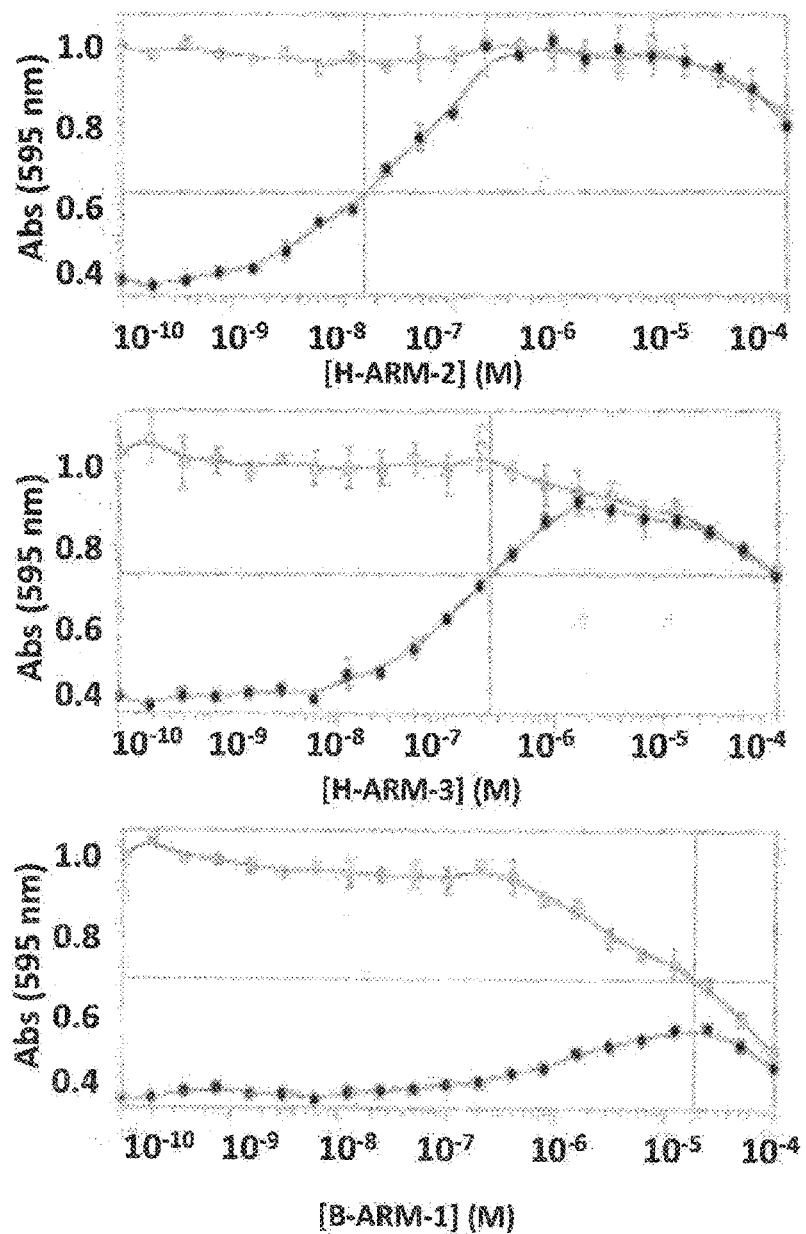
FIG. 11 illustrates the results of MT-2 cell assay for the various ARM-H analogs discussed herein.

FIG. 11 illustrates the results of MT-2 assay to illustrate the analog ARM-H activity.

Figure 12A:
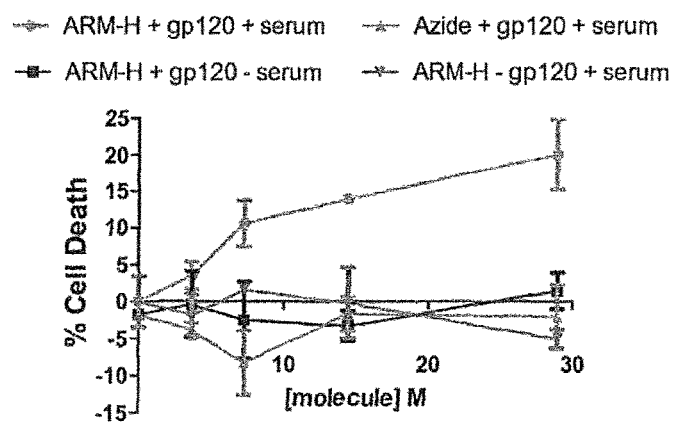
FIG. 12A illustrates the recruitment of an immune response showing the complement dependent cytotoxicity (CDC) of the analogs.
Figure 12B:
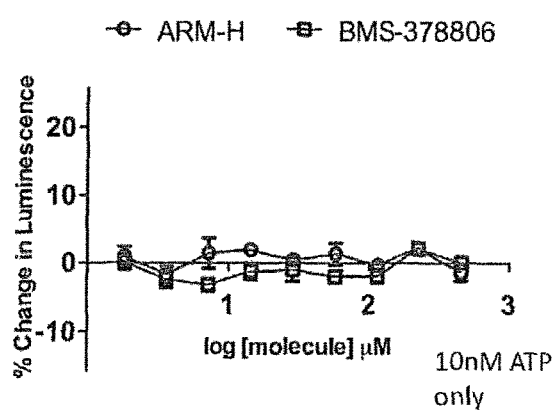
FIG. 12B illustrating the CDC for ARM-H.

FIG. 12a illustrates the recruitment of an immune response showing the complement dependent cytotoxicity (CDC) of the above analogs, FIG. 12b illustrating the CDC for ARM-H. The targeted cytotoxicity is dependent on ARM-H, gp120, DNP and antibody/serum.

Figure 13:
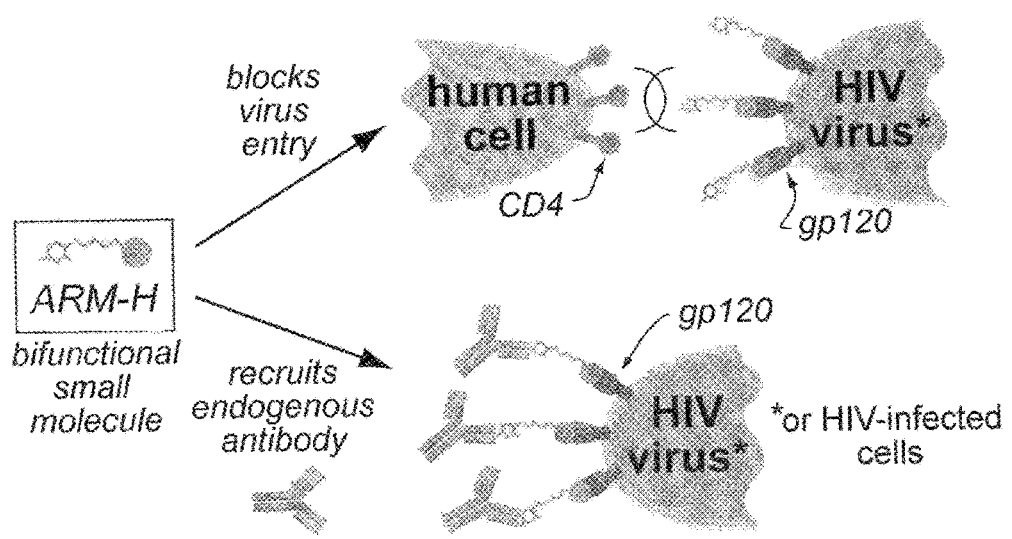
FIG. 13 illustrates the dual mechanisms of action exhibited by the bifunctional molecules of the present invention.
Figure 14:
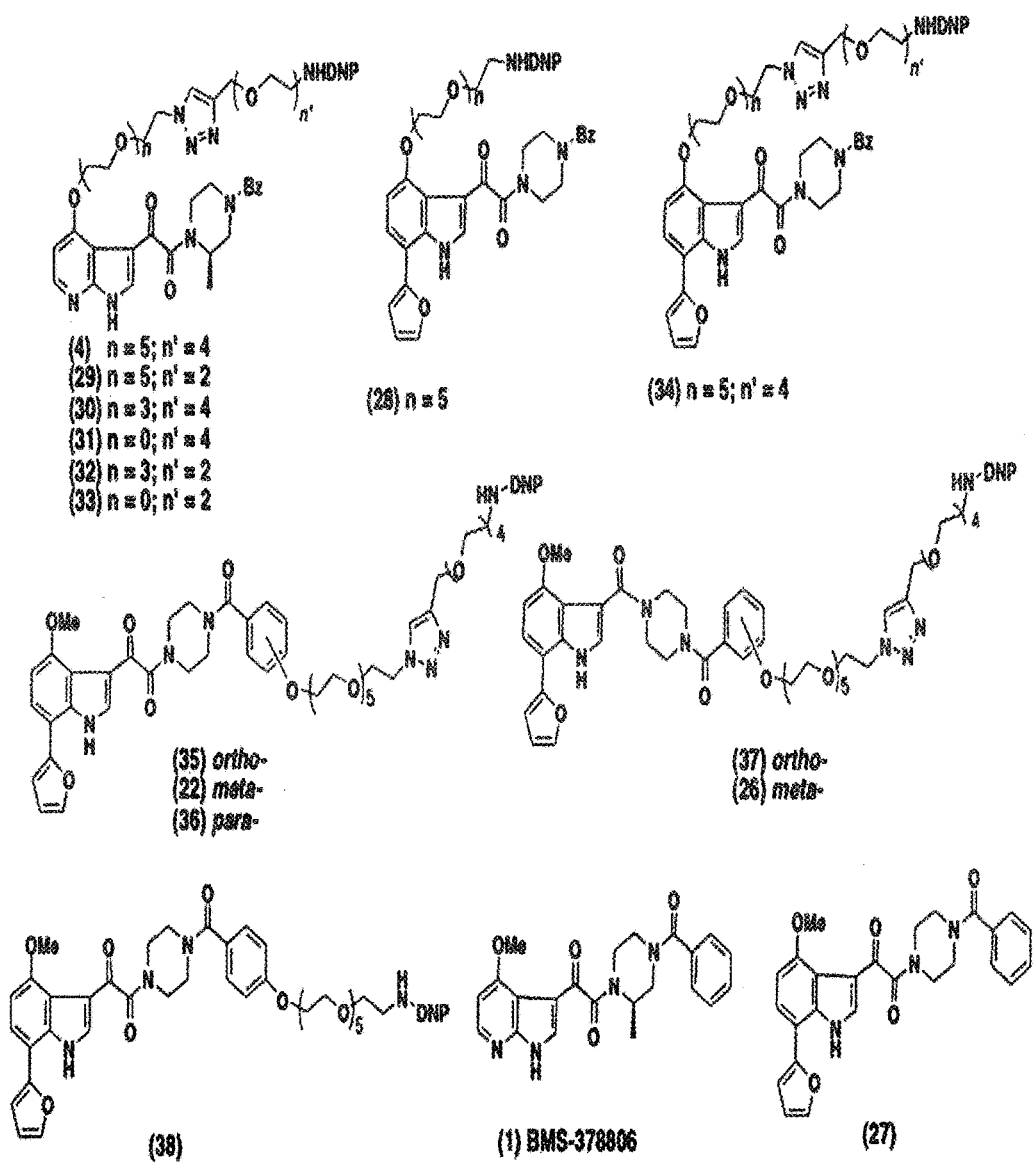
FIG. 14 shows representative bifunctional compounds according to the present invention and/or precursors which can be used to synthesize bifunctional compounds according to the present invention.

FIG. 13 illustrates the dual mechanisms of action in fighting HIV achieved with the bifunctional molecules of the present invention.

While specific analogs have been shown and described, the present invention is not limited to these specific analogs and other antibody recruiting compounds that can function as the antibody recruiting terminus connected by a linker to a binding terminus that will bind to the HIV glycoprotein gp120 (gp120 on the viral membrane as well as gp120 displayed on infected cells), would fall within the scope of the present invention. All of these compounds can be formulated into pharmaceutical compositions as otherwise described herein and use in the methods which are presented.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other ARM-H compound which may be used to treat HIV infection or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from HIV infection can be treated by administering to the patient (subject) an effective amount of the ARM-H compound according to the present invention including pharmaceutically acceptable salts, solvates or polymorphs, thereof optionally in a pharmaceutically acceptable carrier or diluent, either alone, or in combination with other known antiviral or pharmaceutical agents, preferably agents which can assist in treating HIV infection, including AIDS or ameliorate the secondary effects and conditions associated with HIV infection. This treatment can also be administered in conjunction with other conventional HIV therapies.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anti-HIV agents, antibiotics, antifungals, anti-inflammatories, or antiviral compounds. In certain preferred aspects of the invention, one or more ARM-H compounds according to the present invention are coadministered with another anti-HIV agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Detailed Synthetic Information

Materials and General Information:

Purchased starting materials were used as received unless otherwise noted. All moisture sensitive reactions were performed in an inert, dry atmosphere of nitrogen in flame dried glassware. Reagent grade solvents were used for extractions and flash chromatography. Reaction progress was checked by analytical thin-layer chromatography (TLC, Merck silica gel 60 F-254 plates). The plates were monitored either with UV illumination, or by charring with anisaldehyde (2.5% p-anisaldehyde, 1% AcOH, 3.5% $H_2SO_4$(conc.) in 95% EtOH) or ninhydrin (0.3% ninhydrin (w/v), 97:3 EtOH—AcOH) stains. Flash column chromatography was performed using silica gel (230-400 mesh). The solvent compositions reported for all chromatographic separations are on a volume/volume (v/v) basis. ELISA and CDC experiments were performed in triplicate and repeated at least three times unless otherwise noted. Immunofluorescence (IF) experiments were performed in duplicate and repeated at least two times.

Instrumentation:

$^1$H-NMR spectra were recorded at either 400 or 500 MHz and are reported in parts per million (ppm) on the δ scale relative to $CDCl_3$ (δ 7.26) as an internal standard unless otherwise noted. Data are reported as follows: chemical shift, multiplicity (s=singlet, d=doublet, t=triplet, q=quartet, br=broad, m=multiplet), coupling constants (Hz), and integration. $^{13}$C-NMR spectra were recorded at either 100 or 125 MHz and are reported in parts per million (ppm) on the δ scale relative to $CDCl_3$ (δ 77.00). High resolution mass spectra (HRMS) were recorded on a 9.4 T Bruker Qe FT-ICR MS (W. M. Keck Facility, Yale University). Analytical ultra high-performance liquid chromatography-mass spectrometry (UPLC/MS) was performed on a Waters UPLC/MS instrument equipped with a reverse-phase C18 column (1.7 μm particle size, 2.1×50 mm), dual atmospheric pressure chemical ionization (API)/electrospray (ESI) mass spectrometry detector, and photodiode array detector. Samples were eluted with a linear gradient of 20% acetonitrile-water→100% acetonitrile containing 0.1% formic acid over 3 min at a flow rate of 0.8 mL/min. Analytical UPLC/MS data are represented as follows: m/z; retention time (Rt) in minutes. High Pressure Liquid Chromatography (HPLC) using a Dynamax Rainin Solvent Delivery System equipped with a Varian Prostar Detector (Galaxie Chromatography Data System version 1.8.505.5), and absorbance measurements were made at 214 and 254 nm simultaneously. A Waters Xterra Prep MS C18 7.8×150 mm column was used for semi-preparative purifications using a water:acetonitrile (A:B) gradient containing 0.1% TFA at 5.0 mL/min, as specified below for individual compounds. Infrared (IR) spectra were recorded on a Thermo Nicolet 6700 FT-IR Spectrometer. Unless otherwise noted, all micro-plate based assays were quantitated using a BioTek Synergy 3 Microplate reader and data was fitted and graphed using GraphPad Prism version 5.00 for Windows (GraphPad Software, San Diego Calif. USA, www.graphpad.com) or KaleidaGraph (Synergy Software).

Supplementary Scheme 1. Representative synthesis of DNP—$PEG_n$-Alkynes

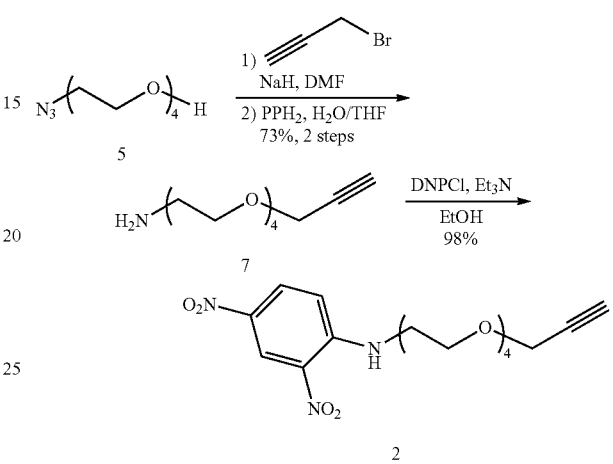

1-azido-3,6,9,12-tetraoxapentadec-14-yne

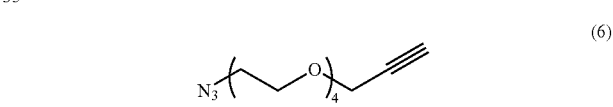

(6)

2-(2-(2-(2-azidoethoxy)ethoxy)ethoxy)ethanol[1] (7.55 g, 34 mmol, 1.0 equiv., 5) was dissolved in DMF (150 mL), and sodium hydride (989 mg, 40.8 mmol, 1.2 equiv.) was added, followed by propargyl bromide (80% in PhMe, 7.4 mL, 68 mmol, 2.0 equiv.). The reaction ran for 3 h at rt, at which time it was found complete by thin layer chromatography, was concentrated and chromatographed by silica gel chromatography (30% EtOAc in hexanes) to yield 6 as a clear oil (7.55 g, 86% yield). IR (thin film/NaCl) 3252 (w), 2869 (s), 2110 (s), 1460 (w), 1349 (m), 1103 (s), 943 (w), 848 (w), 663 (w) cm-1; 1HNMR (400 MHz, CDCl3) δ 4.13-4.23 (t, J=2.4 Hz, 1H), 3.71-3.59 (m, 14H), 3.41-3.30 (t, J=5.1 Hz, 2H), 2.41 (t, J=2.4 Hz, 1H); 13CNMR (125 MHz, CDCl3) δ 79.55, 74.47, 70.47, 70.45, 70.43, 70.42, 70.20, 69.84, 68.91, 58.18, 50.50; HRMS (ES+) calc'd for C11H19N3O4 (M+H) m/z 258.14483. Found 258.14496.

[1]. Gong, Y.; Luo, Y.; Bong, D. *JACS* 2006, 45, 14430-14431.

(41)

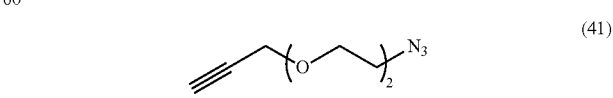

Prepared 41 in the same manner as compound 6 from 2-(2-azidoethoxy)ethanol.

3,6,9,12-tetraoxapentadec-14-yn-1-amine

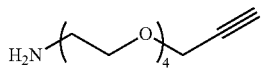
(7)

1-azido-3,6,9,12-tetraoxapentadec-14-yne 6 (2.45 g, 9.53 mmol, 1 equiv.), triphenylphosphine (3.00 g, 11.4 mmol, 1.2 equiv.), and water (172 mL, 9.53 mmol, 1.0 equiv.) were dissolved in THF (30 mL) and stirred for 12 h when TLC (95:5 CH$_2$Cl$_2$/CH$_3$OH) indicated completion. Reaction was concentrated and chromatographed (100% CH$_2$Cl$_2$ to 80:20:1 CH$_2$Cl$_2$/MeOH/Et$_3$N) to yield 7 as a clear oil (1.88 g, 85% yield). IR (thin film, NaCl) 3372 (br), 3251 (s), 2868 (s), 2112 (w), 1652 (m), 1596 (m), 1459 (m), 1350 (m), 1301 (m), 1249 (m), 1100 (s), 946 (m), 681 (m) cm$^{-1}$. $^1$H-NMR (500 MHz, CDCl$_3$) δ 4.16 (m, 2H), 3.66-3.57 (m, 12H), 3.49 (t, 2H, J=5.3 Hz), 2.85 (t, 2H, J=5.0 Hz), 2.56 (bs, 2H), 2.41 (m, 1H). $^{13}$C NMR (125 MHz, CDCl$_3$) δ 79.52, 74.63, 73.06, 70.45, 70.41, 70.24, 70.11, 68.96, 58.26, 41.50. HRMS (ES+) calc'd for C$_{11}$H$_{21}$NO$_4$ (M+H) m/z 232.154335. Found 232.15402.

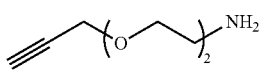
(42)

Prepared 42 in the same manner as compound 7 starting from 41.

N-(2,4-dinitrophenyl)-3,6,9,12-tetraoxapentadec-14-yn-1-amine

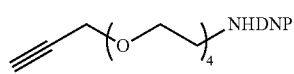
(2)

3,6,9,12-tetraoxapentadec-14-yn-1-amine 7 (1.0 g, 4.3 mmol, 1 equiv.) was dissolved in EtOH (18 mL), and triethylamine (1.68 mL, 8.6 mmol, 2 equiv.) and 1-chloro-2,4-dinitrobenzene (876 mg, 4.3 mmol, 1 equiv.) were added. The reaction flask was fitted with a reflux condenser and the reaction was heated to reflux for 2 h, cooled, and concentrated to a crude yellow oil. The crude mixture was re-dissolved in H$_2$O (25 mL) and extracted with CH$_2$Cl$_2$ (5×10 mL). Organic layers were dried over Na$_2$SO$_4$ and concentrated to a yellow oil that was purified by flash chromatography (CombiFlash Automated Chromatographer, 25 g column, dryloaded with 25 g pre-packed dry loading column. Run using 10% EtOAc:Hexanes to 50% EtOAc:Hexanes gradient over 30 column volumes, followed by EtOAc flush) to yield 2 as a yellow solid (1.70 g, >98% yield). IR (thin film/NaCl) 3360(m), 3290 (m), 3110 (w), 2873 (m), 2114(w), 1621 (s), 1588 (m), 1336 (s), 1134 (m) cm$^{-1}$; $^1$H-NMR (500 MHz, CDCl$_3$) δ 9.13 (d, 1H, J=2.6 Hz), 8.80 (broad peak, 1H), 8.25 (dd, 1H, J=2.6, J=9.5 Hz), 6.94 (d, 1H, J=9.5 Hz), 4.18 (m, 2H), 3.83 (t, 2H, J=5.2 Hz), 3.67 (m, 12H), 3.60 (q, 2H), 2.41 (m, 1H); $^{13}$C-NMR (125 MHz, CDCl$_3$) δ 148.6, 136.2, 130.4, 124.4, 114.3, 79.8, 74.7, 70.8, 70.7, 70.5, 69.2, 68.7, 58.5, 43.4; HRMS (EI) calc'd for C$_{17}$H$_{23}$N$_3$O$_8$ (MH+) m/z 398.1558. Found 398.1557.

(43)

Prepared 43 in the same manner as compound 2 starting from 42.

$^1$H NMR (400 MHz, CDCl$_3$) δ 9.15 (d, J=2.7, 1H), 8.81 (s, 1H), 8.42-8.19 (m, 1H), 6.96 (d, J=9.5, 1H), 4.21 (d, J=2.4, 2H), 3.84 (t, J=5.3, 2H), 3.74 (broad peak, 4H), 3.61 (dd, J=5.2, 10.5, 2H), 2.44 (t, J=2.4, 1H).

Supplementary Scheme 2. Representative Synthesis of ARM—H type (47) molecules with DNP containing Amino Acids

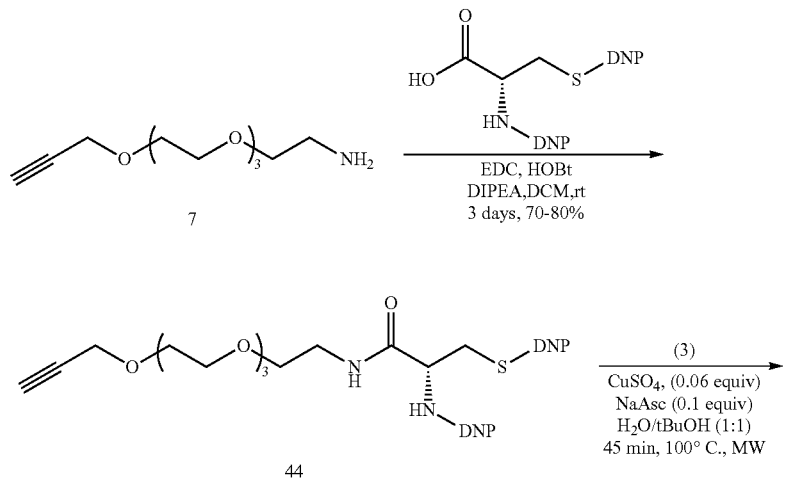

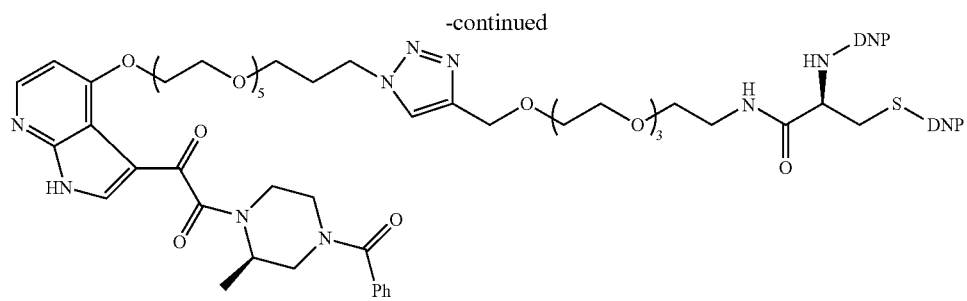

47

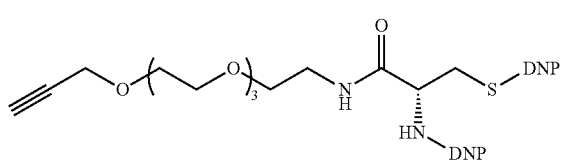

(44)

To a solution of N,S-Di(2,4-dinitrophenyl)-L-cysteine (200 mg, 0.441 mmol, purchased from Aldrich) in anhydrous CH2Cl2 (10 mL) at 0 C, added 7 (148 mg, 0.641 mmol, 1.45 equiv), 1-ethyl-3-(3-dimethylaminopropyl) carbodiimide hydrochloride (EDC-HCl, 126 mg, 0.651 mmol), hydroxybenzotriazole monohydrate (HOBT, 89 mg, 0.659 mmol) and diisopropylethylamine (330 uL). Let yellow solution warm to room temperature while stirring under an atmosphere of nitrogen. After 48 hrs, TLC (9:1 CH2Cl2/CH3OH) indicated reaction completion and solution was diluted with CH2Cl (40 mL), washed with saturated NaHCO3 (2×40 mL) and brine (1×40 mL). Organic fraction was dried over anhydrous Na2SO4, filtered and concentrated under reduced pressure, yielding crude 10, which was purified by flash column chromatography (0%-5% CH3OH in CH2Cl2, note: purification can be monitored visually by observing separation of yellow band on silica), resulting in pure 44 (230 mg, 0.35 mmol 80%) as a sticky yellow solid. 1H NMR (500 MHz, CDCl3) δ 9.10 (s, 1H), 9.03 (s, 2H), 8.41 (d, J=8.9, 1H), 8.29 (d, J=9.3, 1H), 7.77 (d, J=8.8, 1H), 7.66 (s, 1H), 6.99 (d, J=9.3, 1H), 4.63 (dd, J=6.4, 12.2, 1H), 4.13 (s, 2H), 3.78 (dd, J=4.6, 13.1, 1H), 3.74-3.36 (m, 17H), 2.41 (t, J=2.1, 1H).

Supplementary Scheme 3. Representative synthesis of ARM—H type (4) analogs.

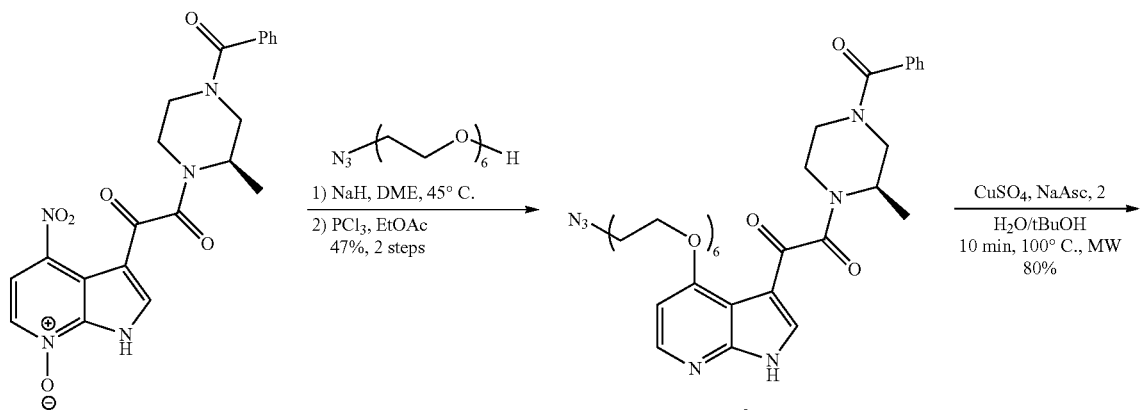

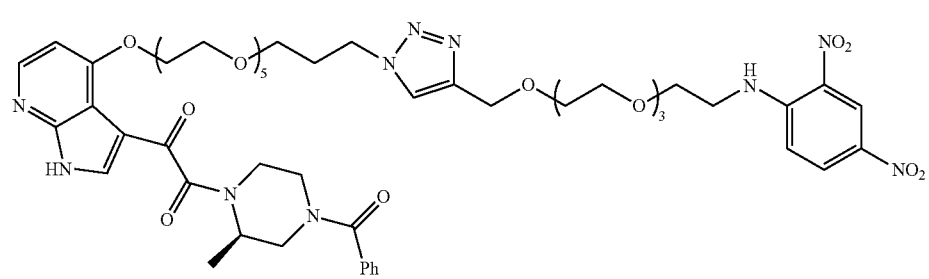

4-Benzoyl-2-(R)-methyl-1-[(4-nitro-7-oxido-1H-pyrrolo[2,3-b]pyridin-3-yl)oxoacetyl]-piperazine

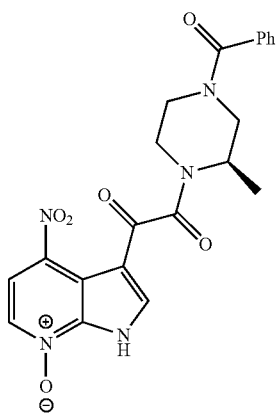

(8)

This compound was synthesized as previously described[2]. All synthetic intermediates as well as the final product analytical data were in agreement with that reported[3].

[2]. Wang, T.; Zhang, Z.; et al. *J. Med. Chem.* 2003, 46, 4236-4239.
[3]. Zych, A.; Iverson, B. *JACS* 2000, 37, 8898-8909.

Method 1: Synthesis of Azide-PEG-Azaindoles (Synthesis of 3 Provided as Example)

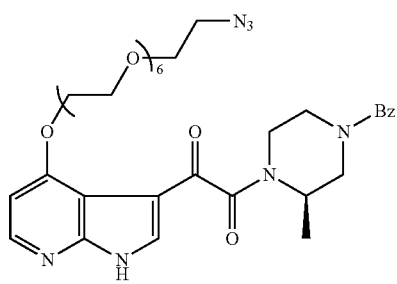

To a stirred mixture of 255 mg NaH (95%, 9.88 mmol, 7.2 equiv, Aldrich), anhydrous dimethoxyethane (21 mL) was added followed by addition of hexaethylene azido glycol (1.512 g, 4.93 mmol, 7.2 equiv)[3] in anhydrous dimethoxyethane (21 mL). The resulting yellow solution was stirred for 2 hrs before 8 (300 mg, 0.686 mmol) was added as a solution in dimethoxyethane (7.5 mL) via cannula at room temperature. The resulting copper colored mixture was heated to 45° C. and monitored by TLC (9:1 $CH_2Cl_2/CH_3OH$). After approximately 2 hrs, the brown mixture was allowed to cool to room temperature, aq. $NH_4Cl$ (15 mL) was slowly added and the organic layer was extracted with $CH_2Cl_2$ (5×80 mL). The organic phases were combined, dried over anhyd. $MgSO_4$, filtered, and all solvents were evaporated. The resulting brown crude residue 9 was purified chromatographically on silica (0% to 20% $CH_3OH$ in $CH_2Cl_2$) to remove unreacted azido alcohol. The resulting yellow oil (650 mg) was carried on without further purification. Compound 9 (650 mg) was then dissolved in 40 mL EtOAc. To this solution was added 1.10 mL $PCl_3$ (6.92 mmol, 10 equiv), resulting in an orange heterogeneous mixture, which was allowed to stir at r.t. After 2 hrs the reaction was quenched by the careful addition of aq. $NaHCO_3$ at 0° C. until pH of 6 was reached. The mixture was extracted with EtOAc (5×50 mL) and the combined organic layers were dried over anhydrous $Na_2SO_4$, filtered, and all solvents were evaporated. These crude isolates were then purified by column chromatography (0% to 8% $CH_3OH$ in $CH_2Cl_2$), to yield 3 as a clear solid (421 mg, 0.618 mmol, 45% over 2 steps). IR (thin film/NaCl) 3095 (w), 2872 (s), 2107(s), 1635 (s), 1433 (m), 1097 (m) cm$^{-1}$. $^1$H-NMR (500 MHz, CDCl$_3$, rt) δ 12.5 (s, 1H), 8.28 (d, J=5.6 Hz, 1H), 8.03 (d, J=18.3 Hz, 1H) 7.41 (broad peak, 5H), 6.76 (d, J=3.8 Hz, 1H), 5.05-4.45 (broad peak, 2H), 4.38 (broad peak, 2H), 4.02 (broad peak, 2H), 3.78 (broad peak, 2H) 3.68-3.58 (m, 18H), 3.48 (m, 1H), 3.37 (m, 2H), 3.15 (broad peak, 2H), 1.30 (broad peak, 3H)$^{13}$C-NMR (75 MHz, CD$_3$OD, rt) δ 184.8, 167.2, 161.4, 152.1, 146.8, 135.5, 130.5, 129.1, 127.5, 118.9, 114.5, 108.4, 102.3, 71.5, 71.1, 71.0, 70.4, 69.7, 69.00, 68.9, 51.1, 45.2, 16.6, 15.5. HRMS (EI) m/z (%) for $C_{33}H_{43}N_7O_9$ (MH+) calc'd 682.3195. found 682.3205; for (M+Na)+ calc'd 704.3014. found 704.3017.

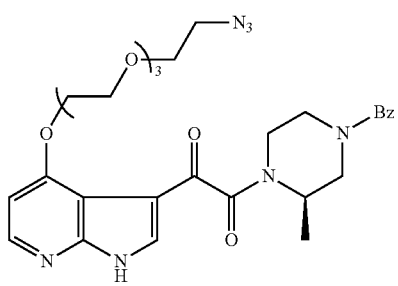

(45)

Prepared according to Method 1 as in compound 3 using 2-(2-(2-(2-azidoethoxy)ethoxy)ethoxy)ethanol. $^1$H-NMR (500 MHz, CDCl$_3$, rt) δ 8.24 (d, J=5.8, 1H), 8.03 (d, J=18.3, 1H), 7.41 (s, 5H), 6.77 (s, 1H), 4.39 (s, 2H), 4.03 (s, 2H), 3.79 (s, 2H), 3.71-3.38 (m, 13H), 3.35 (t, J=5.0, 2H), 3.08 (s, 2H), 1.25 (broad signal, 3H).

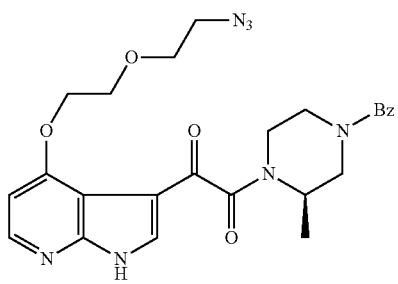

(46)

Prepared according to Method 1 as in compound 3 using 2-(2-azidoethoxy)ethanol. $^1$H-NMR (400 MHz, CDCl$_3$, rt) δ 8.20 (d, J=5.8, 1H), 7.96 (d, J=13.8, 1H), 7.34 (s, 5H), 6.71 (d, J=5.3, 1H), 4.94-4.42 (m, 2H), 4.33 (s, 2H), 3.98 (s, 2H), 3.79 (s, 2H), 3.67-2.86 (m, 7H) 1.30 (broad peak, 3H).

Method 2: General Procedure for Alkyne-Azide Coupling Reactions (Synthesis of 4 Provided as Example)

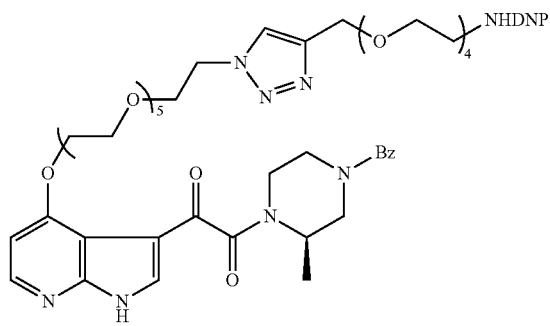

To a solution of 2 (45.0 mg, 0.066 mmol) dissolved in t-BuOH (1.7 mL) and H$_2$O (1.6 mL) was added 3 (51 mg, 0.125 mmol, 1.9 equiv). The mixture was stirred for 5 min before aqueous CuSO$_4$.5H$_2$O (0.1M, 33 μL, 0.05 equiv) and aqueous sodium ascorbate (0.1M, 66 μL, 0.1 equiv) were added. The reaction vessel was then capped and heated in a microwave reactor for 20 min at 125° C. at which time TLC (9:1 CH$_2$Cl$_2$/CH$_3$OH) indicated reaction completion. The golden yellow solution was transferred to a flask using CH$_3$OH and all solvents were evaporated, providing 35 mg of crude 4 as a golden yellow solid which was subsequently purified by flash chromatography (0% to 10% CH$_3$OH in CH$_2$Cl$_2$) to deliver 57 mg (0.053 mmol, 80%) of 2 as a golden yellow solid. IR (thin film/NaCl) 3356 (w), 3111 (w), 2931 (m), 2876 (s), 1620 (s), 1515 (m), 1433 (m), 1334 (m), 1297 (m), 1123 (m) cm$^{-1}$. $^1$H-NMR (500 MHz, CDCl$_3$, rt) δ 12.74, (broad peak, 1H), 9.08 (d, J=2.5 Hz, 1H) 8.76 (s, 1H), 8.26 (d, J=4.7 Hz, 1H), 8.22 (dd, J=2.6, 9.5 Hz, 1H), 8.01 (d, J=19.9 Hz, 1H), 7.70 (s, 1H), 7.40 (broad peak, 5H), 6.93 (d, J=9.5 Hz, 1H), 6.73 (broad peak, 1H), 5.1-4.7 (broad peak, 1H) 4.4 (broad peak, 2H), 4.49 (t, 2H, J=5.1 Hz), 4.36 (broad peak, 2H), 4.01 (broad peak, 2H), 3.95-3.31 (m, 38H), 3.29-2.9 (broad peak, 2H) 1.30-1.38 (broad peak, 3H). NOTE: When sample is heated in DMSO-d$_6$ to 100° C., broadened proton signals coalesce, suggesting the presence of rotameric conformations. $^{13}$C-NMR (75 MHz, CDCl$_3$, rt) δ 184.9, 167.1, 161.2, 151.9, 148.8, 147.2, 145.2, 136.5, 135.6, 130.9, 130.6, 130.5, 130.4, 129.1, 127.5, 124.6, 124.1, 114.6, 114.5, 108.1, 102.3, 102.3, 71.5, 71.1, 71.1, 71.1, 71.0, 70.9, 70.8, 70.0, 69.9, 69.8, 69.7, 69.0, 64.9, 50.6, 50.3, 45.2, 43.7, 16.6, 15.5. HRMS (EI) m/z (%) for C$_{50}$H$_{66}$N$_{10}$O$_{17}$ (MH+) calc'd 1079.4680. found 1079.4663; for (M+Na)+ calc'd 1101.4500. found 1101.4458.

(29)

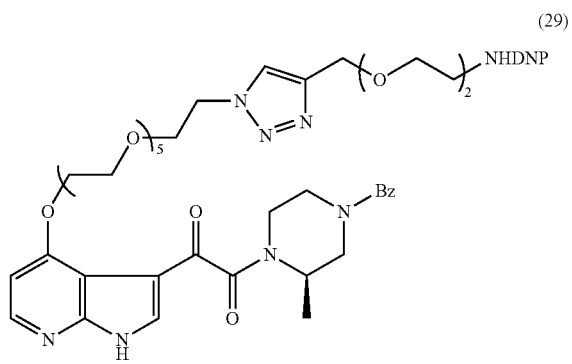

Prepared according to Method 2 as in compound 4. $^1$H NMR (400 MHz, CDCl$_3$) δ 9.03 (s, 1H), 8.75 (s, 1H), 8.24 (s, 1H), 8.17 (d, J=9.5, 1H), 7.99 (d, J=16.6, 1H), 7.75 (s, 1H), 7.41 (s, 5H), 6.87 (dd, J=1.8, 9.5, 1H), 6.72 (s, 1H), 4.66 (s, 2H), 4.49 (t, J=4.8, 2H), 4.36 (s, 2H), 4.01 (s, 2H), 3.88-2.82 (m, 33H) 1.30-1.37 (broad peak, 3H). UPLC/MS: (ES+) m/z (M+H)$^+$ 991; (M+Na)$^+$ 1013; Rt=1.21

(30)

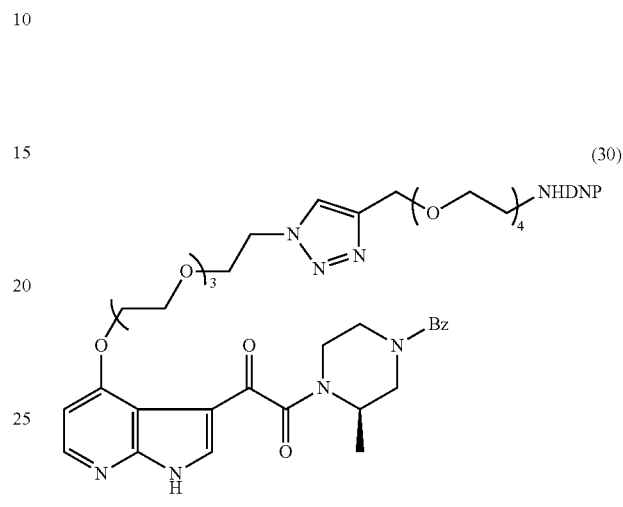

Prepared according to Method 2 as in compound 4. $^1$H NMR (500 MHz, CDCl$_3$, rt) δ 8.24 (d, J=5.8, 1H), 8.03 (d, J=18.3, 1H), 7.41 (broad signal, 5H), 6.77 (s, 1H), 4.39 (broad signal, 4H), 4.03 (s, 2H), 3.79 (s, 2H), 3.71-3.38 (m, 11H), 3.35 (t, J=5.0, 2H), 3.08 (s, 2H), 1.25 (broad signal, 3H). UPLC/MS: (ES+) m/z (M+H)$^+$ 991; (M+Na)$^+$ 1013; Rt=1.20

(31)

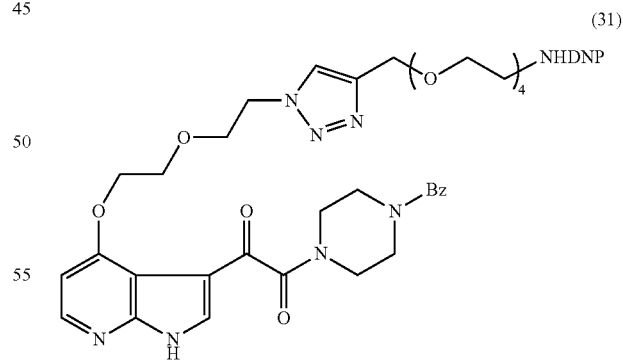

Prepared according to Method 2 as in compound 4. $^1$H-NMR (500 MHz, CDCl$_3$, rt) δ 8.71 (s, 1H), 8.22 (s, 1H), 8.17 (d, J=9.4, 1H), 7.99 (d, J=17.5, 1H), 7.56 (s, 1H), 7.41 (s, 5H), 6.86 (d, J=9.5, 1H), 6.65 (s, 1H), 4.53 (s, 2H), 4.31 (s, 4H), 4.02 (d, J=21.9, 4H), 3.79 (t, J=4.7, 2H), 3.75-3.39 (m, 19H) 1.31-1.38 (broad peak, 3H). UPLC/MS: (ES+) m/z (M+H)$^+$ 903; (M+Na)$^+$ 925; Rt=1.20

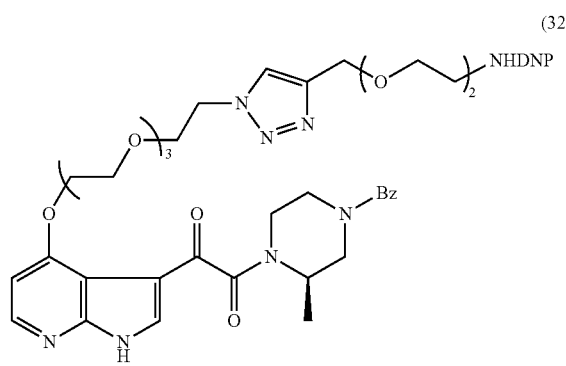

(32)

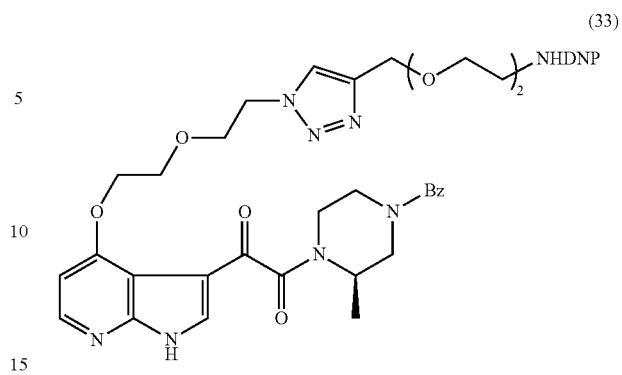

(33)

Prepared according to Method 2 as in compound 4. $^1$H-NMR (500 MHz, CDCl$_3$, rt) δ 9.07 (s, 1H), 8.77 (s, 1H), 8.21 (m, 2H), 7.97 (d, J=17.0, 1H), 7.77 (s, 1H), 7.41 (broad signal, 6H), 6.91 (d, J=9.4, 1H), 6.73 (s, 1H), 4.67 (s, 2H), 4.52 (t, J=5.1, 2H), 4.35 (s, 2H), 4.00 (s, 2H), 3.87-3.50 (m, 25H) 1.30-1.38 (broad peak, 3H). UPLC/MS: (ES+) m/z (M+H)$^+$ 903; (M+Na)$^+$ 925; Rt=1.19

Prepared according to Method 2 as in compound 4. $^1$H-NMR (500 MHz, CDCl$_3$, rt) δ 9.09 (d, J=2.6, 1H), 8.85-8.75 (m, 1H), 8.35-8.17 (m, 2H), 8.00 (d, J=15.3, 1H), 7.75 (s, 1H), 7.43 (broad signal, 5H), 6.91 (d, J=9.8, 1H), 6.71 (s, 1H), 4.58 (s, 2H), 4.52 (s, 3H), 4.32 (s, 2H), 4.10 (s, 2H), 4.02 (s, 2H), 3.80 (s, 2H), 3.65 (m, 6H), 3.58 (s, 2H), 3.51 (s, 2H) 1.31-1.39 (broad peak, 3H). UPLC/MS: (ES+) m/z (M+H)$^+$ 815; (M+Na)$^+$ 837; Rt=1.15

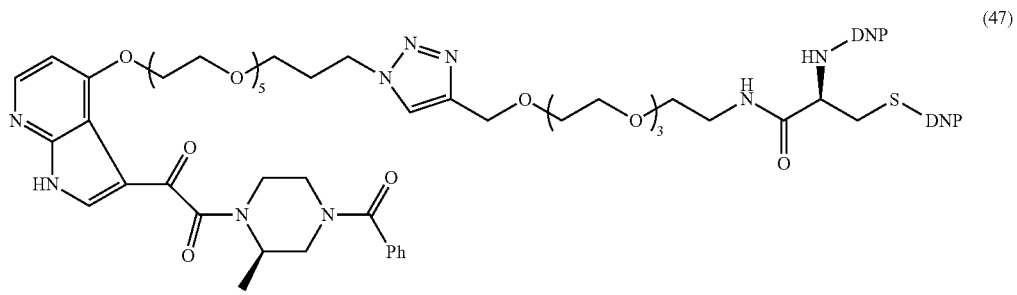

(47)

To a solution of 3 (30.0 mg, 0.044 mmol) dissolved in t-BuOH (1.4 mL) and H2O (1.4 mL) in a microwave reaction vessel, was added 44 (32 mg, 0.048 mmol, 1.1 equiv). The mixture was stirred for 5 min before aqueous CuSO4.5H2O (0.1M, 20 μL) and aqueous sodium ascorbate (0.1M, 60 μL) were added. The reaction vessel was then capped and heated in a microwave reactor for 18 min at 125° C. at which time TLC (9:1 CH2Cl2/CH3OH) indicated reaction completion. The golden yellow solution was transferred to a flask using CH3OH, and solvents were evaporated, providing 55 mg of crude 47 as a golden yellow solid, which was purified by flash chromatography (0% to 10% CH3OH in CH2Cl2) to deliver 44 mg (0.033 mmol, 75%) of 12 as a golden yellow solid. $^1$H NMR (500 MHz, CDCl$_3$) δ 12.17 (bs, 1H), 9.04 (d, J=7.3, 1H), 9.01 (s, 1H), 8.93 (s, 1H) 8.52 (bs, 1H), 8.31 (dd, J=2.2, 8.9, 1H), 8.22 (broad peak, 1H), 8.15 (d, J=9.0, 1H), 8.02 (s, 0.5H), 7.98 (s, 0.5H) 7.78 (d, J=9.0, 1H), 7.70 (s, 1H), 7.41 (broad peak, 5H), 7.03 (d, J=9.4, 1H), 6.72 (broad peak, 1H), 4.82 (broad peak, 2H), 4.60 (s, 2H), 4.45 (t, J=4.9, 2H), 4.36 (s, 2H), 4.01 (broad peak, 2H), 3.79-3.14 (m, 40H), 3.29-2.95 (broad peak, 2H) 1.28 (s, 3H) HRMS (EI) m/z (%) for C$_{59}$H$_{73}$N$_{13}$O$_{22}$S (MH+) calc'd 1348.4793. found 1348.4740; for (M+Na)+ calc'd 1370.4558. found 1370.4594.

Supplementary Scheme 4. Representative Synthesis of ARM—H type (14) and type (28) molecules
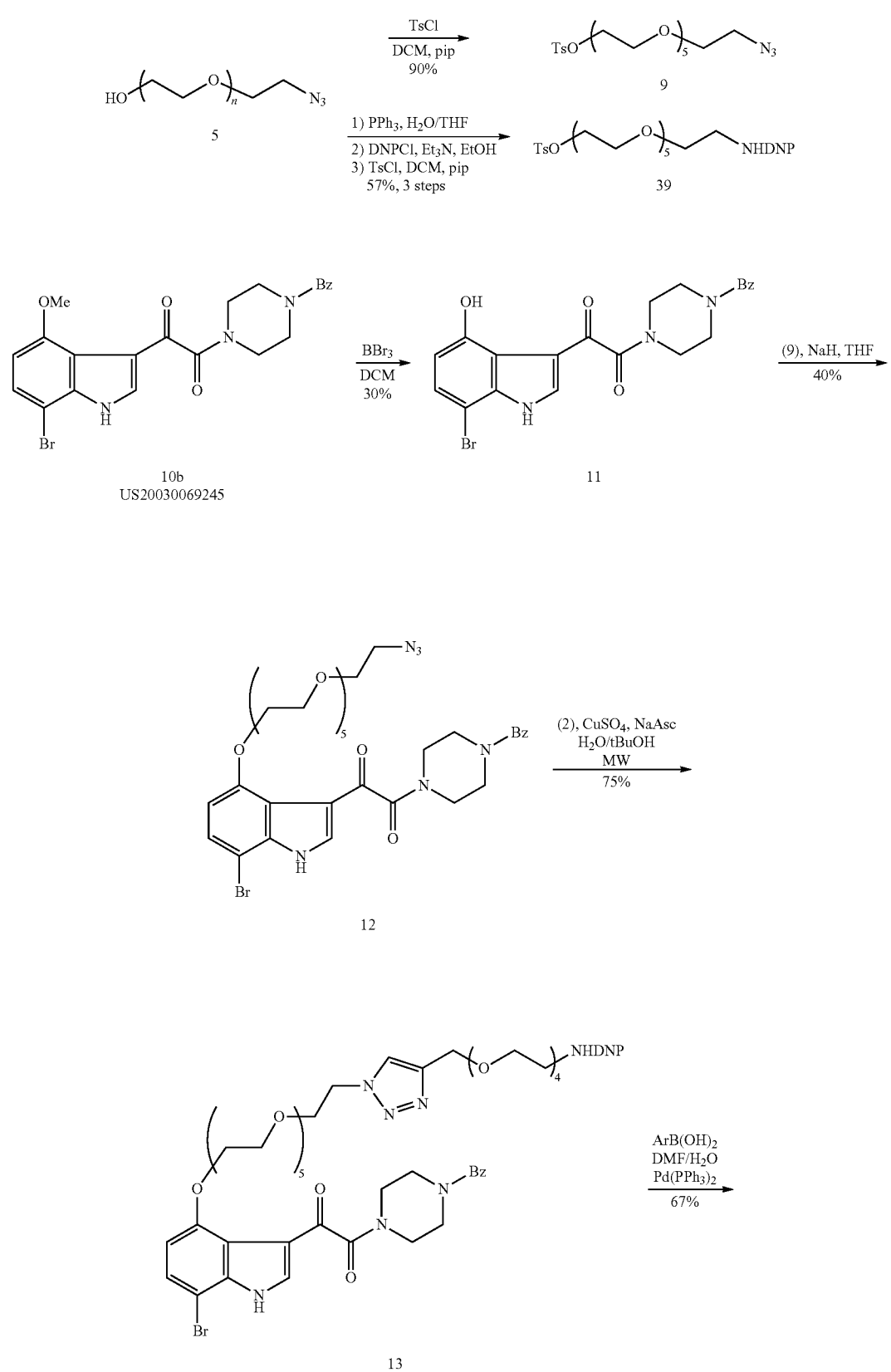

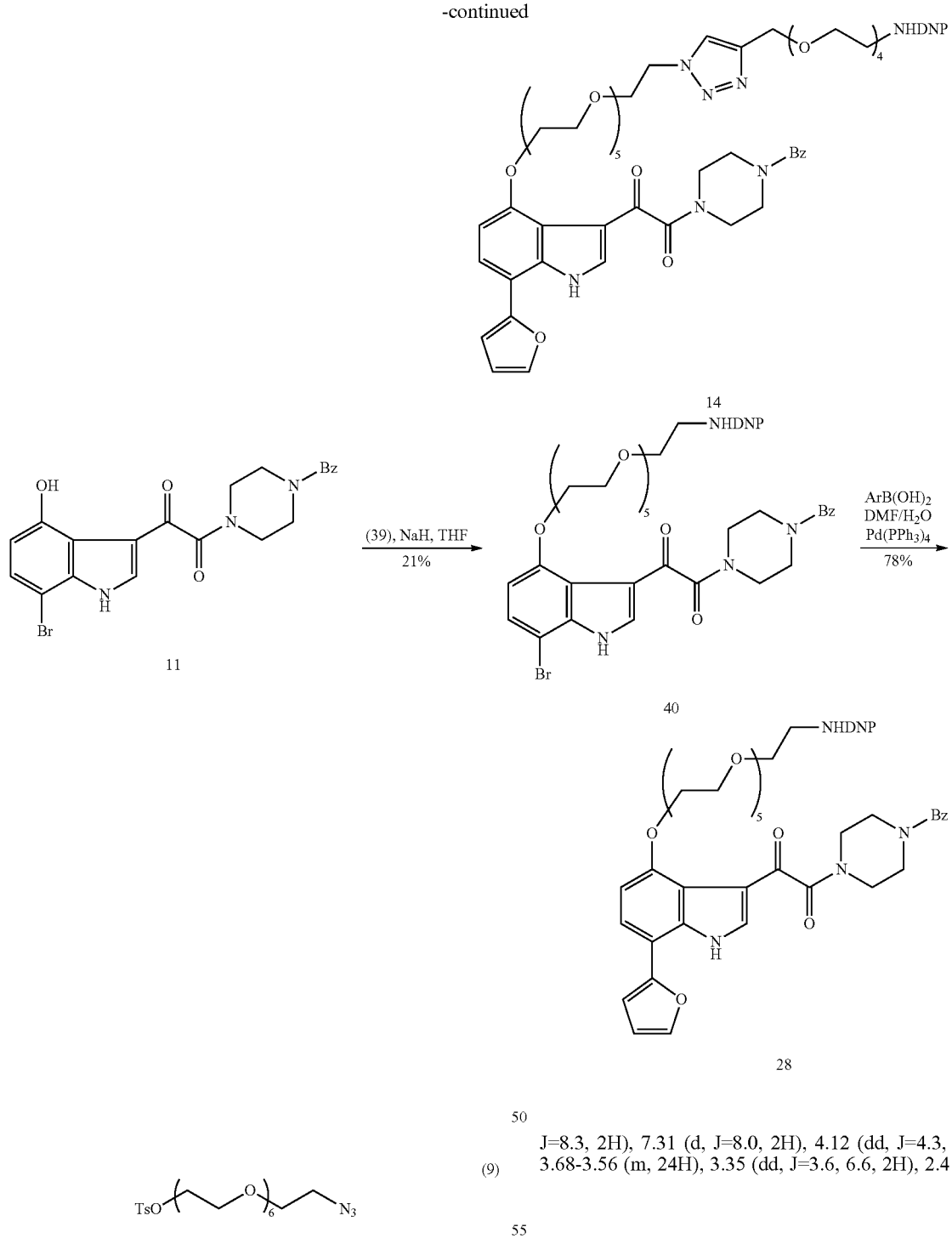

To a solution of 5 (6.45 g, 21 mmol) in CH₂Cl₂ (35 mL), added a solution of 4-toluenesulfonyl chloride (4.56 g, 25.2 mmol, 1.2 equiv) in pyridine (9 mL) dropwise via addition funnel. Let homogeneous mixture stir at room temperature until TLC (20:1 CH₂Cl₂/CH₃OH) indicated reaction completion (14 hrs). Reaction mixture was diluted with additional CH₂Cl₂, the organic layer was washed twice with aq. HCl (2M, 30 mL), dried over anhydrous MgSO₄, filtered and all solvents were evaporated yielding 9 as a colorless oil (8.67 g, 18.8 mmol, 90%). Crude material was used without further purification. $^1$H NMR (400 MHz, CDCl₃) δ 7.76 (d, J=8.3, 2H), 7.31 (d, J=8.0, 2H), 4.12 (dd, J=4.3, 5.4, 2H), 3.68-3.56 (m, 24H), 3.35 (dd, J=3.6, 6.6, 2H), 2.41 (s, 3H).

Prepared 48 in the same manner as compound (7) in 86% yield. $^1$H NMR (400 MHz, CDCl₃) δ 3.71-3.67 (m, 2H), 3.66-3.54 (m, 18H), 3.53-3.48 (m, 2H), 2.88-2.79 (m, 2H), 2.58 (broad peak, 2H).

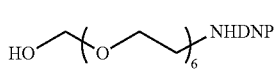
(49)

Prepared 49 in the same manner as compound (2) in 66% yield. ¹H NMR (400 MHz, CDCl₃) δ 9.15 (d, J=2.7, 1H), 8.82 (s, 1H), 8.27 (dd, J=2.7, 9.5, 1H), 6.97 (d, J=9.6, 1H), 3.83 (t, J=5.3, 2H), 3.76-3.55 (m, 2214).

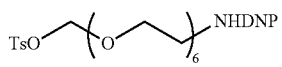

(39) Prepared 39 in the same manner as compound (9) in 67% yield. ¹H NMR (400 MHz, CDCl₃) δ 9.21-9.13 (m, 1H), 8.83 (s, 1H), 8.29 (dd, J=2.7, 9.5, 1H), 7.81 (d, J=8.1, 2H), 7.37 (d, J=8.5, 2H), 6.98 (d, J=9.5, 1H), 4.17 (dt, J=6.8, 13.7, 2H), 3.86 (t, J=5.1, 2H), 3.78-3.55 (m, 20H), 2.47 (s, 314).

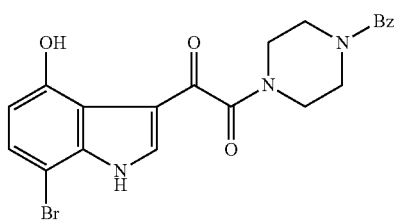
(11)

To a flame-dried flask, added 10b (750 mg, 1.6 mmol)⁴ followed by 35 mL anhydrous CH₂Cl₂. Resulting mixture was cooled to −78° C. with dry ice/acetone bath and BBr₃ (1.0M in CH₂Cl₂, 13.5 mL, 13.5 mmol, 8.4 equiv) was carefully added via syringe under an atmosphere of N₂. The resulting purple mixture was allowed to warm to RT over a period of 2 hr and then heated to reflux until indicated no remaining starting material (72 hrs). The mixture was allowed to cool to RT and carefully quenched with aq. NaOH (0.5M, 50 mL) and extracted with EtOAc (3×200 mL). The combined organic layers were then washed with saturated NaHCO₃ and brine, dried over anhydrous MgSO₄, filtered and all solvents were evaporated, yielding crude 11 as a red solid. Crude 11 purified by flash chromatography (3:1 hexanes/acetone→1:1→100% acetone). Compound can be further purified by washing several times with a 1:1 mixture of dichloromethane/hexanes, resulting in pure 11 as an off yellow powder (218 mg, 0.48 mmol, 30%). ¹H NMR (500 MHz, CDCl₃) δ 10.42 (s, 1H), 9.08 (s, 1H), 8.01 (s, 1H), 7.42 (s, 5H), 7.33 (d, J=8.4, 1H), 6.69 (d, J=8.6, 1H), 3.83-3.36 (m, 814). UPLC/MS: (ES+) m/z (M+H)⁺ 456; Rt=1.34.

⁴. US PATENT: US20030069245

(12)

To a flame-dried flask containing a solution of NaH (>95%, 1.1 mg, 0.046 mmol) in anhydrous THF (1.0 mL), added 11 (10 mg, 22.0 µmol) n THF (1.0 mL) followed by slow addition of 9 in THF (1.0 mL). The resulting green mixture was allowed to stir at RT under an atmosphere of N₂. After 12, 24 and 36 hr, carefully added addition NaH (2 mg each addition). After 5 days, TLC (1:1 hexanes/acetone) indicated reaction completion. Reaction was quenched with H₂O (5 mL) and extracted with CH₂Cl₂ (3×10 mL). The combined organic layers were washed with brine (30 mL), dried over anhydrous over anhydrous MgSO₄, filtered and all solvents were evaporated. Crude 12 was purified by prepatory thin layer chromatography (AnalTech Uniplate 1000 µm; eluting with 1:1 hexanes/acetone), resulting in 12 as a clear residue (6.0 mg, 0.008 mmol, 40%). ¹H NMR (500 MHz, CDCl₃) δ 8.12-7.99 (m, 1H), 7.42 (s, 5H), 7.33 (s, 1H), 6.65 (d, J=8.1, 1H), 4.29 (s, 2H), 3.92 (s, 2H), 3.71 (s, 2H), 3.62 (d, J=24.2, 15H), 3.39 (m, 2H). UPLC/MS: (ES+) m/z (M+H)⁺ 745; Rt=1.72.

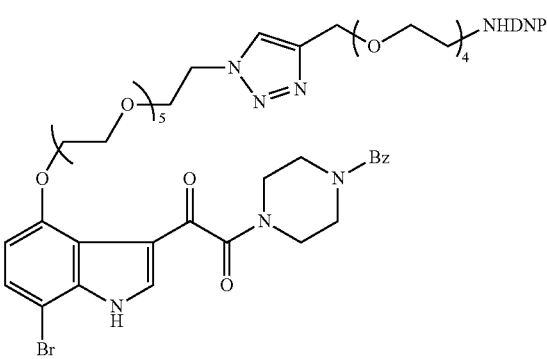
(13)

Prepared according to Method 2 as in compound 4 using 3.5 mg (0.0047 mmol) of 12. Crude 13 purified by HPLC (0-60% B, 60 min.) Yielded 13 as a yellow residue (4 mg, 75%). UPLC/MS: (ES+) m/z (M+H)⁺ 885; Rt=1.56

Method 3: Coupling Between Indole Bromides and Aryl Boronic Acids (Synthesis of 14 as Example)

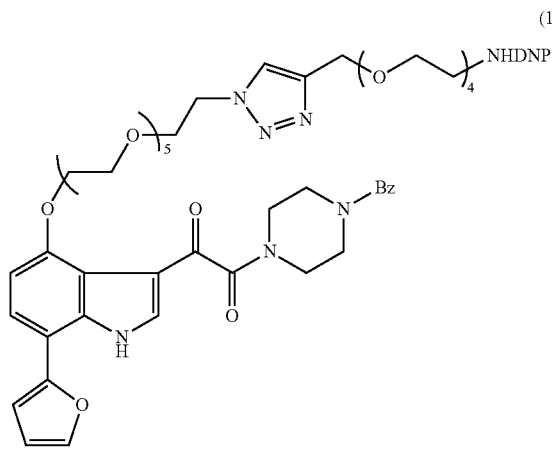

(14)

To a solution of 13 (3 mg, 2.63 µmol) in 300 µL dimethylformamide (DMF) in a microwave vial, added NaHCO$_3$ (0.287 mg, 3.4 µmol, 1.3 equiv; in 185 µL H$_2$O) and 2-furanylbornic acid (0.4 mg, 3.4 µmol, 1.3 equiv). Removed O$_2$ from solution by bubbling with N$_2$ for at least 10 min. Carefully added Pd(PPh$_3$)$_4$ (0.15 mg, 0.13 µmol, 5 mol %), capped vial and heated in a microwave reactor for 12 min at 150° C. Evaporated all solvents and purified crude residue by HPLC (0-60% B gradient, 60 min run time). Yielded 14 as a yellow solid (4 mg, 67%).

(40) To a flame-dried flask containing a solution of NaH (>95%, 1.1 mg, 46.0 µmol) in anhydrous THF (1.0 mL), added 11 (10 mg, 22.0 µmol) in THF (1.0 mL) followed by slow addition of 39 in THF (1.0 mL) and finally, by the addition of 15-crown-5 (5 mg, 4.6 µL). The resulting red mixture was allowed to stir at RT under an atmosphere of N$_2$. After 12 and 24 hrs added additional NaH (2 mg each addition), monitoring by TLC (30:1 EtOAc/ CH$_3$OH). After 3 days, all solvents were evaporated and crude 40 was purified by HPLC (0-60% B gradient, 60 min run time). Isolated pure 40 as a yellow residue (4.0 mg, 4.5 µmol, 21%). $^1$H NMR (500 MHz, CDCl$_3$) δ 9.11 (d, J=2.7, 1H), 9.09-9.01 (m, 1H), 8.78 (s, 1H), 8.23 (dd, J=2.7, 9.5, 1H), 8.01 (s, 1H), 7.44 (broad signal, 5H), 7.33 (d, J=8.5, 1H), 6.92 (d, J=9.5, 1H), 6.65 (d, J=8.5, 1H), 4.28 (s, 2H), 3.97-3.52 (m, 30H). UPLC/MS: (ES+) m/z (M+H)$^+$ 885; Rt=1.56.

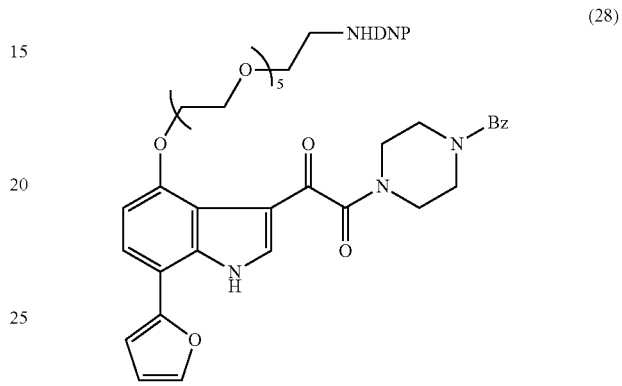

(28)

Prepared according to Method 3 as in compound 14 starting from 2.5 mg of 40 (2.8 µmol). Crude 28 was purified by HPLC (0-60% B gradient, 60 min run time), yielding 28 as a yellow residue (1.9 mg, 2.2 µmol, 78%). $^1$H NMR (500 MHz, CDCl$_3$) δ 9.05 (s, 1H), 8.72 (s, 2H), 8.17 (d, J=9.2, 1H), 8.03 (s, 1H), 7.56 (d, J=1.5, 1H), 7.49-7.38 (m, 1H), 6.86 (d, J=10.0, 1H), 6.76 (d, J=7.6, 1H), 6.67 (d, J=3.0, 1H), 6.55 (dd, J=1.7, 3.5, 1H), 4.38-4.29 (m, 2H), 3.99-3.90 (m, 2H), 3.87-3.51 (m, 30H). UPLC/MS: (ES+) m/z (M+H)$^+$ 873; (M+H)$^+$ 895 Rt=1.63.

Supplementary Scheme 5. Representative Synthesis of ARM—H type (22) molecules

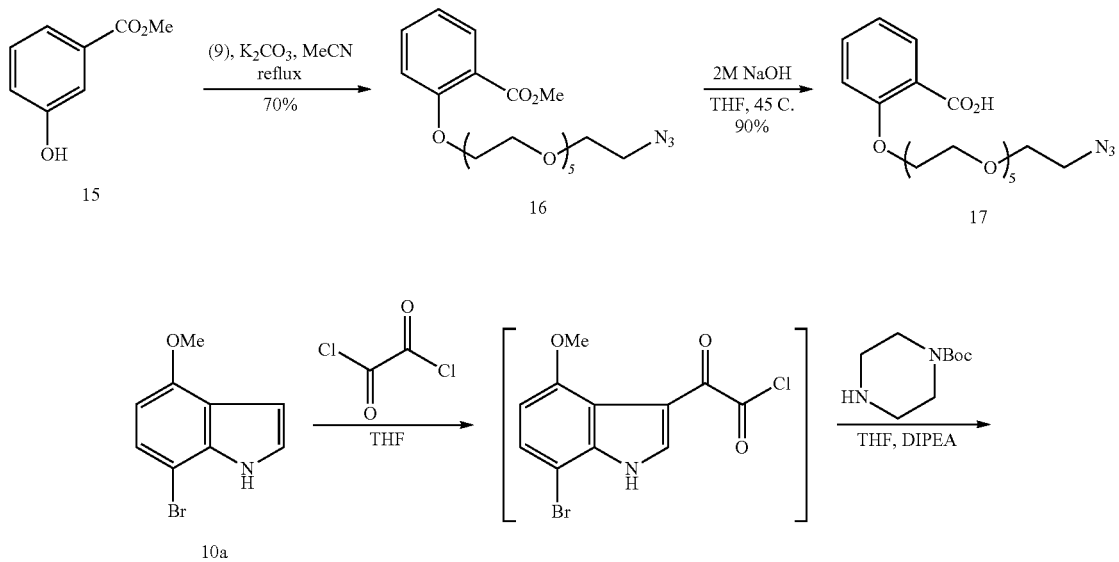

US PATENT:
US20030069245

-continued

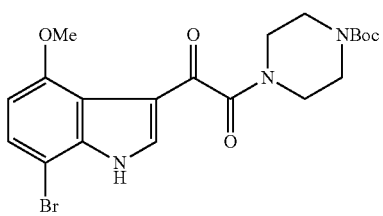

18

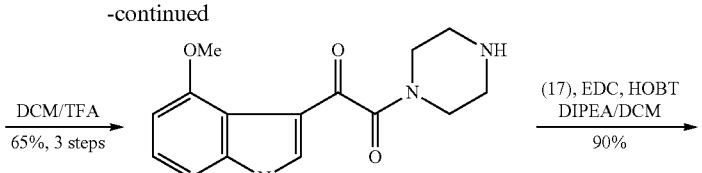

19

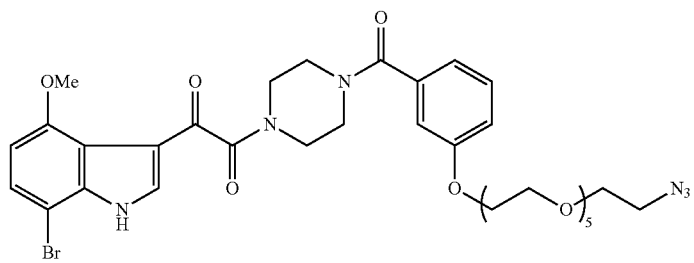

20

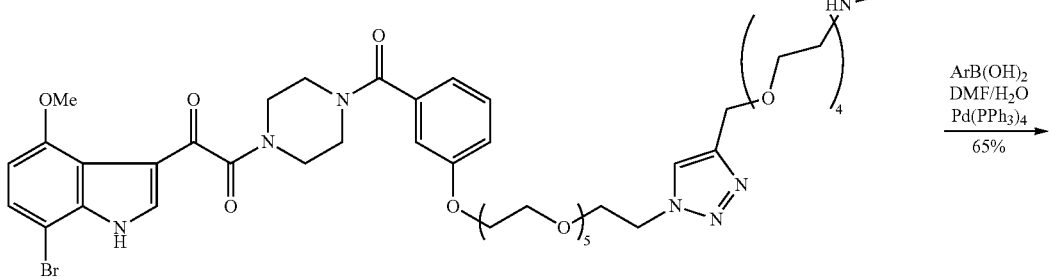

21

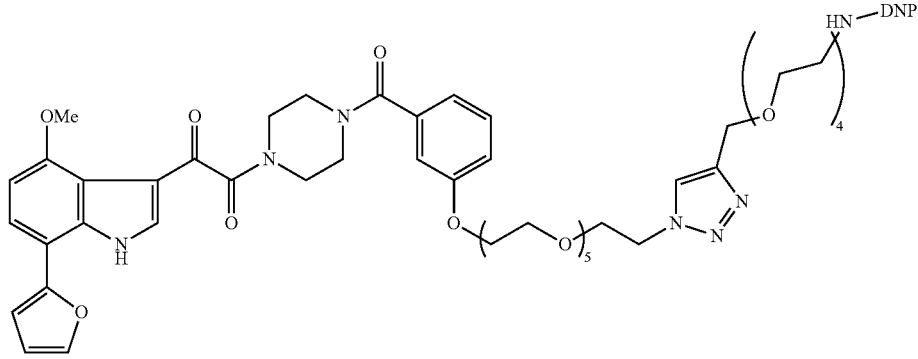

22

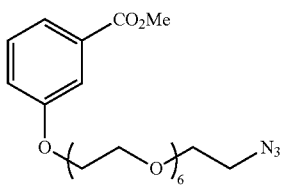

(16)

To a flame-dried flask containing a solution of methyl 3-hydroxybenzoate (190 mg, 1.25 mmol, 1.16 equiv) in anhydrous CH₃CN (10 mL), added K₂CO₃ (173 mg, 1.25 mmol, 1.16 equiv) and 9 (500 mg, 1.08 mmol). Resulting mixture was heated to reflux under an atmosphere of N₂ until TLC (5:1 Hexanes/EtOAc) indicated reaction completion (14 hrs). Reaction was quenched with saturated NH₄Cl (30 mL) and extracted with CH₂Cl₂ (3×50 mL). The combined organic layers were dried over anhyd. MgSO₄, filtered, and all solvents were evaporated. Crude 16 was purified by flash chromatography (CombiFlash Automated Chromatographer, 12 g column, dryloaded with 25 g pre-packed dry loading column. Run using 10% EtOAc:Hexanes to 50% EtOAc:Hexanes gradient over 40 column volumes, followed by EtOAc flush) to yield 16 as a clear viscous oil (331 mg, 70%). $^1$H NMR (500 MHz, CDCl₃) δ 7.64-7.57 (m, 1H), 7.54 (dd, J=1.5, 2.5, 1H), 7.31 (t, J=8.0, 1H), 7.10 (ddd, J=1.0, 2.7, 8.3, 1H), 4.19-4.10 (m, 2H), 3.88 (s, 3H), 3.86-3.82 (m, 2H), 3.73-3.57 (m, 20H), 3.40-3.33 (m, 2H).

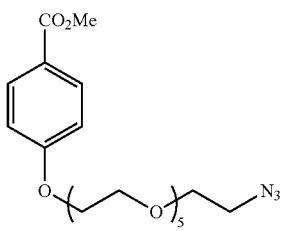

(50)

Prepared 50 in the same manner as compound 16 starting from methyl 4-hydroxybenzoate in 79% yield. 1H NMR (400 MHz, CDCl$_3$) δ 7.97 (d, J=9.0, 2H), 6.92 (d, J=9.0, 2H), 4.24-4.09 (m, 2H), 3.87 (m, 5H), 3.75-3.70 (m, 2H), 3.70-3.61 (m, 16H), 3.37 (t, J=5.0, 2H).

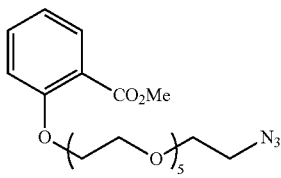

(51)

Prepared 51 in the same manner as compound 16 starting from methyl 2-hydroxybenzoate in 70% yield. 1H NMR (400 MHz, CDCl$_3$) δ 7.76 (dd, J=1.8, 7.9, 1H), 7.42 (ddd, J=1.8, 7.5, 8.4, 1H), 7.02-6.92 (m, 2H), 4.21-4.16 (m, 2H), 3.91-3.86 (m, 2H), 3.85 (s, MI), 3.77-3.71 (m, 2H), 3.69-3.58 (m, 18H), 3.37 (dd, J=4.2, 9.3, 2H).

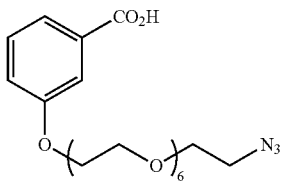

(17)

A solution of 16 (318 mg, 0.72 mmol) in THF (12 mL) and aq. NaOH (2M, 5 mL) was heated to 45° C. for 20 hrs when TLC indicated reaction completion (20:1 CH$_2$Cl$_2$/CH$_3$OH). The solution was acidified to a pH of 1 using 6M aq. HCl and then extracted with CH$_2$Cl$_2$ (3×30 mL). The combined organic layers were dried over anhyd. MgSO$_4$, filtered, and all solvents were evaporated, resulting in 17 as a clear viscous oil (280 mg, 90%), which was used without further purification. 1H NMR (400 MHz, CDCl$_3$) δ 7.67 (d, J=7.7, 1H), 7.59 (s, 1H), 7.33 (t, J=8.0, 1H), 7.13 (dd, J=1.9, 8.2, 1H), 4.21-4.12 (m, 2H), 3.91-3.82 (m, 2H), 3.74-3.69 (m, 2H), 3.69-3.58 (m, 16I), 3.40-3.29 (m, 2H).

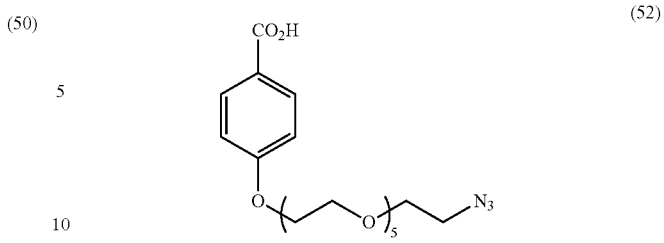

(52)

Prepared 52 in the same manner as compound 17 in 76% yield. 1H NMR (400 MHz, CDCl$_3$) δ 10.61 (broad peak, 1H), 7.66 (d, J=7.7, 1H), 7.59 (d, J=0.9, 1H), 7.33 (t, J=7.9, 1H), 7.18-7.08 (m, 1H), 4.21-4.10 (m, 2H), 3.92-3.82 (m, 2H), 3.75-3.59 (m, 18H), 3.41-3.31 (m, 2H).

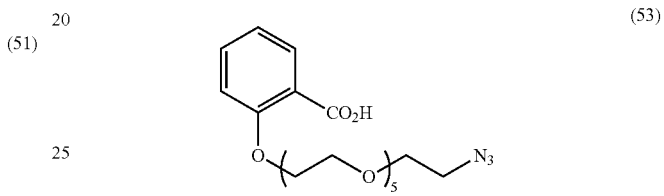

(53)

Prepared 53 in the same manner as compound 17 in 93% yield. 1H NMR (500 MHz, CDCl$_3$) δ 8.12 (dd, J=1.8, 7.8, 1H), 7.52 (ddd, J=1.8, 7.4, 8.4, 1H), 7.15-7.08 (m, 1H), 7.02 (d, J=7.9, 1H), 4.42-4.30 (m, 2H), 3.90 (dd, J=3.9, 5.2, 2H), 3.72-3.57 (m, 18H), 3.37-3.33 (m, 2H).

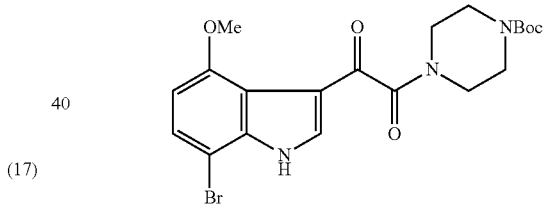

(18)

To a flame-dried flask containing 10a[5] (50.0 mg, 0.233 mmol) in anhyd. THF (600 μL), added oxalyl chloride (97 μL, 1.11 mmol, 5 equiv) and let stir under an atmosphere of N$_2$ until TLC (5:1 hexanes/EtOAc) indicated consumption of starting material (5-12 hr, depending on scale). All volatiles were removed by rotoevaporation and resulting green residue was immediately suspended in anhyd. THF (1 mL), followed by the addition of N-Boc piperazine[6] (52 mg, 0.28 mmol, 1.2 equiv) and DIPEA (78 μL, 2 equiv). Resulting mixture was stirred under an atmosphere of N$_2$ at RT for 12 hr. and then at reflux for 30 min (if needed) when TLC (5:1 hexanes/EtOAc) indicated reaction completion. Reaction was allowed to cool to RT, poured into H$_2$O (10 mL) and extracted with EtOAc (3×10 mL). The combined organic layers were dried over anhyd. MgSO$_4$, filtered, and all solvents were evaporated. Crude 18 was purified by flash chromatography (CombiFlash Automated Chromatographer, 12 g column, dryloaded with 4 g pre-packed dry loading column. Run using 100% Hexanes to 50% EtOAc: Hexanes gradient over 30 column volumes, followed by EtOAc flush) to yield 18 as a light brown powder (78 mg, 75%). $^1$H NMR (400 MHz, CDCl$_3$) δ 9.44 (s, 1H), 7.94 (d, J=3.1, 1H), 7.28 (d, J=8.5, 1H), 6.56 (d, J=8.5, 1H), 3.90 (s, 3H), 3.71 (m, 2H), 3.60-3.51 (m, 2H), 3.46 (m, 4H), 1.47 (s, 9H). (ES+) m/z (M+H)$^+$466; (M+Na)$^+$ 488; Rt=1.34.

[5]. US PATENT: US20030069245
[6]. Faust, A.; Waschkau, B.; Waldeck, J.; Holtke, C.; Breyholtz, H.; Wagner, S.; Kopka, K.; Heindel, W.; Schafer, M.; Bremer, C. *Bioconjug. Chem.* 2008, 19, 1001-1008.

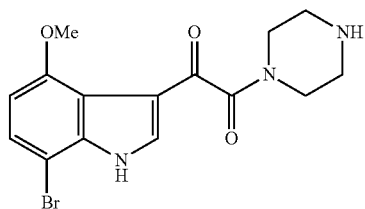

(19)

To a solution of 18 (75 mg, 0.161 mmol) in CH$_2$Cl$_2$ (1.5 mL), added trifluoroacetic acid (TFA) (0.5 mL), resulting in an immediate color change from clear to yellow. The resulting solution was stirred at RT for 30 min when TLC (20:1 CH$_2$Cl$_2$/CH$_3$OH) indicated complete starting material consumption. All volatiles were removed by rotoevaporation and residue was redissolved in CH$_2$Cl$_2$ (15 mL) and NaOH (2M, until a pH of 11 is achieved) and then extracted with CH$_2$Cl$_2$ (3×15 mL). The combined organic layers were dried over anhyd. MgSO$_4$, filtered, and all solvents were evaporated, resulting in 19 as an off-white solid (51 mg, 86%). 1H NMR (400 MHz, CDCl$_3$/CD$_3$OD (10:1)) δ 7.87 (s, 1H), 7.18 (d, J=8.4, 1H), 6.46 (d, J=8.4, 1H), 3.98 (broad peak, 3H), 3.78 (s, 3H), 3.60 (broad peak, 2H), 3.33 (broad peak, 2H), 2.86 (broad peak, 2H), 2.75 (broad peak, 2H).

Method 4: Coupling of Piperazines to Benzoic Acids (Synthesis of 20 Shown as Example).

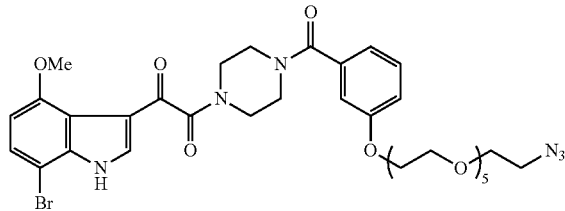

(20)

To a flame-dried flask containing a solution of 19 (20 mg, 0.055 mmol) in CH$_2$Cl$_2$ (2 mL), added 17 (25.8 mg, 0.06 mmol, 1.1 equiv), EDC-HCl (11.5 mg, 0.06 mmol, 1.1 equiv), HOBT (9.2 mg, 0.06 mmol, 1.1 equiv) and DIPEA (30 uL, 0.16 mmol, 3 equiv). Resulting mixture was stirred at RT under an atmosphere of N$_2$ at RT for 8 hr when TLC (9:1 CH$_2$Cl$_2$/CH$_3$OH) indicated reaction completion. Mixture was diluted with CH$_2$Cl$_2$ (10 mL) and washed with sat. NaHCO$_3$ (15 mL), sat. NH$_4$Cl (15 mL) and brine (15 mL). The combined organic layers were dried over anhyd. MgSO$_4$, filtered, and all solvents were evaporated, resulting in crude 20 as a sticky solid. Crude 20 was purified by flash chromatography (CombiFlash Automated Chromatographer, 4 g column, dryloaded with 4 g pre-packed dry loading column. Run using 100% CH$_2$Cl$_2$ to 10% CH$_3$OH in CH$_2$Cl$_2$ gradient over 40 column volumes) to yield 20 as a clear sticky solid (38 mg, 90%). $^1$H NMR (400 MHz, CDCl$_3$) δ 9.66 (s, 1H), 7.96 (d, J=3.1, 1H), 7.34 (broad peak, 1H), 7.29 (d, J=8.4, 1H), 6.96 (broad peak, J=7.5, 3H), 6.57 (d, J=8.5, 1H), 4.12 (broad peak, 2H), 3.91 (s, 3H), 3.84 (s, 4H), 3.74-3.39 (m, 24H), 3.36 (t, J=5.0, 2H). $^{13}$C NMR (125 MHz, CDCl$_3$) δ 186.43, 170.83, 167.67, 159.35, 153.86, 136.96, 136.68, 134.98, 130.25, 127.23, 119.67, 116.84, 116.65, 116.07, 113.72, 105.24, 97.15, 71.20, 71.06, 71.04, 70.99, 70.95, 70.40, 70.01, 68.00, 56.54, 51.06.

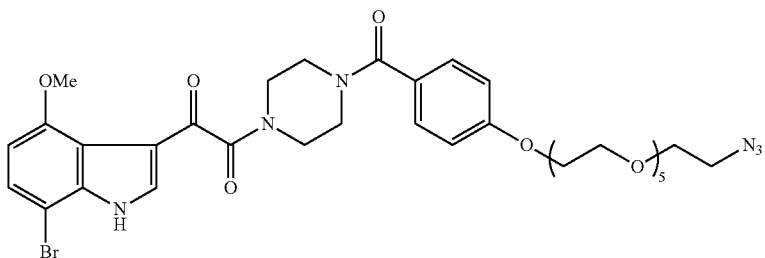

(54)

Prepared 54 in the same manner as compound 20 in 88% yield. 1H NMR (400 MHz, CDCl$_3$) δ 9.72 (s, 1H), 7.95 (s, 1H), 7.38 (d, J=8.6, 2H), 7.28 (d, J=8.4, 1H), 6.91 (d, J=8.6, 2H), 6.56 (d, J=8.6, 1H), 4.18-4.10 (m, 2H), 3.90 (s, 3H), 3.87-3.81 (m, 2H), 3.80-3.41 (m, 26H), 3.40-3.32 (m, 2H).

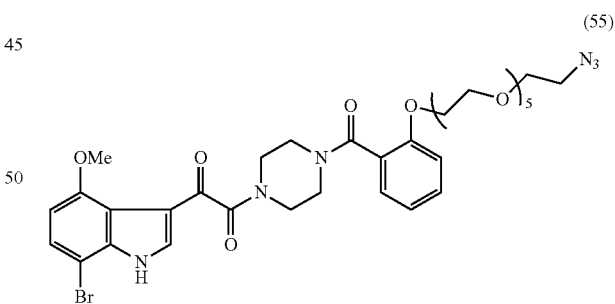

(55)

Prepared 55 in the same manner as compound 20 in 81% yield. 1H NMR (400 MHz, CDCl$_3$) δ 9.11 (d, J=2.6, 1H), 8.78 (s, 1H), 8.23 (dd, J=2.4, 9.5, 1H), 7.68 (s, 1H), 7.41-7.14 (m, 1H), 7.09-6.72 (m, 2H), 6.41 (s, 1H), 4.64 (s, 2H), 4.41 (s, 2H), 4.29-3.98 (m, 2H), 3.92-3.05 (m, 27H).

(21) Prepared according to Method 2 as in compound 4 using 15 mg (0.019 mmol) of 20 with 17 (14 mg, 0.035 mmol, 1.8 equiv). Crude 21 purified by flash column chromatography (100% CH$_2$Cl$_2$→20:1 CH$_2$Cl$_2$/CH$_3$OH→10:1 CH$_2$Cl$_2$/CH$_3$OH), resulting in 21 as a sticky yellow solid (20 mg, 90%). 1H NMR (400 MHz, CDCl$_3$) δ 10.37 (s, 1H), 9.04 (d, J=2.6, 1H), 8.73 (broad peak, 1H), 8.18 (dd, J=2.6, 9.5, 1H), 7.96 (d, J=1.7, 2H), 7.69 (s, 1H), 7.28 (m, 1H), 7.24 (d, J=8.5, 2H), 6.92 (m, 3H), 6.89 (d, J=9.6, 1H), 6.52 (d, J=8.5, 1H), 4.62 (s, 2H), 4.47 (t, J=5.0, 2H), 4.09 (broad peak, 4H), 3.87 (s, 3H), 3.85-3.71 (m, 14H), 3.71-3.29 (m, 28H). 13C NMR (125 MHz, CDCl$_3$) δ 185.98, 170.34, 167.19, 158.88, 153.44, 148.35, 144.70, 136.58, 136.30, 135.90, 134.82, 130.32, 130.12, 129.81, 126.75, 124.13, 123.84, 119.24, 116.35, 116.12, 115.66, 114.16, 113.23, 104.72, 96.72, 70.76, 70.63, 70.58, 70.54, 70.52, 70.50, 70.46, 70.45, 70.41, 69.58, 69.56, 69.35, 68.52, 67.56, 64.45, 56.08, 50.16, 43.19.

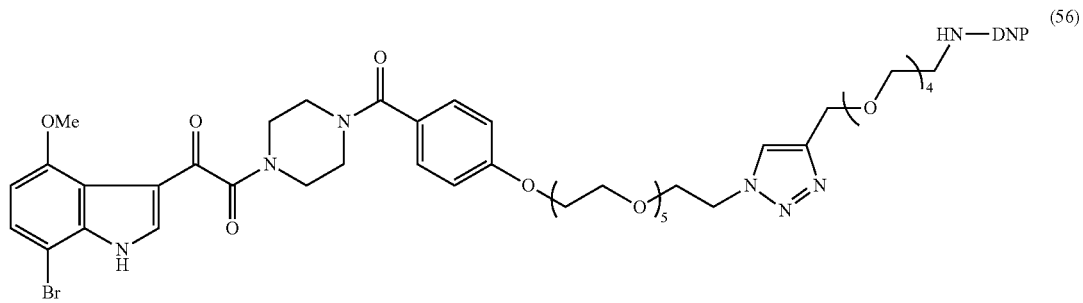

(56)

Prepared according to Method 2 as in compound 4. Crude 56 purified by flash column chromatography (100% CH$_2$Cl$_2$→20:1 CH$_2$Cl$_2$/CH$_3$OH→10:1 CH$_2$Cl$_2$/CH$_3$OH), resulting in 56 as a sticky yellow solid in 73% yield. 1H NMR (400 MHz, CDCl$_3$) δ 10.59 (two singlet, J=62.6, 1H), 9.09 (d, J=2.6, 1H), 8.76 (s, 1H), 8.30-8.12 (m, 1H), 8.01 (s, 1H), 7.47-7.20 (m, 4H), 7.11-6.77 (m, 3H), 6.57 (dd, J=8.5, 12.4, 1H), 4.63 (s, 2H), 4.43 (s, 2H), 4.20-3.99 (m, 4H), 3.92 (2 singlets, J=14.4, 1H), 3.87-3.16 (m, 42H).

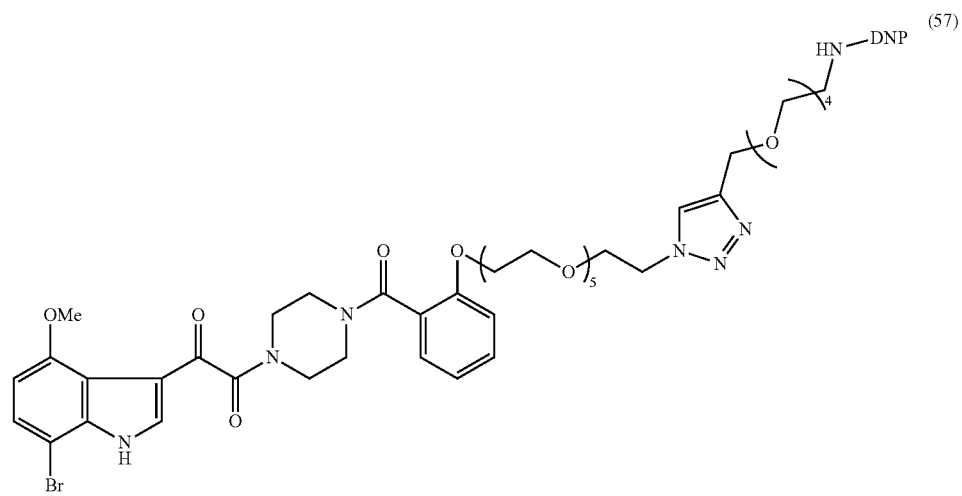

(57)

Prepared according to Method 2 as in compound 4. Crude 57 purified by flash column chromatography (100% CH$_2$Cl$_2$→20:1 CH$_2$Cl$_2$/CH$_3$OH→10:1 CH$_2$Cl$_2$/CH$_3$OH), resulting in 57 as a sticky yellow solid in 90% yield. 1H NMR (400 MHz, CDCl$_3$) δ 10.59 (two singlets, 1H), 9.09 (d, J=2.6, 2H), 8.76 (s, 2H), 8.32-8.15 (m, 2H), 8.01 (s, 2H), 7.40-7.27 (m, 5H), 7.24 (d, J=1.4, 1H), 7.08-6.73 (m, 6H), 6.57 (dd, J=8.5, 12.4, 2H), 4.63 (s, 3H), 4.43 (s, 4H), 4.10 (dd, J=17.4, 56.7, 7H), 3.92 (d, J=14.4, 6H), 3.86-3.15 (m, 94H). UPLC/MS: (ES+) m/z (M+H)$^+$ 1173; (M+Na)$^+$ 1195; Rt=1.51.

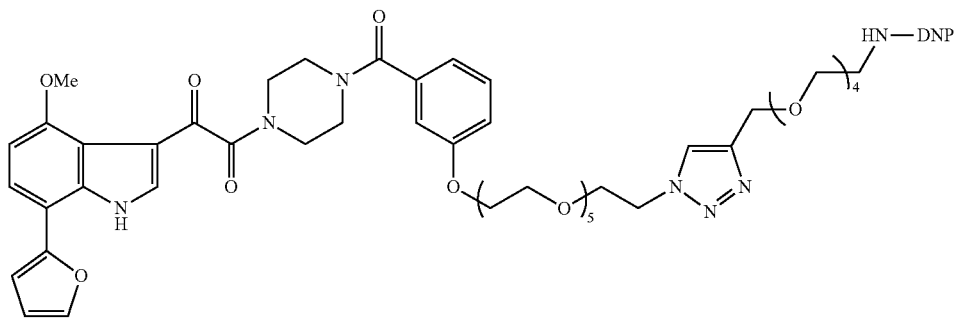

(22)

Prepared according to Method 3 as in compound 14 using 21 (15 mg, 0.017 mmol). Crude 22 was purified by HPLC (0-60% B gradient, 46 min run time), resulting in 22 as a sticky yellow solid (12.7 mg, 64%). $^1$H NMR (500 MHz, CDCl$_3$) δ 10.21 (s, 1H), 9.09 (d, J=2.6, 1H), 8.77 (broad peak, 1H), 8.21 (dd, J=2.5, 9.5, 1H), 8.08 (d, J=3.1, 1H), 7.71 (broad peak, 1H), 7.55 (s, 1H), 7.45 (d, J=8.3, 1H), 7.30 (broad peak, 1H), 6.95 (broad peak, 3H), 6.91 (d, J=9.5, 1H), 6.71 (d, J=8.2, 1H), 6.67 (d, J=3.3, 1H), 6.54 (dd, J=1.8, 3.3, 1H), 4.64 (s, 2H), 4.50 (broad peak, 2H), 4.12 (broad peak, 4H), 3.95 (s, 3H), 3.92-3.75 (m, 12H), 3.74-3.31 (m, 30H). $^{13}$C NMR (125 MHz, CDCl$_3$) δ 154.10, 153.38, 148.82, 141.67, 136.77, 136.40, 134.87, 134.45, 130.84, 130.59, 130.25, 124.62, 124.17, 124.15, 121.54, 119.73, 116.85, 115.87, 115.62, 114.56, 113.72, 112.25, 109.85, 104.95, 104.45, 100.39, 71.08, 71.03, 70.90, 70.87, 70.79, 70.74, 70.68, 70.65, 69.98, 69.92, 69.77, 69.01, 68.01, 64.69, 56.41, 50.64, 50.64, 43.55. UPLC/MS: (ES+) m/z (M+H)$^+$ 1160, (M+Na)$^+$ 1182; Rt=1.55.

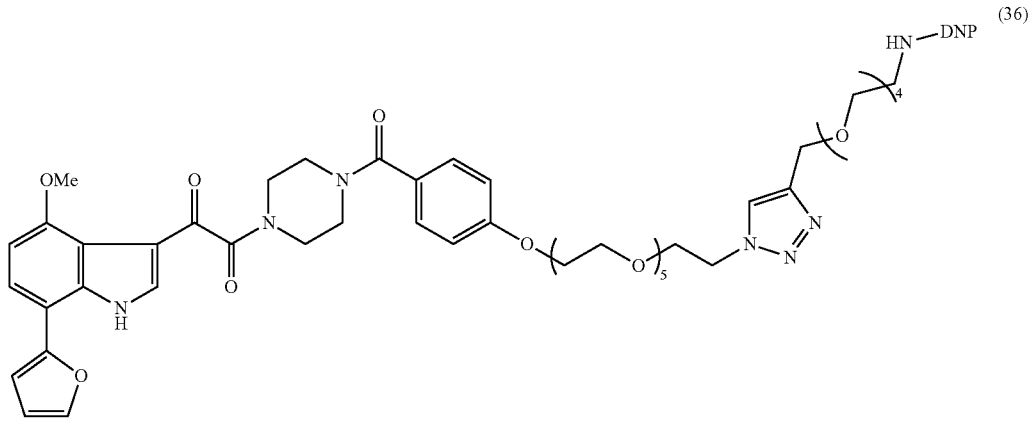

(36)

Prepared according to Method 3 as in compound 14 using Crude 36 was purified by HPLC (0-60% B gradient, 46 min run time), resulting in 36 as a sticky yellow solid in 50% yield. $^1$H NMR (500 MHz, CDCl$_3$) δ 10.13 (s, 1H), 9.10 (d, J=2.6, 1H), 8.77 (s, 1H), 8.23 (dd, J=2.5, 9.5, 1H), 8.08 (d, J=2.3, 1H), 7.74 (s, 1H), 7.55 (s, 1H), 7.45 (d, J=8.3, 1H), 7.39 (d, J=8.3, 2H), 6.93 (apparent d, J=9.3, 3H), 6.72 (d, J=8.4, 1H), 6.67 (d, J=3.4, 1H), 6.55 (dd, J=1.8, 3.4, 1H), 4.66 (s, 2H), 4.51 (s, 2H), 4.14 (s, 2H), 3.95 (s, 3H), 3.90-3.74 (m, 12H), 3.73-3.30 (m, 32H). UPLC/MS: (ES+) m/z (M+H)$^+$ 1160; (M+Na)$^+$ 1182; Rt=1.53.

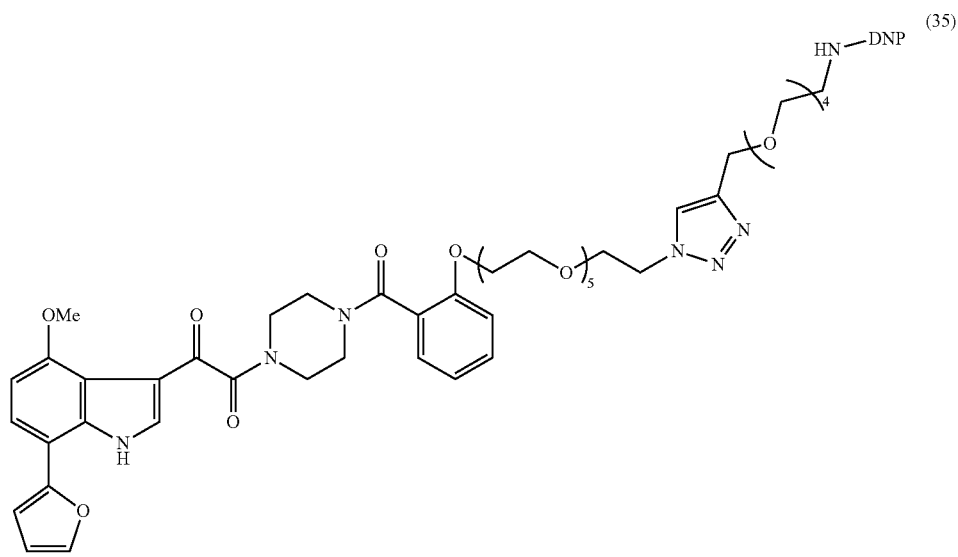

Prepared according to Method 3 as in compound 14. Crude 35 was purified by HPLC (0-60% B gradient, 60 min run time), resulting in 35 as a sticky yellow solid in 53% yield. $^1$H NMR (500 MHz, CDCl$_3$) δ 10.48 (two singlets, J=50.2, 1H), 9.10 (d, J=2.6, 1H), 8.77 (s, 1H), 8.22 (dd, J=2.5, 9.5, 1H), 8.08 (t, J=2.8, 1H), 7.73 (d, J=6.8, 1H), 7.54 (dd, J=1.2, 8.4, 1H), 7.46 (dd, J=8.3, 10.3, 1H), 7.41-7.28 (m, 2H), 7.02 (two triplets, J=7.5, 25.4, 1H), 6.96-6.84 (m, 2H), 6.73 (dd, J=8.4, 12.8, 1H), 6.68 (t, J=3.8, 1H), 6.54 (ddd, J=1.8, 3.4, 5.3, 1H), 4.65 (s, 2H), 4.49-4.40 (m, 2H), 4.29-3.99 (m, 4H), 3.97 (d, J=11.5, 3H), 3.88-3.20 (m, 42H) (Note: Broadened/doubled signals coalesce upon heating). UPLC/MS: (ES+) m/z (M+H)$^+$ 1160; (M+Na)$^+$ 1182; Rt=1.57.

Supplementary Scheme 6. Representative Synthesis of ARM—H type (26) molecules

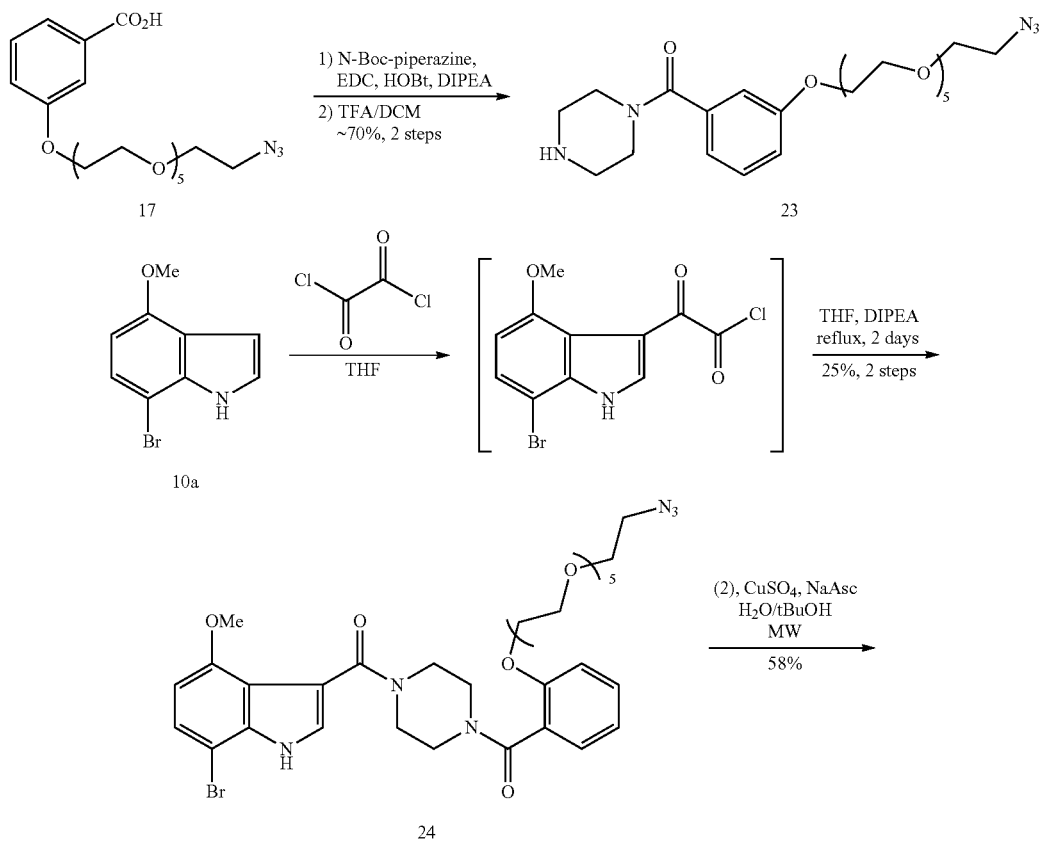

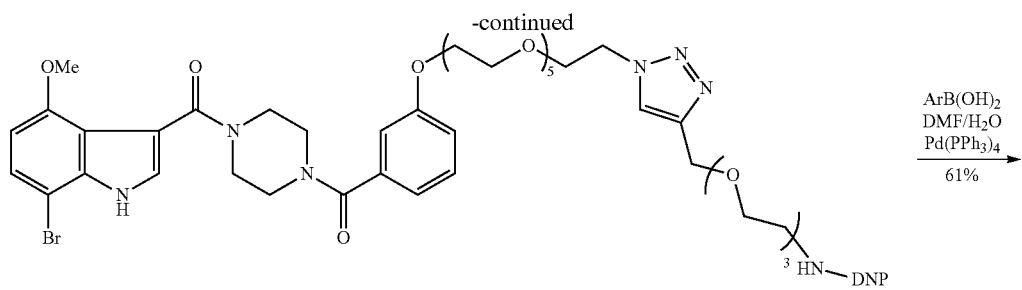

25

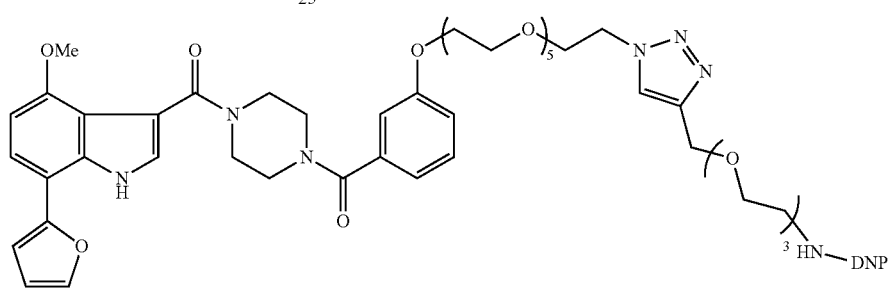

26

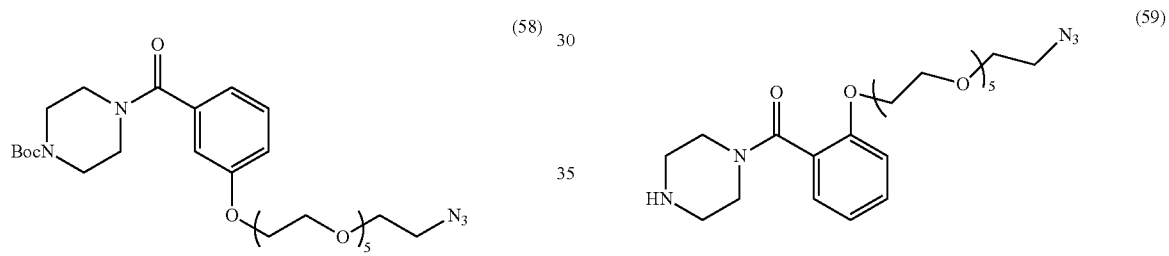

(58)

Prepared according to Method 4 as in compound 20 from 17 and N-Boc-piperazine. Crude 58 was purified by flash column chromatography (1:1 hexanes/EtOAc→1:5 hexanes/EtOAc→100% EtOAc), resulting in 58 as a colorless oil (70%). 1H NMR (400 MHz, CDCl$_3$) δ 7.30 (t, J=8.1, 1H), 7.02-6.84 (m, 3H), 4.18-4.08 (m, 2H), 3.90-3.82 (m, 2H), 3.78-3.55 (m, 20H), 3.54-3.25 (m, 8H), 1.46 (s, 9H).

(23)

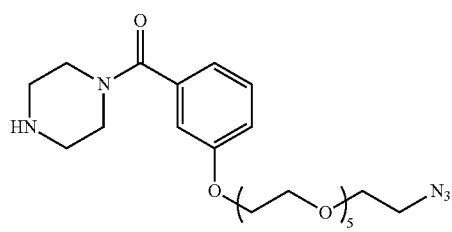

Prepared 23 in the same manner as compound 19 in from 58 75% yield as a clear oil. 1H NMR (400 MHz, CDCl$_3$) δ 7.31-7.25 (m, 1H), 6.93 (m, 3H), 4.17-4.04 (m, 2H), 3.87-3.81 (m, 2H), 3.77-3.56 (m, 18H), 3.42-3.27 (m, 2H), 2.91 (s, 1H).

(59)

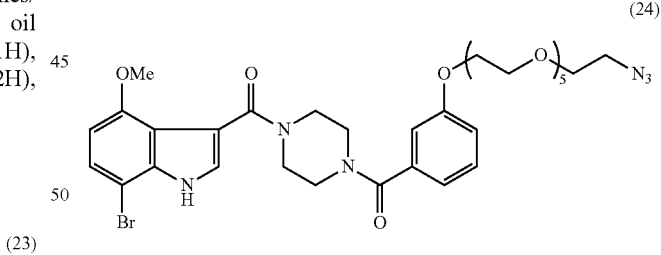

Prepared 59 in the same manner as compound 23, starting from 53 and N-Boc-piperazine. Isolated as a clear oil.

(24)

To a flame-dried flask containing 10a (17 mg, 0.0744 mmol) in anhyd. THF (500 pit), added oxalyl chloride (33 μL, 0.37 mmol, 5 equiv) and let stir under an atmosphere of N$_2$ until TLC (5:1 hexanes/EtOAc) indicated consumption of starting material (5-12 hr, depending on scale). All volatiles were removed by rotoevaporation and resulting green residue was immediately suspended in anhyd. THF (1 mL), followed by the addition of 23 (37 mg, 0.28 mmol, 1.2 equiv) and DIPEA (34 μL). The resulting orange mixture was stirred under an atmosphere of N$_2$ at reflux for 8 hr when TLC (9:1 CH$_2$Cl$_2$/CH$_3$OH) indicated reaction completion. Reaction was allowed to cool to RT, poured into H$_2$O (5 mL) and extracted with EtOAc (3×15 mL). The combined organic layers were dried over anhyd. MgSO$_4$, filtered, and all solvents were evaporated. Crude 24 was purified by flash column chromatography (1:1 hexanes/EtOAc→1:5 hexanes/EtOAc→100% EtOAc), resulting in 24 as a sticky solid (14 mg, 25%). 1H NMR (400 MHz, CDCl$_3$) δ 8.59 (s, 1H), 7.32 (m, 2H), 6.95 (broad peak, 3H), 6.48 (d, J=8.7, 1H), 4.13 (s, 2H), 3.89 (s, 3H), 3.85 (broad peak, 2H), 3.76-3.58 (m, 24H), 3.40-3.35 (m, 4H). UPLC/MS: (ES+) m/z (M+H)$^+$ 747; (M+Na)$^+$ 769; Rt=1.28.

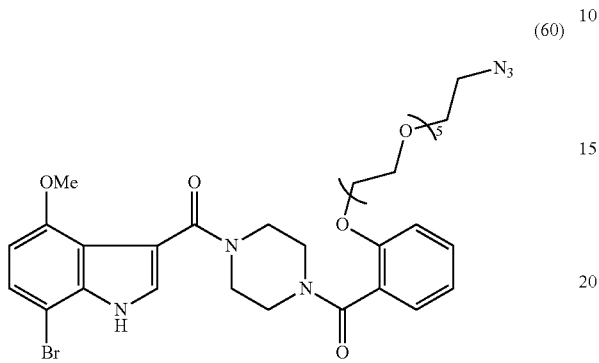
(60)

Prepared 60 in the same manner as compound 24 in 79% yield starting from 10a and 59. UPLC/MS: (ES+) m/z (M+H)$^+$ 747; (M+Na)$^+$ 769; Rt=1.33

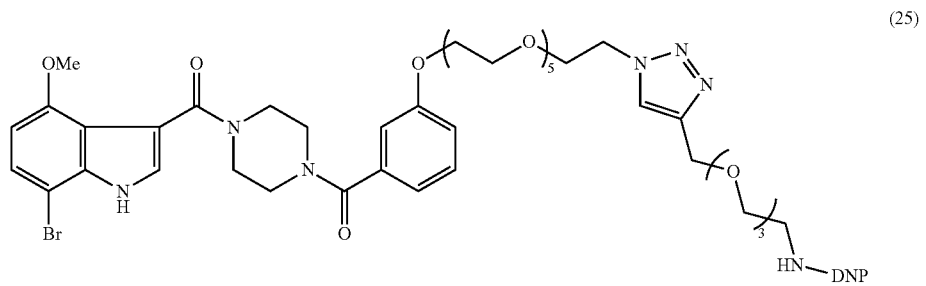
(25)

Prepared according to Method 2 as in compound 4. Crude 25 purified by flash column chromatography (100% CH$_2$Cl$_2$→20:1 CH$_2$Cl$_2$/CH$_3$OH→10:1 CH$_2$Cl$_2$/CH$_3$OH), resulting in 25 as a sticky yellow solid in 58% yield. 1H NMR (400 MHz, CDCl$_3$) δ 9.12 (d, J=2.7, 1H), 8.78 (s, 2H), 8.24 (d, J=9.5, 1H), 7.72 (s, 1H), 7.33 (m, 2H), 6.94 (m, 5H), 6.47 (s, 1H), 4.65 (s, 2H), 4.51 (t, J=5.0, 2H), 4.13 (s, 2H), 3.89 (s, 3H), 3.83 (m, 8H), 3.74-3.52 (m, 36H). UPLC/MS: (ES+) m/z (M+H)$^+$ 1146; (M+Na)$^+$ 1168; Rt=1.51.

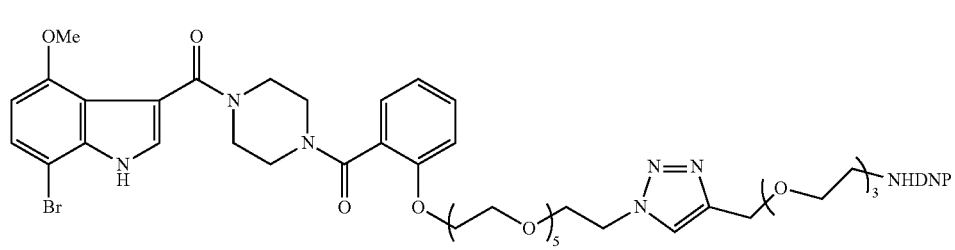
(61)

Prepared according to Method 2 as in compound 4. Crude 61 purified by flash column chromatography (100% CH₂Cl₂→20:1 CH₂Cl₂/CH₃OH→10:1 CH₂Cl₂/CH₃OH), resulting in 61 as a sticky yellow solid in 90% yield. 1H NMR (400 MHz, CDCl₃) δ 10.40 (s, 1H), 10.19 (s, 1H), 8.00 (dd, J=3.3, 4.9, 2H), 7.4-7.24 (m, 4H), 7.03 (t, J=7.4, 1H), 6.97 (d, J=7.4, 1H), 6.91 (d, J=8.3, 1H), 6.82 (d, J=8.3, 1H), 6.61 (d, J=8.5, 1H), 6.57 (d, J=8.5, 1H), 4.25-3.98 (m, 8H), 3.95 (s, 3H), 3.91 (s, 3H), 3.87-3.16 (m, 39H) (Note: Broadened/doubled signals coalesce upon heating). UPLC/MS: (ES+) m/z (M+H)⁺ 1146; (M+Na)⁺ 1168; Rt=1.52.

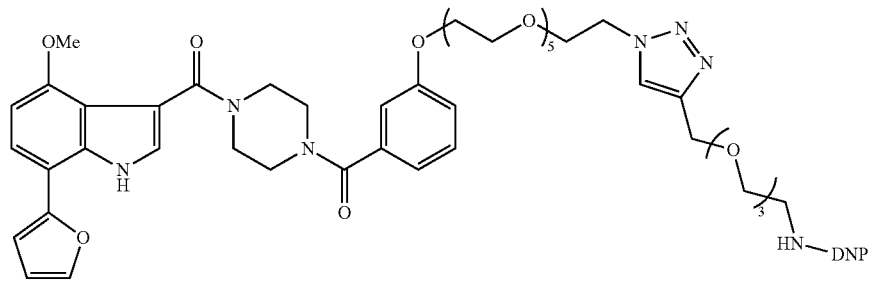

(26)

Prepared according to Method 3 as in compound 14. Crude 26 was purified by HPLC (0-60% B gradient, 60 min run time), resulting in 26 as a sticky yellow solid in 61% yield. ¹H NMR (400 MHz, CDCl₃) δ 9.57 (s, 1H), 9.12 (d, J=2.6, 1H), 8.86-8.72 (broad signal, 1H), 8.23 (s, 1H), 7.74 (s, 1H), 7.55 (s, 1H), 7.42 (s, 2H), 6.94 (m, 4H), 6.72-6.38 (m, 3H), 4.66 (broad signal, 2H), 4.51 (broad signal, 2H), 4.12 (broad signal, 2H), 3.93 (s, 3H), 3.83 (d, J=13.9, 8H), 3.74-3.27 (m, 36H). UPLC/MS: (ES+) m/z (M+H)⁺ 1132; (M+Na)⁺ 1154; Rt=1.58

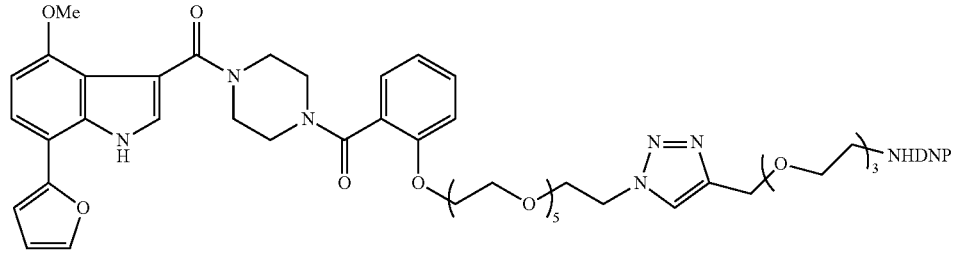

(62)

Prepared according to Method 3 as in compound 14. Crude 62 was purified by HPLC (0-60% B gradient, 60 min run time), resulting in 62 as a sticky yellow solid in 59% yield. ¹H NMR (400 MHz, CDCl₃) δ 9.74 (broad peak, 1H), 9.11 (d, J=2.5, 1H), 8.77 (s, 1H), 8.23 (d, J=9.3, 1H), 7.67 (s, 1H), 7.44 (m, 5H), 6.89 (m, 3H), 6.58 (m, 3H), 4.64 (s, 2H), 4.43-4.04 (m, 8H), 3.91 (s, 3H), 3.82-3.76 (m, 8H), 3.70-3.40 (m, 32H) (Note: Broadened/doubled signals coalesce upon heating). UPLC/MS: (ES+) m/z (M+H)⁺ 1132, (M+Na)⁺ 1154; Rt=1.59.

Supplementary Scheme 7. Representative Synthesis of ARM—H type (38) molecules
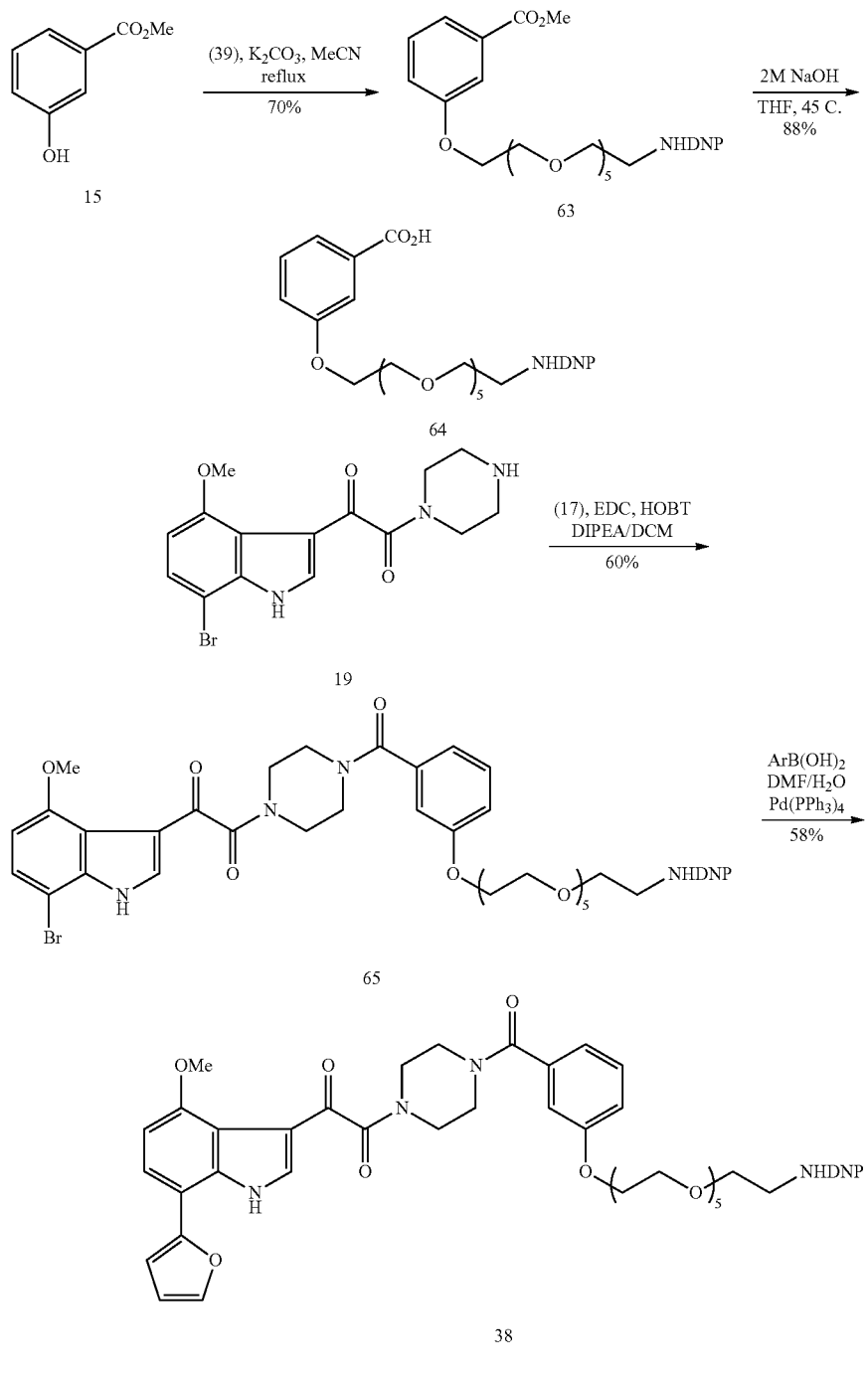
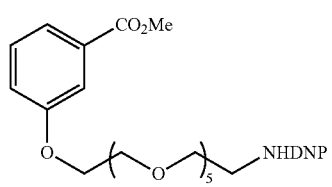
(63)
Prepared 63 in the same manner as compound 16 starting from methyl 4-hydroxybenzoate and 39 in 70% yield as a yellow oil. 1H NMR (400 MHz, CDCl$_3$) δ 9.13 (d, J=1.9, 1H), 8.79 (s, 1H), 8.25 (dd, J=2.5, 9.5, 1H), 7.79 (d, J=8.1, 1H), 7.55 (s, 1H), 7.32 (t, J=8.3, 1H), 7.11 (dd, J=2.7, 8.3, 1H), 6.94 (d, J=9.5, 1H), 4.15 (m, 2H), 3.90 (s, 3H), 3.82 (t, J=5.3, 2H), 3.75-3.52 (m, 20H).

(64)

Prepared 64 in the same manner as compound 17 in 86% yield as a yellow oil. 1H NMR (400 MHz, CDCl$_3$) δ 9.11 (d, J=2.7, 1H), 8.85-8.70 (m, 1H), 8.24 (d, J=9.5, 1H), 7.65 (d, J=7.6, 1H), 7.60 (s, 1H), 7.33 (t, J=7.9, 1H), 7.14 (s, 1H), 6.93 (d, J=9.5, 1H), 4.23-4.15 (m, 2H), 3.90-3.83 (m, 2H), 3.81 (t, J=5.3, 2H), 3.75-3.55 (m, 18).

(65)

Prepared 65 in the same manner as compound 20 in 60% yield as a yellow residue. 1H NMR (400 MHz, CDCl$_3$) δ 9.64 (s, 1H), 9.08 (d, J=2.5, 1H), 8.75 (s, 1H), 8.21 (d, J=9.5, 1H), 7.98 (s, 1H), 7.29 (d, J=8.4, 2H), 7.03-6.85 (m, 4H), 6.56 (d, J=8.5, 1H), 4.11 (s, 2H), 3.90 (s, 3H), 3.79 (m, 6H), 3.73-3.59 (m, 20H), 3.55 (m, 4H).

(38)

Prepared according to Method 3 as in compound 14. Crude 38 was purified by HPLC (0-60% B gradient, 46 min run time), resulting in 38 as a sticky yellow solid in 58% yield. $^1$H NMR (400 MHz, CDCl$_3$) δ 10.07 (s, 1H), 9.09 (s, 1H), 8.76 (s, 1H), 8.23 (d, J=9.5, 1H), 8.09 (s, 1H), 7.56 (s, 1H), 7.45 (d, J=8.3, 1H), 7.36-7.28 (m, 1H), 6.96 (broad peak, 3H), 6.91 (d, J=9.8, 1H), 6.72 (d, J=8.5, 1H), 6.67 (s, 1H), 6.55 (s, 1H), 4.13 (s, 2H), 3.96 (s, 3H), 3.84 (s, 3H), 3.79 (m, 3H), 3.74-3.41 (m, 24H). HRMS (EI) m/z (%) for C$_{44}$H$_{50}$N$_6$O$_{15}$ (MH+) calc'd 903.3413. found 903.3472.

MT-2 Cell Assay (FIG. 2b and FIGS. 3a and b)

Antiviral activity and cellular toxicity were determined using the MTT colorimetric method[7,8]. MT-2 cell[9,10] at a concentration of 1×10$^5$ cells per milliliter were infected with wild-type HIV IIIB[11,12,13] at a multiplicity of infection (MOI) of 0.1. Infected and mock-infected cells were incubated in growth medium (RPMI 1640, 10% δFBS, kanamycin) for 5 days with varying concentrations of each compound being tested in triplicate in a 96-well plate. MIT (thiazolyl blue tetrazolium bromide), a cell-permeable tetrazolium dye was then added to each well. Active mitochondria reduce the yellow tetrazolium salt to a blue formazan precipitate. After 5 h, stop solution (86% isopropanol, 4% NP-40, 10% H$_2$O, and 0.3% concentrated HCl) was added to lyse the cells and stop the reaction. The plates were gently shaken gently overnight on a horizontal rotator, and quantitated the following morning. Cell viability was measured spectrophotometrically by quantifying the amount of purple precipitate via determining the absorbance at 595 nm using a Multiskan Plus from Labsystems (Helsinki, Finland) microplate reader. The average of these triplicate samples was then plotted versus inhibitor concentration to generate dose-response curves. The 50% effective concentration (EC$_{50}$) and 50% cytotoxic concentration (CC$_{50}$) of the compounds were defined as the concentrations required to inhibit viral replication and to reduce the number of viable cells by 50%, respectively. Positive controls were done during each set of experiments using d4T and the appropriate parent NNRTI (HI-236 or TMC-derivative). Data were quantitated using KaleidaGraph (Synergy Software).

[7]. Mosmann, T. *J. Immunol Methods* 1983, 65, 55-63.
[8]. Pannecouque, C.; Daelemans, D.; Clercq, E. D. *Nat Protoc.* 2008, 3, 427-434.
[9]. Haertle, T.; Carrera, C. J.; Wasson, D. B.; Sowers, L. C.; Richman, D. D.; Carson, D. A. *J. Biol Chem.* 1988, 263, 5870-5875.
[10]. Harada, S.; Koyanagi, Y.; Yamamoto, N. *Science* 1985, 229, 563-566.
[11]. Popovic, M.; Read-Connole, E.; Gallo, R. C. *Lancet* 1984, 2 1472-1473.
[12]. Popovic, M.; Samgadharan, M. G.; Read, E.; Gallo, R. C. *Science* 1984, 224, 497-500.
[13]. Ratner, L.; Haseltine, W.; Patarca, R.; Livak, K. J.; Starcich, B.; Josephs, S. F; Doran, E. R.; Rafalski, J. A.; Whitehorn, E. A.; Baumeister, K.; et al. *Nature* 1985, 313, 277-284.

CD4 Inhibition ELISA (FIG. 2A)

This procedure was adapted from the protocol reported by Lin, et al.[14]. 96 well plates (Nunc; Immuno) were coated overnight at 4° C. with soluble recombinant HIV-1 gp120$_{JRFL}$ (Immune Technology; Yonkers, N.Y.) at 1 μg/ml in 0.05M Buffer A (carbonate/bicarbonate, pH=9.6, Aldrich). Plates were washed with PBS (Aldrich, 1×100 μL) and then blocked with 3% nonfat milk in phosphate buffered saline solution (PBS, Aldrich) for 1 hr at room temperature. After washing with Buffer B (50 mM Tris HCl, 100 mM NaCl, 0.05% Tween-20, pH 7.4), varying concentrations of the inhibitor were added simultaneously with recombinant human T-cell CD4 (ImmunoDiagnostics, Inc; Woburn, Mass.) in Buffer C (50 mM Tris HCl, 100 mM NaCl, 1% BSA, pH 7.4) so that the final concentration/well of CD4 is 0.1 μg/mL and plates were incubated for 1 hr at room temperature. Plates were washed with Buffer B (3×100 μL) and then incubated with mouse OKT4 anti-CD4 IgG antibody (Biolegend; San Diego, Calif.) at 0.36 μg/ml in Buffer C at RT for 1 hr. Following washes with Buffer B, plates were incubated with horse radish peroxidase (HRP)-conjugated goat anti-mouse antibody (1:2500; Biolegend; San Diego, Calif.). Bound antibody was detected with 3,3,5,5-tetramethylbenzidine (TMB, Pierce Protein Research Products), the chromogenic substrate for HPR, and absorbance was read at 450 nm. The mean (±SD) of these triplicate samples was then plotted versus inhibitor concentration and a non-linear fit curve was generated using GraphPad Prism. The 50% inhibitory concentration (IC$_{50}$) was defined as the concentration of inhibitor to reduce the amount of bound CD4 to sgp120 by 50% of the maximum bound.

[14]. Ho, H.; Fan, L.; Nowicka-Sans, B.; McAuliffe, B.; Li, C.; Yamanaka, G.; Lin, P.; et al. *J. Vir.* 2006, 80, 4017-4025.

Figures 4A, 4B:
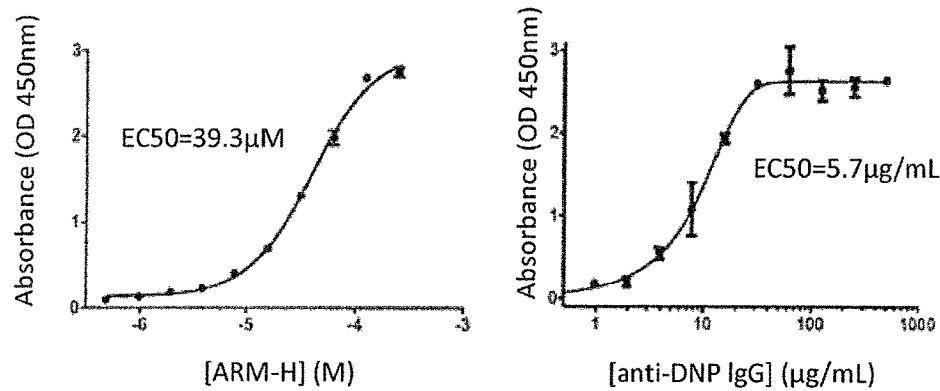
FIG. 4A shows the results of an ELISA showing ARM-H concentration dependent increase in absorbance when anti-DNP antibodies are allowed to bind to a complex of ARM-H and gp120.
FIG. 4B shows the results of an ELISA showing an anti-DNP IgG concentration dependent increase in absorbance when allowed to bind to complexed ARM-H and gp120. Raw absorbance data reported ±SD.

Anti-DNP IgG Recruiting ELISA's (FIG. 4)
A. Varying ARM-H Concentration (FIG. 4A)

Nunc-Immuno 96-well plates were coated with soluble gp120 and blocked as described above. After the PBS (Aldrich) wash, varying concentrations of ARM-H (4) were added to the plate and incubated for 1 hr at RT. After washing (3×100 µL) the plate with Buffer D (50 mM Tris HCl, 100 mM NaCl, 23 mM HEPES, 1 mM $MgCl_2$, 1 mM $CaCl_2$, pH 7.4), wells were incubated with rat monoclonal anti-dinitrophenyl (anti-DNP) IgG antibodies (Zymed; Carlsbad, Calif.) at 5 µg/ml in Buffer E (50 mM Tris HCl, 100 mM NaCl, 23 mM HEPES, 1 mM $MgCl_2$, 1 mM $CaCl_2$, 1% BSA, pH 7.4) at room temperature for 1 hr. Plates were then washed, and incubated with HRP-conjugated goat anti-rat antibody (1:2000; Novus Biologicals; Littleton, Colo.). Bound antibody was detected with 3,3,5,5-tetramethylbenzidine (TMB; Pierce Protein Research Products), and the absorbance was read at 450 nm. The mean (±SD) of these triplicate samples was then plotted versus inhibitor concentration and a non-linear fit curve was generated using GraphPad Prism. The 50% effective concentration ($EC_{50}$) was defined as the concentration of ARM-H to bind 50% of the maximum bound HRP conjugated anti-DNP in the ternary complex with sgp120.

B. Varying Anti-DNP IgG Concentration (FIG. 4B)

Nunc-Immuno 96-well plates were coated with soluble gp120 and blocked as described above. After the PBS (Aldrich) wash, 25 µM □ of ARM-H (4) were added to the plate and incubated for 1 hr at RT. After washing (3×100 µL) the plate with Buffer D, wells were incubated with varying concentrations of rat monoclonal anti-dinitrophenyl (anti-DNP) IgG antibodies (Zymed; Carlsbad, Calif.) in Buffer E at room temperature for 1 hr. Plates were then washed, and incubated with HRP-conjugated goat anti-rat antibody. Bound antibody was detected with 3,3,5,5-tetramethylbenzidine (TMB; Pierce Protein Research Products), and the absorbance was read at 450 nm. The mean (±SD) of these triplicate samples was then plotted versus inhibitor concentration and a non-linear fit curve was generated using GraphPad Prism. The 50% effective concentration ($EC_{50}$) was defined as the concentration of anti-DNP antibody to bind 50% of the maximum bound HRP conjugated anti-DNP in the ternary complex with ARM-H (4).

*Note: The competition ELISAs were conducted following a known assay protocol containing a detergent (see Supporting Information Ref. 11), and had previously been employed to measure the $IC_{50}$ for BMS-378806, the parent compound in our studies. Utilizing these published conditions allowed us to calibrate our $IC_{50}$ values directly with literature values. However, when investigating recruitment of anti-DNP antibodies by ARM-H (FIG. 4), we utilized an ELISA buffer system that was compatible with tissue culture (i.e., one that lacks detergent) in order to model the conditions employed in subsequent CDC assays. Thus we would not expect an exact correlation between the competition ELISA $IC_{50}$ and the antibody recruiting ELISA $EC_{50}$ values. In addition, we recognize that the antibody/ARM-H/gp120 complex should exhibit auto-inhibitory behaviors consistent with ternary complex formation under certain circumstances, however, data collected in the antibody recruiting ELISA (FIG. 4) would not be expected to do so because of the assay conditions. A series of washes were performed prior to addition of anti-DNP antibody, thus removing unbound ARM-H, and preventing auto-inhibition by antibody/ARM-H complexes.

CHO Cell Culture

Wild-type HIV-1 env expressing CHO-WT (described as 'CHO-gp120' in the text) cells were obtained from the AIDS Research and Reference Reagent Program, Division of AIDS, NIAID, NIH: CHO-WT from Dr. Carol Weiss and Dr. Judith White. Cells were grown glutamine-deficient minimal essential medium containing 400 µM methionine sulfoximine (MSX, Sigma) (GMEM-S selection media) as described by associated NIH protocol[15]. CHO-K1 (described as 'CHO-WT' in the text) cells (ATCC) were grown in ATCC-formulated F-12K medium with 10% FBS (Gibco). Cells were detached from cell culture flasks with 2.5 mM EDTA/0.5 mM EGTA in DPBS (Gibco) for passage.

[15]. Weiss, C. D.; White, J. M. *J. Vir.* 1993, 67, 7060-7066.

*Note: As described in the associated NIH culture protocol, a drop in envelope expression in CHO-WT cells was observed upon several passages and it is recommended to maintain low passage stocks of cells in liquid nitrogen.

Immunofluorescence (FIG. 3)

Confluent CHO-WT (env expressing) or CHO-K1 (non-env expressing) cells were incubated on cover slips (15CIR-1D, Fisher) over 2 nights at 37° C. in 5% $CO_2$. Cover slips were washed with DPBS (1 mL, Gibco) and then cells fixed with 4% parafomaldehyde in DPBS at 4° C. for 10 minutes. To demonstrate antibody recruitment, cover slips were washed with DPBS (1×70 µl) then with Buffer E (1×70 µl) and incubated with ARM-H (4) in Buffer E (70 µl) for 1 hr at 4° C. Cover slips then washed with Buffer E (2×70 µl) and incubated with AlexaFluor488 rabbit anti-DNP IgG antibodies (Invitrogen) at 15 µg/ml in Buffer E (70 µl) for 1 hr at 4° C. All cover slips were washed prior to mounting onto slides using Gel Mount mounting medium (Biomeda Corp.) with Buffer E and water. Corresponding competition experiments were performed in the presence of recombinant human T-cell CD4 (ImmunoDiagnostics, Inc; Woburn, Mass.), BMS-378806 (1) and DNP-PEG-alkyne (2). Cells were checked using a Zeiss Axiovert 200M fluorescence microscope equipped with a GFP filter.

CDC Assay (FIG. 4 and FIG. 8)

CHO-WT or CHO-K1 cells taken from a T-75 flask (~80% confluent), were washed once with DPBS (Gibco, 5 mL), and cells were then detached with 2.5 mM EDTA/0.5 mM EGTA in DPBS. Resulting cell suspension was centrifuged at 900 rpm for five minutes, then pellet was aspirated and re-suspended at a density of $9.00×10^5$ cells/mL in Buffer E. Subsequently, cell suspension was added to prepared dilutions of ARM-H (4) (or control molecule) in Buffer E. Resulting cell mixtures were plated in triplicate (50 µL, 22,500 cells/well)□ onto 96 well plates (CoStar, black sides/clear bottom), covered with tin foil and incubated at 4° C. for 1.5 hours. To each well, 50 µL of 20% rabbit complement serum (v/v, Aldrich) and 100 µg/mL rat anti-DNP IgG (Zymed; Carlsbad, Calif.) in Buffer E was added, resulting in a 10% (v/v) complement and 50 µg/mL antibody concentration per well. Negative control wells containing only ARM-H dilutions were prepared in addition to maximum cell death controls (0.15% $H_2O_2$). Covered plate was incubated for an additional hour at 4° C. and then for 4 hours at room temperature. All control experiments were conducted following the same protocol. Cell viability was determined using the luciferase-based CellTiter-Glo Luminescent Cell Viability Assay (Promega). Complement mediated cell death and cytotoxicity was calculated as: [1−((sample-max killing)/(untreated-max killing))]×100 and plotted using GraphPad Prism. Raw data was subjected to Dixon Q-test analysis at the 90% confidence interval and statistical outliers removed accordingly[16,17].

[16]. Dean, R. B.; Dixon, W. J. *Anal. Chem.* 1951, 23, 636-638.

[17]. Efstathiou, C. E. *Talanta* 2006, 69, 1068-1071.

*Note: When performing above CDC analyses, authors observed consistent complement dependent cytotoxicity results over several CHO-gp120 cell passages. However, as reported in the NIH culture protocol, we observed a decrease in envelope protein, expression over many passages and associated with this decrease, we observed a considerable reduction in ARM-H (4) mediated CDC. In addition, at higher concentrations (>50 μM) of ARM-H and Azide (3), authors observed enhanced cell viability (decreased cell death) in both CHO-gp120 and CHO-WT cells, as shown in FIG. 8. Importantly, this effect was only observed at concentrations greater than ~50 μM, which is outside the concentration range reported in FIG. 9. Furthermore, since these effects lead to an enhancement in viability, they would tend to underestimate any effect ARM-H mediated antibody-dependent cytotoxicity.

Figures 8A, 8B:
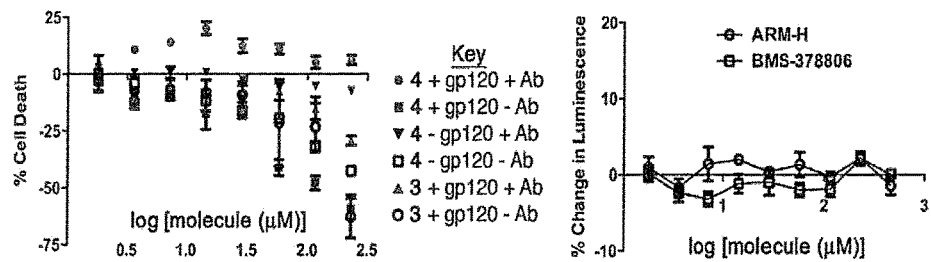
FIG. 8A shows the ARM-H mediated killing of CHO-gp120 cells and ATP control. ARM-H-mediated killing of CHO-gp120 cells and ATP control. HIV gp120-expressing CHO cells were treated in the presence or absence of antibody (rat anti-DNP IgG (50 mg/mL) and rabbit complement, plus the indicated concentrations of ARM-H or control compounds as detailed above. Decreased cell death (enhanced cell viability) is observed at concentrations greater than ~50 μM.
FIG. 8B shows the corresponding percent change in luminescence. In the absence of cellular material when assay reagents are combined with ARM-H or BMS-378806 (1) and ATP (50 nM), no increase/decrease in assay signal is observed. Values on the Y-axes correspond to the percent of cell death (versus background) or the corresponding percent change in luminescence. Data represents the mean±standard error. All individual experiments were performed in triplicate, and the indicated trends were reproduced on at least six separate occasions.
Figures 9A, 9B:
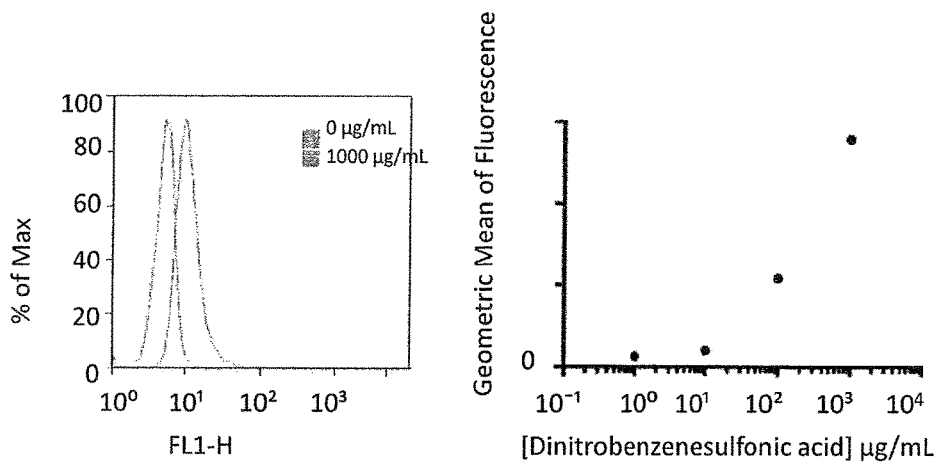
FIG. 9A shows the DNBSA labeling of CHO-K1 cells, showing the fluorescent shift; 2,4-Dinitrobenzenesulfonic acid labeling of CHO-K1 cells. Fluorescence shift of CHO-K1 cells labeled with dinitrobenzenesulfonic acid and then stained with AlexaFluor 488 conjugated anti-DNP IgG (20 μg/mL, green) compared to unlabeled cells (red).
FIG. 9B shows a concentration screen of dinitrobenzenesulfonic acid labeling of CHO-K1 cells as determined through flow cytometry. Note: Significant cell death detected at higher concentrations of dinitrobenzenesulfonic acid (data not shown).

Nevertheless, the inventors studied this phenomenon in more detail, and based upon follow up experiments, this enhancement in viability appears to take place independent of the presence of antibody/complement and gp120. It is also not due to a direct effect on assay reagents. Thus, following the general protocol for CDC experiments outlined above, we found that both ARM-H (4) and Azide (3) exhibit some degree of viability enhancement at high concentrations in both wild-type and gp120-expressing CHO cells (FIG. 8A). However, in the absence of all cellular material (FIG. 8B), when assay reagents are combined with either 1 or 4 and ATP (50 nM), no increase in assay signal is observed. Lastly, we expected to observe auto-inhibition, a phenomenon associated with ternary complexes that would favor gp120/ARM-H and ARM-H/antibody binary complexes over the ternary complex at higher concentrations of ARM-H in this assay. This behavior may exist at concentrations of ARM-H tested as shown in FIG. 9A (red dots) and may indeed explain the decrease in cell killing at higher concentrations of ARM-H in the presence of antibody and serum (Note: this ARM-H dependent CDC never attains "negative" values). However, this characteristic behavior cannot be confirmed, as it may be masked by the viability enhancement described above. Experiments to determine the cause of these phenomena are currently ongoing. The optimal ATP concentration was determined in FIG. 8B by generating a standard concentration-signal curve for ATP as outlined by the associated Promega protocol for CellTiter-Glo. Percent change in luminescence was calculated as: [1−(sample/untreated)]×100.

Figure 7:
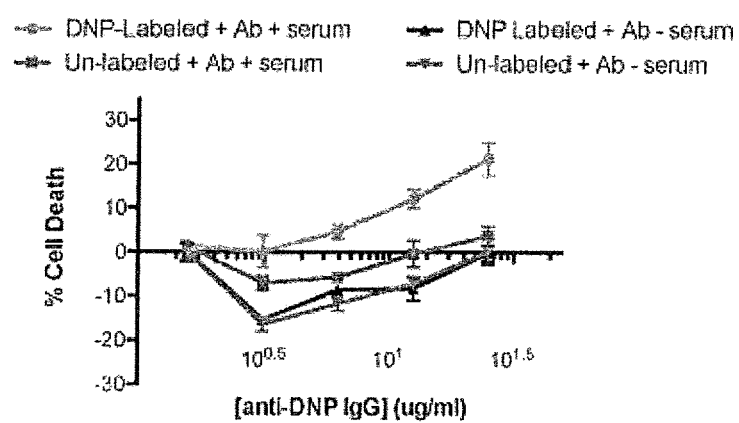
FIG. 7 shows the rat anti-DNP mediated CDC of dinitrobenzenesulfonic acid (DNBSA) labeled CHO-K1 cells. DNP labeled (see experimental) and un-labeled CHO-K1 cells were incubated with a concentration series of rat anti-DNP IgG antibodies in the presence and absence of rabbit complement serum. DNP-labeled cells, in the presence of serum (red), demonstrated a anti-DNP concentration dependent trend of cell death whereas unlabeled CHO-K1 cells (blue) demonstrated no cell death. Complement dependence of cell death was confirmed with incubations of antibody with labeled (black) and unlabeled (green) CHO-K1 cells in the absence of complement. Data represents the mean±standard error.

CDC Positive Control (FIG. 7)

With the goal of developing a positive control for the CDC assay, we screened a series of anti-gp120 antibodies and subjected them to the assay conditions above, however, none were capable of mediating CDC under our conditions. After extensive review of the literature, we found no examples of monoclonal or polyclonal anti-gp120 antibodies capable of mediating CDC of gp120-expressing cells. There are very few examples of anti-gp120 antibodies reported to mediate virolysis and in these reported antibody screens, no single antibody was capable of mediating virolysis beyond 20%[18,19]. Following a rigorous search, we found a commercially available antibody that has been reported[20] to mediate CDC to "gp120 V3-like protein" expressing activated T cells. In addition to this antibody, we screened 5 other antibodies, including: goat polyclonal anti-HIV-1-gp120 IgG (Abcam; Cambridge, Mass.; ab21179); rabbit polyclonal anti-HIV-1-gp120 IgG (Abbiotec, San Diego, Calif.; 250694); human anti-HIV-1-gp120 monoclonal (binds to CD4 binding region of gp120) IgG (ImmunoDiagnostics; Woburn, Mass.; 3501); mouse anti-HIV-1-gp120 monoclonal IgG1 (Novus; Littleton, Colo.; NB120-134H); rabbit polyclonal anti-HIV-1-gp120/160 IgG (Thermo; Rockford, Ill.; PA1-43526); anti-gp120 V3 loop (a.a.'s 308-322) monoclonal IgG (PerkinElmer; Waltham, Mass.; NEA9205)[15]. These results underscore the potential utility of these reported small molecule conjugates All gp120 antibodies were tested at concentrations up to 50 μg/mL (ImmunoDiagnostics #3501 was tested up to 25 μg/mL) and were performed once in triplicate. CHO-WT cells were detached and re-suspended at a density of 9.00×10$^5$ cells/mL in Buffer E as described above. Subsequently, cell suspension was added to prepared dilutions of anti-gp120 antibody in Buffer E. Resulting cell mixtures were plated in triplicate (50 μL, 22,500 cells/well)□ onto 96 well plates (CoStar, black sides/clear bottom), covered with tin foil and incubated at 4° C. for 1.5 hours. To each well, 50 μL of 20% rabbit complement serum (v/v, Aldrich) in Buffer E was added, resulting in a 10% (v/v) complement concentration per well. Negative control wells containing only antibody dilutions were prepared in addition to maximum cell death controls (0.15% $H_2O_2$). Covered plate was incubated for an additional hour at 4° C. and then for 4 hours at room temperature. Cell viability was quantitated with CellTiter-Glo Luminescent Cell Viability Assay as described above.

[18]. Spear, G. T.; Takefman, D. M.; Sullivan, B. L.; Landay, A. L.; Zolla-Panzer, S. J. Virol. 1993, 67, 53-59.
[19]. Takefman, D. M.; Sullivan, B. L.; Sha, B. E.; Spear, G. T. Virology, 1998, 246, 370-378.
[20]. Trujillo, J. R.; Rogers. R. A.; Brain, J. D. Virology 1998, 246, 53-62.

As an alternative, we were able to label CHO-K1 cells with 2,4-dintrobenzenesulfonic acid and mediate anti-DNP antibody dependent CDC (Supplementary FIG. 4), which was repeated twice and in triplicate. This procedure was adapted from the protocol reported by Geczy, et al.[21] CHO-K1 cells taken from a T-75 flask (~80% confluent), were washed once with DPBS (Gibco, 5 mL), and cells were then detached with 2.5 mM EDTA/0.5 mM EGTA in DPBS. Resulting cell suspension was centrifuged at 900 rpm for five minutes, then pellet was aspirated and re-suspended at a density of 9.0×10$^5$ cells/mL in F12-K growth medium. Cells were incubated with 2,4-dinitrobenzenesulfonic acid (TCI, 50 mg/mL solution in MeOH) at a concentration of 1 mg/mL for 30 min. at room temperature. Cells centrifuged and washed with growth medium (×2) and with Buffer E once. Cell suspension was added to prepared dilutions of rat anti-DNP IgG (Zymed; Carlsbad, Calif.) in Buffer E and subsequently plated in triplicate (50 μL, 22,500 cells/well)□ onto 96 well plates, covered with tin foil and incubated at 4° C. for 1.5 hours. To each well, 50 μL of 20% rabbit complement serum (v/v, Aldrich) in Buffer E was added, resulting in a 10% (v/v) complement concentration per well. Cell viability was quantitated as described above.

[18]. Geczy, A. F.; Baumgarten, A. Immunology, 1970, 19, 189-203.

Flow Cytometry Detection of DNP Labeling (FIG. 9)

CHO-K1 cells taken from a T-75 flask (~80% confluent), were washed once with DPBS (Gibco, 5 mL), and cells were then detached with 2.5 mM EDTA/0.5 mM EGTA in DPBS. Resulting cell suspension was centrifuged at 900 rpm for five minutes, then pellet was aspirated and re-suspended at a density of 1.40×10$^6$ cells/mL in F12-K growth medium. Cells were incubated with 2,4-dinitrobenzenesulfonic acid (TCI, 50 mg/mL solution in MeOH) at varying concentrations for 30 min. at room temperature. Cells centrifuged and washed with growth medium (×3) and then aliquoted (0.5 ml) into Eppendorf tubes at a cell density of 1.40×10$^6$ cells/mL. Cells incubated with AlexaFluor 488 conjugated rabbit anti-DNP IgG (Invitrogen) antibodies (20 μg/mL) for 1 hr at 4° C. Cells were subsequently centrifuged, washed with DPBS (3×0.5 mL), resuspended in 0.5 mL DPBS containing 150 µg of propidium iodide (to monitor cell death) and immediately analyzed for fluorescence using a FACSCalibur flow cytometer (Becton Dickinson) monitoring at least 10,000 events/measurement. Data were analyzed using FlowJo Analysis Software (Tree Star).

SUMMARY

The present invention meets the strategic need for a new treatment for HIV infection by providing bifunctional small molecules generally referred to as ARM-H's which function through orthogonal pathways—both by inhibition the gp120-CD4 interaction, and by recruiting anti-DNP antibodies to gp120-expressing cells—in preventing the cell infection and spread of HIV. It has been shown that: (1) ARM-H's bind to gp120 competitively with CD4 and decreases viral infectivity in an MT-2 cell assay, (2) the bifunctional molecule can guide the formation of a ternary complex between anti-DNP antibodies and both gp120 and gp120-expressing cells, and (3) antibodies present in this ternary complex can promote the complement-dependent destruction of gp120-expressing cells.

This antiviral approach has distinct advantages over other small-molecule, protein, and vaccine-based anti-HIV strategies.

Although the human immune response has been demonstrated to generate neutralizing anti-gp120 antibodies around which the virus does not effectively mutate, vaccine-based approaches toward inducing such antibodies in human hosts have not yet proven successful. In theory, although the HIV virus mutates extremely rapidly in human hosts, since it must retain CD4-binding activity in order to remain infectious, antibody-recruiting small molecules that mimic the CD4 recognition motif such as the ARM-H's of the invention have the hope of serving the same functional role as neutralizing anti-gp120 antibodies. Furthermore, as small molecules, these materials likely possess substantial advantages over protein-based therapeutics including low propensity for immunogenicity, high metabolic stability, ready large-scale production, and relatively low cost.

The evidence suggests that a cellular immune response is necessary for viral inactivation in vivo, and the bifunctional small molecules of the invention have been shown to directly target gp120-expressing particles to macrophages and neutophils.

This approach to antiviral therapy is also ideal as a prophylactic, as the bifunctional compound are not be expected to have any significant adverse side effects, being only active when virus is present.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

The invention claimed is:
1. A compound according to the chemical structure:

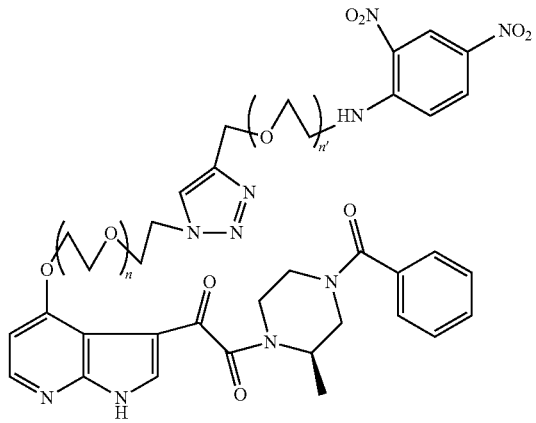

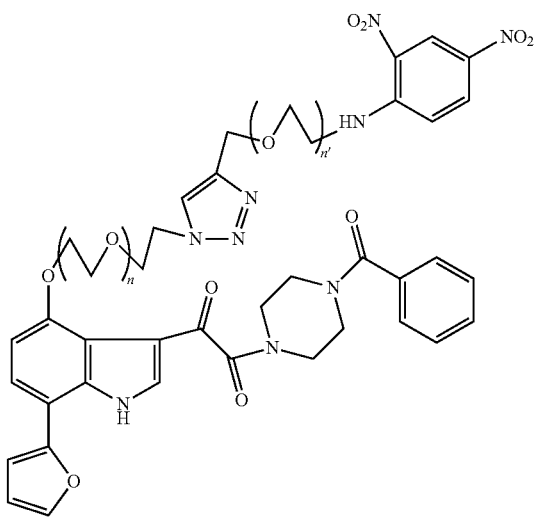

wherein n is 5 and n' is 4, or
a pharmaceutically acceptable salt thereof.

2. A pharmaceutical composition comprising an effective amount of a compound according to claim 1 in combination with a pharmaceutically acceptable carrier, additive or excipient.

3. The composition according to claim 2 further comprising an additional anti-HIV agent.

4. The composition according to claim 3 wherein said additional anti-HIV agent is said additional anti-HIV agent is selected from the group consisting of 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FD4C (Elvucitabine), NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), T20 (Enfuvirtide) and mixtures thereof.

5. A method of reducing HIV infected CD cells in a patient comprising administering to an HIV infected patient an effective amount of a composition according to claim 2.

6. A method of reducing HIV infected CD cells in a patient comprising administering to an HIV infected patient an effective amount of a composition according to claim 3.

* * * * *